United States Patent
Ochiya et al.

(10) Patent No.: US 11,260,072 B2
(45) Date of Patent: Mar. 1, 2022

(54) MICRORNA-BASED METHODS AND ASSAYS FOR OSTEOCARCINOMA

(71) Applicant: 3-D Matrix, Ltd., Tokyo (JP)

(72) Inventors: Takahiro Ochiya, Tokyo (JP); Tomohiro Fujiwara, Tokyo (JP)

(73) Assignee: 3-D Matrix, Ltd., Tokyo (JP)

( * ) Notice: Subject to any disclaimer, the term of this patent is extended or adjusted under 35 U.S.C. 154(b) by 0 days.

(21) Appl. No.: 16/501,468

(22) Filed: Apr. 4, 2019

(65) Prior Publication Data
US 2020/0316104 A1 Oct. 8, 2020
US 2021/0015843 A9 Jan. 21, 2021

Related U.S. Application Data

(60) Continuation of application No. 16/375,056, filed on Apr. 4, 2019, now Pat. No. 10,905,708, which is a continuation of application No. 15/096,480, filed on Apr. 12, 2016, now abandoned, which is a division of application No. 14/240,178, filed as application No.
(Continued)

(51) Int. Cl.
| | | |
|---|---|---|
| *A61K 31/7105* | (2006.01) | |
| *A61K 31/282* | (2006.01) | |
| *A61P 35/00* | (2006.01) | |
| *A61K 31/7115* | (2006.01) | |
| *A61K 45/06* | (2006.01) | |

(52) U.S. Cl.
CPC ........ *A61K 31/7105* (2013.01); *A61K 31/282* (2013.01); *A61K 31/7115* (2013.01); *A61P 35/00* (2018.01); *A61K 45/06* (2013.01)

(58) Field of Classification Search
CPC ............ C12N 15/113; C12N 2310/113; C12N 2310/141; C12N 2310/3231; C12N 2320/11; A61K 31/282; A61K 31/7105; A61K 31/7115; A61P 35/00
See application file for complete search history.

(56) References Cited

U.S. PATENT DOCUMENTS

| 9,322,016 B2 | 4/2016 | Ochiya et al. |
| 2006/0185027 A1 | 8/2006 | Bartel et al. |
| | (Continued) | |

FOREIGN PATENT DOCUMENTS

| CN | 102080086 | 6/2011 |
| WO | 2006116524 | 11/2006 |
| | (Continued) | |

OTHER PUBLICATIONS

Elmen, J. et al "LNA mediated microRNA silencing in non-human primates", Nature, 452(7189):896-900 (Nature Publishing Group Apr. 1, 2008).

(Continued)

*Primary Examiner* — Terra C Gibbs
(74) *Attorney, Agent, or Firm* — IP Supra, PLLC; Constantine Linnik

(57) ABSTRACT

Provided are methods and compositions useful in the diagnosis, treatment, and monitoring of osteosarcoma. Antisense to certain microRNA (miRNA) found to be associated with cancer stem cells (CSCs) or tumor-initiating cells (TICs) of osteosarcoma are useful to suppress tumor growth and metastasis, and prolong survival. Antisense oligonucleotides to miR-133a are synergistic in combination with standard chemotherapy such as cisplatin in the treatment of osteosarcoma.

14 Claims, 43 Drawing Sheets

Specification includes a Sequence Listing.

Related U.S. Application Data

PCT/IB2012/002626 on Sep. 7, 2012, now Pat. No. 9,322,016.

(60) Provisional application No. 61/696,981, filed on Sep. 5, 2012, provisional application No. 61/531,942, filed on Sep. 7, 2011.

(56) References Cited

U.S. PATENT DOCUMENTS

| | | |
|---|---|---|
| 2009/0005336 A1 | 1/2009 | Wang |
| 2011/0002880 A1 | 1/2011 | Takamura et al. |
| 2011/0021609 A1 | 1/2011 | Croce et al. |
| 2011/0201541 A1 | 8/2011 | Takamura et al. |
| 2014/0045917 A1 | 2/2014 | Nakashiro et al. |
| 2014/0243392 A1 | 8/2014 | Ochiya et al. |

FOREIGN PATENT DOCUMENTS

| | | |
|---|---|---|
| WO | 2008073392 | 6/2008 |
| WO | 2009072556 | 6/2009 |
| WO | 2010022166 | 2/2010 |
| WO | 2010136846 | 2/2010 |
| WO | 2010041636 | 4/2010 |

OTHER PUBLICATIONS

Fujiwara, T. et al., "Clinical Relevance and Therapeutic Significance of MicroRNA-133a Expression Profiles and Functions in Malignant Osteosarcoma-Initiating Cells," Stem Cells, 32(4):959-973 (AlphaMed Press, Apr. 2014).

Gougelet, A. et al., "Micro-RNA profiles in osteosarcoma as a predictive tool for ifosfamide response", International Journal of Cancer, 129(3):680-690 (UICC, Aug. 1, 2011).

Ji, F. et al., "MicroRNA-133a, downregulated in osteosarcoma, suppresses proliferation and promotes apoptosis by targeting Bcl-xL and Mcl-1", Bone, 56(1):220-226 (Elsevier, Inc., Jun. 10, 2013).

Miyachi, M. et al., "Circulating muscle specific microRNA, miR-206, as a potential diagnostic marker ro rhabdomyosarcoma", Biochemical and Biophysical Research Communications, 400(1):89-93 (Elsevier Inc., Sep. 10, 2010).

Obad, S. et al., "Silencing of microRNA families by seed targeting tiny LNAs", Nature Genetics, 43(4):371-378 (Nature America, Inc., Mar. 20, 2011).

Extended European Search Report from EP Patent Application EP 12828323.0, dated Apr. 2, 2015.

Fujiwara, T. et al., "Control of Osteosarcoma Stemness by RNA Interference", J. Jpn. Orthop. Assoc., 86:S837 I-3-FP3-4 (Japan, Jun. 2012).

Sun, L. et al., "MicroRNA-10b induces glioma cell invasion by modulating MMP-14 and uPAR expression via HOXD10"; Brain Research, 1389:9-18 (Elsevier, China, Mar. 2011).

IPRP and WO from PCT/IB2012/002626 dated Mar. 12, 2014.

Basu-Roy, U., et al., "Sox2 maintains self renewal of tumor-initiating cells in osteosarcomas," Oncogene 2012, 31, 2270-2282.

Brase, J.C., et al, "Serum microRNAs as non-invasive biomarkers for cancer," Molec. Cancer, 2010, v. 9, p. 306 (9 pages).

Caprara, G. et al, "Isolation and characterization of DUSP11, a novel p53 target gene," J. Cell. Mol. Med. vol. 13, No. 8B, 2009, pp. 2158-2170.

Croce, C. M., "Causes and consequences of microRNA dysregulation in cancer," Nat Rev Genet. Oct. 10, 2009 (10): 704-714.

Garland, P. et al, "Expression of the MAST family of serine/threonine kinases," Brain Res. Feb. 21, 2008:1195:12-19. doi: 10.1016/j.brainres.2007.12.027 Epub Dec. 23, 2007.

Gillette, J.M., et al., "Annexin 2 expression is reduced in human osteosarcoma metastases," J Cell Biochem. Jul. 1, 2004:92(4):820-32.

Gostissa, M. et al, "Activation of p53 by conjugation to the ubiquitin-like protein SUMO-1," EMBO J., 1999, v. 18, pp. 6462-6471.

Koshkin, A. A. et al, "LNA (Locked Nucleic Acids): Synthesis of the adenine, cytosine, guanine, 5-methylcytosine, thymine and uracil bicyclonucleoside monomers, oligomerisation, and unprecedented nucleic acid recognition," Tetrahedron, vol. 54, Issue 12, Apr. 2, 1998, pp. 3607-3630.

Krutzfeldt, J. et al, "Silencing of microRNAs in vivo with 'antagomirs'," Nature, 2005, v. 438, pp. 685-689.

Kuhn, N. Z. et al, "Regulation of Sternness and Stem Cell Niche of Mesenchymal Stem Cells: Implications in Tumoriginesis and Metastasis," J. Cell. Physiol., 2010, v. 222, pp. 268-277.

Levings, P. P. et al "Expression of an Exogenous Human Oct-4 Promoter Identifies Tumor-Initiating cells in Osteosarcoma," Cancer Res. Jul. 15, 2009; 69(14): 5648-5655.

Luu, H. H., "An orthotopic model of human osteosarcoma growth and spontaneous pulmonary metastasis," Clinical & Experimental Metastasis (2005) 22: 319-329.

Ma, L. et al, "Therapeutic silencing of miR-10b inhbits metastasis in a mouse mammary tumor model," Nat. Biotechnol., 2010, publ online Mar. 28, 2010, v. 28, pp. 341-347.

Nguyen, L.N. et al, "Sorting Nexin 1 Down Regulation Promotes Colon Tumorigenesis," Clin Cancer Res 2006; 12(23) pp. 6952-6959.

Obika, S et al, "Synthesis of 2?-O,4?-C-methyleneuridine and -cytidine. Novel bicyclic nucleosides having a fixed C3, endo sugar puckering," Tetrahedron Lett 1997; 38:8735-8.

Tang, N. et al, "Osteosarcoma Development and Stem Cell Differentiation," Clin Orthop Relat Res. Sep. 2008; 466(9); 2114-2130.

Carrie, D. et al, "Current Strategies of Chemotherapy in Osteosarcoma," International Orthopedics, (SICOT), 2006, vol. 30, pp. 445-451.

Extended European Search Report from EP Patent Application EP 12828087.2.

MICRORNA-BASED METHODS AND ASSAYS FOR OSTEOCARCINOMA

RELATED APPLICATIONS

This application is a continuation application of U.S. divisional application Ser. No. 15/096,480, filed Apr. 12, 2016, now abandoned; which is a divisional application of U.S. patent application Ser. No. 14/240,178, filed Apr. 9, 2014, now granted as U.S. Pat. No. 9,322,016; which is the U.S. national phase of international Patent Application No. PCT/IB2012/002626, filed Sep. 7, 2012; which claims benefit of priority to U.S. Provisional Patent Application No. 61/531,942, filed Sep. 7, 2011, and U.S. Provisional Patent Application No. 61/696,981, filed Sep. 5, 2012.

BACKGROUND OF THE INVENTION

There is growing evidence that tumors contain a subset of cells with stem cell-like properties. These cells, often referred to either as "cancer stem cells" (CSCs) or as "tumor-initiating cells" (TICs), are responsible for forming the bulk of tumor. These CSCs possess both self-renewal and differentiation capabilities, and are believed to give rise to tumor heterogeneity. Furthermore, they have been shown to be associated with the most lethal characteristics of tumors—drug resistance and metastasis. The first evidence of the existence of CSCs came from studies of hematological malignancies in 1994. More recently, CSCs have been identified in a number of solid tumors, including breast, brain, skin, lung, colon, pancreatic, liver, head and neck, prostate, ovarian, and gastric cancers.

Osteosarcoma is the most common primary bone malignancy and accounts for 60% of all malignant childhood bone tumors. Before multi-agent chemotherapy, amputation provided a long-term survival rate of only ~20%. Since the 1970s, combination chemotherapy along with limb-sparing surgery has been the main treatment for osteosarcoma. Currently, the 5-year survival for patients with osteosarcoma has been reported to be 50% to 80%. However, this survival rate has not improved over the last 10 years, and fully 40% of osteosarcoma patients die of their disease.

Targeting molecules important in tumorigenesis, known as "targeted therapy", has been an exciting development in cancer treatment in the past ten years. However, no targeted therapy is currently available for osteosarcoma. Therefore, there is a great need for developing new osteosarcoma treatments.

CD133, also known as AC133 and Prominin 1 (PROM1), is a five-transmembrane glycoprotein of unknown function. It was the first identified member of the prominin family of five-transmembrane glycoproteins. In 1997, Yin et al. produced a novel monoclonal antibody that recognized the AC133 antigen, a glycosylation-dependent epitope of CD133, and they detected expression of AC133 in CD34-positive progenitor cells from adult blood. CD133 cDNA encodes a 5-transmembrane domain molecule with an extracellular N-terminus, a cytoplasmic C-terminus, and two large extracellular loops with eight consensus sites for N-linked glycosylation. A characteristic feature of CD133 is its rapid downregulation during cell differentiation. This feature makes CD133 a unique cell surface marker for the identification and isolation of stem cells and progenitor cells in several tissues. According to the CSC theory, CSCs express some of the stem cell markers of normal stem cells. Therefore, tumor cells expressing CD133 independently or in combination with other stem cell or progenitor cell markers are thought to represent CSCs. To date, however, the molecular mechanisms underlying the phenotype of CSCs expressing CD133 cell surface marker have remained obscure.

MicroRNAs (miRNAs), first discovered in 1993 as a small non-protein-coding RNA, are small regulatory RNA molecules that modulate the expression of their target genes and play important roles in a variety of physiological and pathological processes, such as development, differentiation, cell proliferation, apoptosis, and stress responses. miRNA biogenesis requires several post-transcriptional processing steps to yield the functional mature miRNA. Over the past several years, many miRNAs have been investigated in various human cancers. The deregulation of the expression of miRNAs has been shown to contribute to cancer development through various kinds of mechanisms, including deletions, amplifications, or mutations involving miRNA loci, epigenetic silencing, the dysregulation of transcription factors that target specific miRNAs, or the inhibition of processing. miRNA expression profiling is of increasing importance as a useful diagnostic and prognostic tool, and many studies have indicated that miRNAs act either as oncogenes or as tumor suppressors.

The human miRNAs miR-1 and miR-133a are located on the same chromosomal region, in a so-called cluster. Enriched in muscle, they are miRNAs that inhibit proliferation of progenitor cells and promote myogenesis by targeting histone deacetylase 4 (HDAC4) and SCRIM response factor (SRF), respectively. miR-1 has been reported to be overexpressed in individuals with coronary artery disease, while both of these miRNAs have been reported to be expressed at low levels in cardiac hypertrophy. Despite a number of studies, their importance in muscle physiology and disease still remains unclear. Recently, miR-133a (the name of which bears no relationship to the name CD133) has been considered to be dispensable for the normal development and function of skeletal muscle. However, the relationship between these miRNAs and CSCs has, until now, been unknown.

The human miRNA miR-10b has been found to be positively associated with high-grade malignancy. This association held true for various types of cancer. miR-10b is one of the most significantly upregulated miRNAs in human pancreatic adenocarcinomas and glioblastomas, two types of highly metastatic and/or invasive cancers. This miRNA is highly expressed in metastatic cancer cells propagated as cell lines, as well as in metastatic breast tumors from patients, and is also upregulated in metastatic hepatocellular carcinomas relative to those that are not metastatic. The importance of miR-10b in sarcoma development has not previously been reported.

SUMMARY OF THE INVENTION

An aspect of the invention is a method of treating osteosarcoma. The method includes the step of administering to a subject in need thereof an effective amount of an antisense molecule specific for a microRNA (miRNA) selected from miR-1, miR-10b, and miR-33a.

In one embodiment, the antisense molecule is stabilized RNA.

In one embodiment, the stabilized RNA is a locked nucleic acid (LNA) oligonucleotide.

In one embodiment, the antisense molecule is DNA.

In one embodiment, the antisense molecule is 20-30 nucleotides long and comprises a nucleotide sequence at least 90 percent identical to 5'-ACATACTTCTTTACAT- TCCA-3' (SEQ ID NO:4), 5'-ACAAATTCGGTTCTA-CAGGGT-3' (SEQ ID NO:5), or 5'-CAGCTGGTT-GAAGGGGACCAA-3' (SEQ ID NO:6).

In one embodiment, the antisense molecule is 21-30 nucleotides long and comprises a nucleotide sequence at least 95 percent identical to 5'-ACATACTTCTTTACAT-TCCA-3' (SEQ ID NO:4), 5'-ACAAATTCGGTTCTA-CAGGGT-3' (SEQ NO:5), or 5'-CAGCTGGTT-GAAGGGGACCAA-3' (SEQ ID NO:6).

In one embodiment, the sequence of the antisense molecule is

```
                                         (SEQ ID NO: 4)
    5'-ACATACTTCTTTACATTCCA-3', (SEQ ID NO: 5)
    5'-ACAAATTCGGTTCTACAGGGT-3',
    or (SEQ ID NO: 6)
    5'-CAGCTGGTTGAAGGGGACCAA-3'.
```

In one embodiment, the antisense molecule is 20-30 nucleotides long and comprises a nucleotide sequence at least 90 percent identical to

```
                                         (SEQ ID NO: 7)
    5-AUACAUACUUCUUUACAUUCCA-3', (SEQ ID NO: 8)
    5'-CACAAAUUCGGUUCUACAGGGUA-3', (SEQ ID NO: 9)
    5'-CAGCUGGUUGAAGGGGACCAAA-3', (SEQ ID NO: 10)
    5'-ATACATACTTCTTTACATTCCA-3', (SEQ ID NO: 11)
    5'-CACAAATTCGGTTCTACAGGGTA-3',
    or (SEQ ID NO: 12)
    5'-CAGCTGGTTGAAGGGGACCAAA-3'.
```

In one embodiment, the antisense molecule is 21-30 nucleotides long and comprises a nucleotide sequence at least 95 percent identical to

```
                                         (SEQ ID NO: 7)
    5-AUACAUACUUCUUUACAUUCCA-3', (SEQ ID NO: 8)
    5'-CACAAAUUCGGUUCUACAGGGUA-3', (SEQ ID NO: 9)
    5'-CAGCUGGUUGAAGGGGACCAAA-3', (SEQ ID NO: 10)
    5'-ATACATACTTCTTTACATTCCA-3', (SEQ ID NO: 11)
    5'-CACAAATTCGGTTCTACAGGGTA-3',
    or (SEQ ID NO: 12)
    5'-CAGCTGGTTGAAGGGGACCAAA-3'.
```

In one embodiment, the sequence of the antisense molecule is

```
                                         (SEQ ID NO: 7)
    5-AUACAUACUUCUUUACAUUCCA-3', (SEQ ID NO: 8)
    5'-CACAAAUUCGGUUCUACAGGGUA-3', (SEQ ID NO: 9)
    5'-CAGCUGGUUGAAGGGGACCAAA-3', (SEQ ID NO: 10)
    5'-ATACATACTTCTTTACATTCCA-3', (SEQ ID NO: 11)
    5'-CACAAATTCGGTTCTACAGGGTA-3',
    or (SEQ ID NO: 12)
    5'-CAGCTGGTTGAAGGGGACCAAA-3'.
```

In one embodiment, the antisense molecule is associated with a nucleic acid delivery vehicle.

In one embodiment, the osteosarcoma is metastatic osteosarcoma.

An aspect of the invention is an isolated nucleic acid molecule 20-30 nucleotides long comprising a nucleotide sequence at least 90 percent identical to

```
                                         (SEQ ID NO: 4)
    5'-ACATACTTCTTTACATTCCA-3', (SEQ ID NO: 5)
    5'-ACAAATTCGGTTCTACAGGGT-3',
    or (SEQ ID NO: 6)
    5'-CAGCTGGTTGAAGGGGACCAA-3'.
```

In one embodiment, the isolated nucleic acid molecule is 21-30 nucleotides long and comprises a nucleotide sequence at least 95 percent identical to

```
                                         (SEQ ID NO: 4)
    5'-ACATACTTCTTTACATTCCA-3', (SEQ ID NO: 5)
    5'-ACAAATTCGGTTCTACAGGGT-3',
    or (SEQ ID NO: 6)
    5'-CAGCTGGTTGAAGGGGACCAA-3'.
```

In one embodiment, the sequence of the isolate ucleic acid molecule is

```
                                         (SEQ ID NO: 4)
    5'-ACATACTTCTTTACATTCCA-3', (SEQ ID NO: 5)
    5'-ACAAATTCGGTTCTACAGGGT-3',
    or (SEQ ID NO: 6)
    5'-CAGCTGGTTGAAGGGGACCAA-3'.
```

An aspect of the invention is an isolated nucleic acid molecule 20-30 nucleotides long comprising a nucleotide sequence at least 90 percent identical to

```
                                         (SEQ ID NO: 7)
    5-AUACAUACUUCUUUACAUUCCA-3', (SEQ ID NO: 8)
    5'-CACAAAUUCGGUUCUACAGGGUA-3',
```

-continued

```
                                              (SEQ ID NO: 9)
5'-CAGCUGGUUGAAGGGGACCAAA-3', (SEQ ID NO: 10)
5'-ATACATACTTCTTTACATTCCA-3', (SEQ ID NO: 11)
5'-CACAAATTCGGTTCTACAGGGTA-3',
or (SEQ ID NO: 12)
5'-CAGCTGGTTGAAGGGGACCAAA-3'.
```

In one embodiment, the isolated nucleic acid molecule is 21-30 nucleotides long and comprises a nucleotide sequence at least 95 percent identical to

```
                                              (SEQ ID NO: 7)
5-AUACAUACUUCUUUACAUUCCA-3', (SEQ ID NO: 8)
5'-CACAAAUUCGGUUCUACAGGGUA-3', (SEQ ID NO: 9)
5'-CAGCUGGUUGAAGGGGACCAAA-3', (SEQ ID NO: 10)
5'-ATACATACTTCTTTACATTCCA-3', (SEQ ID NO: 11)
5'-CACAAATTCGGTTCTACAGGGTA-3',
or (SEQ ID NO: 12)
5'-CAGCTGGTTGAAGGGGACCAAA-3'.
```

In one embodiment, the sequence of the isolated nucleic acid molecule is

```
                                              (SEQ ID NO: 7)
5-AUACAUACUUCUUUACAUUCCA-3', (SEQ ID NO: 8)
5'-CACAAAUUCGGUUCUACAGGGUA-3', (SEQ ID NO: 9)
5'-CAGCUGGUUGAAGGGGACCAAA-3', (SEQ ID NO: 10)
5'-ATACATACTTCTTTACATTCCA-3', (SEQ ID NO: 11)
5'-CACAAATTCGGTTCTACAGGGTA-3',
or (SEQ ID NO: 12)
5'-CAGCTGGTTGAAGGGGACCAAA-3'.
```

In one embodiment, the nucleic acid molecule is associated with a nucleic acid delivery vehicle.

An aspect of the invention is a method of assessing resistance of osteosarcoma to an anti-cancer therapy. The method includes the steps of:

obtaining a tissue sample comprising osteosarcoma cells;

isolating from the sample cells expressing CD133;

measuring a first level of expression by the CD133-expressing cells of at least one microRNA (miRNA) selected from the group consisting of miR-1, miR-10b, and miR-133a;

contacting the CD133-expressing cells with an anti-cancer therapy; and measuring a second level of expression by the CD133-expressing cells of the at least one miRNA, wherein a second level of expression greater than the first level of expression indicates the osteosarcoma is resistant to the anti-cancer therapy.

In one embodiment, the anti-cancer therapy is selected from the group consisting of cisplatin, doxorubicin, methotrexate, and any combination thereof.

An aspect of the invention is a method of screening for osteosarcoma. The method includes the step of performing on a tissue sample from a subject an assay specifically capable of detecting at least one microRNA (miRNA) selected from the group consisting of miR-1, miR-10b, and miR-133a, wherein detection by the assay of the presence in the sample of the at least one miRNA indicates the subject is at risk of having osteosarcoma.

In one embodiment, the tissue is blood.

In one embodiment, the tissue is serum.

An aspect of the invention is a method of monitoring osteosarcoma. The method includes the steps of:

(a) performing, on a tissue sample obtained from a subject having osteosarcoma or having been treated for osteosarcoma, an assay specifically capable of quantifying the level of expression of at least one microRNA (miRNA) selected from the group consisting of miR-1, miR-10b, and miR-133a; and (b) repeating step (a) on a later-obtained tissue sample from the subject, wherein a level of expression of the at least one miRNA in the later-obtained sample greater than the level of expression of the at least one miRNA in the earlier-obtained sample indicates the osteosarcoma is progressive, and a level of expression of the at least one miRNA in the later-obtained sample lesser than the level of expression of the at least one miRNA in the earlier-obtained sample indicates the osteosarcoma is regressive.

In one embodiment, the tissue is blood.

In one embodiment, the tissue is serum.

BRIEF DESCRIPTION OF THE DRAWINGS

FIG. 5 is a pair of photomicrographs and a bar graph depicting invasion assays in $CD133^{high}$ and $CD133^{low}$ SaOS2 cell populations (n=3 per group, **P<0.01). Scale bar, 200 μm.

DETAILED DESCRIPTION OF THE INVENTION

Figure 1:
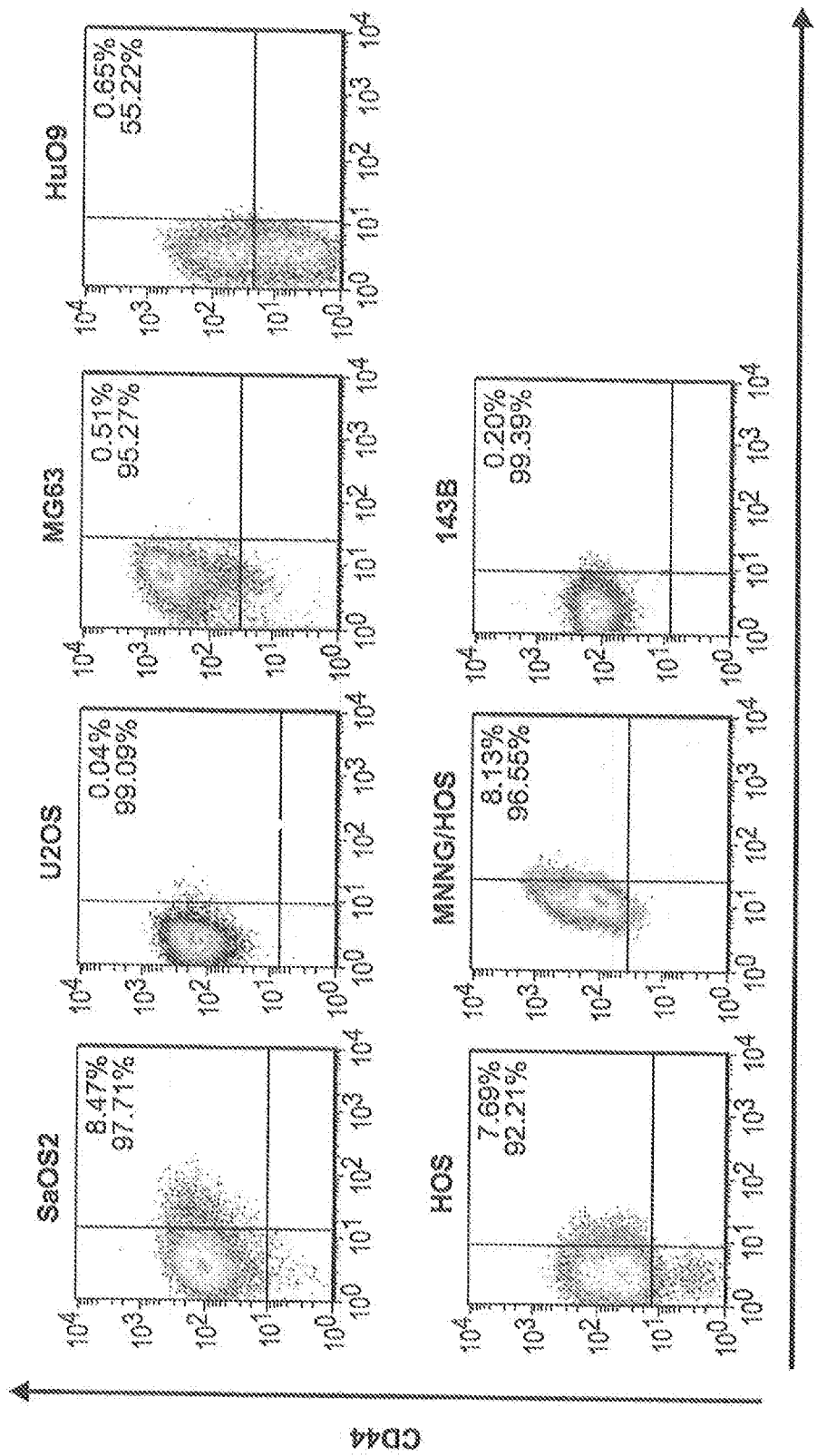
FIG. 1 is a group of seven representative: FACS analyses of various indicated human osteosarcoma cell lines based on their expression of CD 133 (X-axis) and CD44 (Y-axis).

Since the proposal of the cancer stem cell (CSC) hypothesis, several studies have been performed to identify cancer stem cells of osteosarcoma. These cells have been detected in spherical clones under anchorage-independent, serum-starved culture conditions, as side population (SP) cells based on efflux of Hoechst 33342 dye or as CD117 and stro-1 cells sorted using cell surface marker. In view of these models, the inventors identified Prominin-1, the mouse homolog of human CD133, to be highly expressed in a small fraction of osteosarcoma cells, Cells from this $CD133^{high}$ fraction formed cluster spheres in an anchorage-independent environment, exhibited a potential for self-renewal and differentiation, expressed stem cell-associated markers, and showed more invasive potential compared to the $CD133^{low}$ fraction.

Following the characterization of the phenotype of osteosarcoma CSCs, the inventors profiled expression of several miRNAs, which distinguish cells of the $CD133^{high}$ fraction from their more differentiated progeny. Among these miR-NAs, miR-1, miR-10b, miR-133a were found to be upregulated in the $CD133^{high}$ fraction compared to the $CD133^{low}$ fraction of osteosarcoma cells. Remarkably, the inventors have discovered these miRNAs promote chemoresistance and invasiveness of osteosarcoma cells. These observations suggest that miR-1, miR-10b, and miR-133a are regulators of cancer stem cells of osteosarcoma. Particularly in combination with a tailored drug delivery system, new therapeutic agents (e.g., antisense nucleotides) targeting the miR-NAs show great promise against osteosarcoma, adding to conventional chemotherapeutic agents, such as methotrexate, cisplatin, and doxorubicin.

Although miRNAs are not presently used as cancer therapeutics or as validated targets for cancer therapeutics, successful in vivo studies support the notion that they could be used as innovative therapeutics to address unmet needs. Systemic delivery of anti-miR-10b in an orthotopic mouse model of breast cancer showed a significant reduction in the number and size of lung metastases, with no obvious effect on primary tumors. Ma et al, (2010) *Nat Biotechnal* 28:341-7. Moreover, the recent discovery of miRNAs as novel biomarkers in serum or plasma represents a new approach for diagnostic screening in blood. Brase et al. (2010) *Mol Cancer* 9:306. The miRNAs identified in accordance with the instant invention also have potential as biomarkers which can be used for prompt assessment of sensitivity to chemotherapeutics, early detection of local recurrence, or distant metastasis, all of which are factors that affect the prognosis for patients with osteosarcoma.

An aspect of the invention is a method of treating osteosarcoma. The method includes the step of administering to a subject in need thereof an effective amount of an antisense molecule specific for a microRNA (miRNA) selected from miR-1, miR-10b, and miR-133a. Alternatively or in addition, the method can include the step of administering to the subject any agent that knocks down the expression of the miRNA.

As used herein, the terms "treating" and "to treat" refers to ameliorating or curing a disease or undesirable condition. For example, treating osteosarcoma refers to reducing or eliminating the burden of osteosarcoma cells in a subject having osteosarcoma.

A "subject" as used herein refers to a mammal. In one embodiment, a subject is a human.

An effective amount of an antisense molecule specific for a microRNA is administered to the subject in need of treatment. As used herein, an "effective amount" refers to an amount that is sufficient to achieve a desired biological outcome. For example, an effective amount to treat an osteosarcoma is an amount sufficient to reduce or eliminate the population of osteosarcoma cells in a subject having osteosarcoma. An effective amount may vary depending on such factors as the size of the tumor, the size of the subject, the overall condition of the subject, the route of administration, the identity of the active agent, the composition or formulation of the active agent, and other factors well known in the medical and pharmaceutical arts.

Without meaning to be bound to any particular dosage, an effective amount can, in general, vary from 0.01 microgram (μg)/kg body weight to 1000 mg/kg body weight of active agent per day when administered by a parenteral route of administration. For oral or enteral administration, an effective amount can, in general, vary from 0.1 μg/kg body weight to 10,000 mg/kg body weight of active agent per day. An effective amount can be determined, for example, based on in vitro studies and in vivo animal studies, as well as clinical studies.

MicroRNAs (miRNAs) are short (20-24 nt) non-coding RNAs that are involved in post-transcriptional regulation of gene expression in multicellular organisms by affecting both the stability and translation of mRNAs. miRNAs are transcribed by RNA polymerase II as part of capped and polyadenylated primary transcripts (pri-miRNAs) that can be either protein-coding or non-coding. The primary transcript is cleaved by the Drosha ribonuclease III enzyme to produce an approximately 70-nt stem-loop precursor miRNA (pre-miRNA), which is further cleaved by the cytoplasmic Dicer ribonuclease to generate the mature miRNA and antisense miRNA star (miRNA*) products. The mature miRNA is incorporated into an RNA-induced silencing complex (RISC), which recognizes target messenger RNAs (mRNAs) through imperfect base pairing with the miRNA and most commonly results in translational inhibition or destabilization of the target mRNA.

The miRNA can be selected from miR-1, miR-10b, and miR-133a, In one embodiment, the miRNA is miR-1. In one embodiment, the miRNA is miR-10b. In one embodiment, the miRNA is miR-133a. While these miRNAs have been described in the art, prior to the instant invention there was no recognition or expectation that these particular miRNAs are or might he associated with osteosarcoma, including, in particular, drug-resistant and/or aggressively invasive or metastatic phenotypes of osteosarcoma.

miR-1 has been described as a 22-nucleotide long miRNA having the sequence (SEQ ID NO: 1)
5'-UGGAAUGUAAAGAAGUAUGUAU-3'.

miR-10b has been described as a 23-nucleotide long miRNA having the sequence (SEQ ID NO: 2)
5'-UACCCUGUAGAACCGAAUUUGUG-3'.

miR-133a has been described as a 22-nucleotide long miRNA having the sequence (SEQ ID NO: 3)
5'-UUUGGUCCCCUUCAACCAGCUG-3'.

Antisense is well described in the literature. In general, antisense agents are nucleic acid-based molecules having a nucleotide sequence that is complementary to the sequence of a target nucleic acid molecule, whereby association between the antisense molecule and its target sequence molecule results in a reduced amount of expression of the target nucleic acid molecule.

In one embodiment the antisense molecule (anti-miRNA) is a stabilized RNA, i.e., an RNA that, compared to naturally occurring RNA, is relatively resistant to nuclease-mediated degradation in vitro or in viva. Numerous forms of stabilized nucleic acids, including RNA, are known. Some stabilized RNAs include polyA 3'-terminal ends. Chemically modified forms of nucleic acids, including, for example and without limitation, locked nucleic acids (LNAs), phosphorothioate backbone-modified nucleic acids, and 2'-O-methyl (2'-OMe) nucleic acids have been well described and require no further description here. Krützfeldt et al. (2005) *Nature* 438:685-9; Ma et al. (2010) *Nat Biotechnol* 28:341-7.

In one embodiment, the antisense molecule is a locked nucleic acid (LNA) oligonucleotide. A locked nucleic acid nucleotide is a modified ribonucleotide. The ribose moiety of an LNA nucleotide is modified with an extra bridge connecting the 2' oxygen and 4' carbon. The bridge "locks" the ribose in the 3'-endo conformation. LNA nucleotides were first developed by Imanishi and colleagues and Wengel and colleagues. Obika et al. (1997) *Tetrahedron Lett.* 38:8735-8; Koshkin et al. (1998) *Tetrahedron* 54:3607-30.

A locked nucleic acid (LNA) oligonucleotide is a polymer of nucleotides, at least one of which is an LNA nucleotide. Any non-LNA nucleotide in an LNA oligonucleotide can be a naturally occurring or modified ribonucleotide or deoxyribonucleotide, or an analog thereof, provided that the LNA oligonucleotide is functional as an antisense molecule with respect to its intended target. In one embodiment, any non-LNA nucleotide in an LNA oligonucleotide is a deoxyribonucleotide, and at least the 3'-terminal nucleotide is an LNA nucleotide. In one embodiment, any non-LNA nucleotide in an LNA oligonucleotide is a naturally occurring deoxyribonucleotide, and at least the two 3'-terminal nucleotides are LNA nucleotides. In one embodiment, an LNA oligonucleotide is composed exclusively of LNA nucleotides.

In one embodiment, the antisense molecule is DNA.

In one embodiment, an antisense molecule specific for miR-1 comprises a sequence (SEQ ID NO: 4)
5'-ACATACTTCTTTACATTCCA-3'.

In one embodiment, the sequence of an antisense molecule specific for miR-1 is (SEQ ID NO: 4)
5'-ACATACTTCTTTACATTCCA-3'.

In one embodiment, an antisense molecule specific for miR-10b comprises a sequence 5'-ACAAATTCGGTTCTA-CAGGGT-3' (SEQ ID NO:5).

In one embodiment, the sequence of an antisense molecule specific for miR-10b is (SEQ ID NO: 5)
5'-ACAAATTCGGTTCTACAGGGT-3'.

In one embodiment, an antisense molecule specific for miR-133a comprises a sequence 5'-CAGCTGGTT-GAAGGGGACCAA-3' (SEQ ID NO:6).

In one embodiment, the sequence of an antisense molecule specific for miR-133a is (SEQ ID NO: 6)
5'-CAGCTGGTTGAAGGGGACCAA-3'.

in one embodiment, an antisense molecule specific fur raiR-1 comprises a sequence (SEQ ID NO: 7)
5'-AUACAUACUUCUUUACAUUCCA-3'.

In one embodiment, the sequence of an antisense molecule specific for miR-1 is (SEQ ID NO: 7)
5'-AUACAUACUUCUUUACAUUCCA-3'.

In one embodiment, an antisense molecule specific for miR-10b comprises a sequence 5'-CACAAAUUCGGUUC-UACAGGGUA-3' (SEQ ID NO:8).

In one embodiment, the sequence of an antisense molecule specific for MR-10b is

5'-CACAAAUUCGGUUCUACAGGGUA-3'. (SEQ ID NO: 8)

In one embodiment, an antisense molecule specific for miR-133a comprises a sequence 5'-CAGCUG-GUUGAAGGGGACCAAA-3' (SEQ ID NO:9).

In one embodiment, the sequence of an antisense molecule specific for miR-133a is

5'-CAGCUGGUUGAAGGGGACCAAA-3'. (SEQ ID NO: 9)

In one embodiment, an antisense molecule specific for miR-1 comprises a sequence

5'-ATACATACTTCTTTACATTCCA-3'. (SEQ ID NO: 10)

In one embodiment, the sequence of an antisense molecule specific for miR-1 is

5'-ATACATACTTCTTTACATTCCA-3'. (SEQ ID NO: 10)

In one embodiment, an antisense molecule specific for miR-10b comprises a sequence 5'-CACAAATTCGGTTC-TACAGGGTA-3' (SEQ ID NO:11).

In one embodiment, the sequence of an antisense molecule specific for miR-10b is

5'-CACAAATTCGGTTCTACAGGGTA-3'. (SEQ ID NO: 11)

In one embodiment, an antisense molecule specific for miR-133a comprises a sequence 5'-CAGCTGGTT-GAAGGGGACCAAA-3' (SEQ ID NO:12).

In one embodiment, the sequence of an antisense molecule specific for miR-133a is

5'-CAGCTGGTTGAAGGGGACCAAA-3'. (SEQ ID NO: 12)

The invention further embraces antisense molecules 20 to 30 nucleotides long comprising a contiguous sequence that is at least 90 percent identical to any one of the foregoing antisense molecule sequences. It is to be understood that such antisense molecules are capable of specifically hybridizing with or knocking down expression of the miRNAs to which they are targeted.

The invention further embraces antisense molecules 21 to 30 nucleotides long comprising a contiguous sequence that is at least 95 percent identical to any one of the foregoing antisense molecule sequences. It is to be understood that such antisense molecules are capable of specifically hybridizing with or knocking down expression of the miRNAs to which they are targeted.

In each of the foregoing embodiments, in one embodiment the antisense molecule includes one or more locked nucleic acid (LNA) nucleotides. Furthermore, in one embodiment the antisense molecule is composed exclusively of locked nucleic acid (LNA) nucleotides.

In one embodiment, the, antisense molecule specific for a particular microRNA is associated with a nucleic acid delivery vehicle. As used herein, a "nucleic acid delivery vehicle" refers to a biologically compatible vector useful for delivering a nucleic acid molecule to the cytoplasm of a cell. The antisense molecule can be conjugated to the nucleic acid delivery vehicle. Alternatively or in addition, the antisense molecule can be encapsulated by the nucleic acid delivery vehicle. Examples of suitable nucleic acid delivery vehicles include liposomes, lipids, cholesterol, hormones, and other targeting molecules. In respect of liposomes, the antisense molecule can be associated with the outer surface of the liposome, the interior of the liposome, or both the exterior and the interior of the liposome.

In one embodiment, the osteosarcoma is localized osteosarco osteosarcoma that is confined to one limb or one bone.

In one embodiment, the osteosarcoma is metastatic osteosarcoma.

An aspect of the invention is a method of assessing resistance of osteosarcoma to an anti-cancer therapy. The method includes the steps of obtaining a tissue sample comprising osteosarcoma cells;
isolating from the sample cells expressing CD133;
measuring a first level of expression by the CD133-expressing cells of at least one microRNA (miRNA) selected from the group consisting of miR-1, miR-10b, and miR-133a;
contacting the CD133-expressing cells with an anti-cancer therapy; and
measuring a second level of expression by the CD133-expressing cells of the at least one miRNA, wherein a second level of expression greater than the first level of expression indicates the osteosarcoma is resistant to the anti-cancer therapy.

CD133-expressing cells can be isolated from a tissue sample using any suitable means. For example, a cell suspension can be prepared from the tissue and then the cells can be subjected to immunochromatography with, for example, magnetic beads loaded with anti-CD133 antibody, or by fluorescence-activated cell sorting (FACS) using an appropriately labeled anti-CD133 antibody. Monoclonal anti-human CD133 antibodies are commercially available from a number of suppliers.

A level of expression of a miRNA can be performed using any suitable method. For example, the expression level can be determined using reverse-transcriptase polymerase chain reaction (RT-PCR) using appropriately selected oligonucleotide primers.

Alternatively or in addition, the expression level can be determined using Northern blotting with appropriately selected and labeled hybridization probe.

As used herein, an "anti-cancer therapy" refers to any modality of treatment useful to treat a cancer. Such modalities include, in general, chemotherapy, external beam radiation therapy, immunotherapy, hormone therapy, and combinations thereof.

Chemotherapeutic agents are small molecules (molecular weight less than about 1 kDa) are well known in the medical arts. Commonly used chemotherapeutic agents used for osteosarcoma include cisplatin (cis-diamtninedichloroplatinum (II), also known as CDDP, and cisplatirium, commercially available as Platinol and Platinol-AQ), doxorubicin (also known as hydroxydaunorubicin, commercially available as Adriamycin), and methotrexate (also known as amethopterin). In one embodiment, the anti-cancer therapy is selected from cisplatin, doxorubicin, methotrexate, and any combination thereof. Any two or more of these agents may be used in combination, either concurrently or sequentially. In addition, any one or combination of such anti-cancer therapies can be used in combination with another anti-cancer modality, for example, external beam radiation therapy.

In various embodiments, the osteosarcoma is identified as being resistant to the anti-cancer therapy when the second level of expression of at least one of miR-1, miR-10b, and miR-133a is objectively greater than the first level of expression. In various embodiments, the osteosarcoma is identified as being resistant to the anti-cancer therapy when the second level of expression of at least one of miR-1, miR-10b, and miR-133a is at least 10 percent, at least 20 percent, at least 30 percent, at least 40 percent, at least 50 percent, at least 60 percent, at least 70 percent, at least 80 percent, at least 90 percent, or at least 100 percent greater than the first level of expression.

In one embodiment, the method further comprises the step of adjusting the dose of or changing the anti-cancer therapy when the osteosarcoma is found to be resistant to the anti-cancer therapy. For example, when the osteosarcoma is found to be resistant to the anti-cancer therapy, the anti-cancer therapy can be supplemented with or changed to another suitable anti-cancer therapy.

An aspect of the invention is a method of screening for osteosarcoma. The method includes the step of performing on a tissue sample obtained from a subject an assay specifically capable of detecting at least one microRNA (miRNA) selected from the group consisting of miR-1, miR-10b, and miR-133a, wherein detection by the assay of the presence in the sample of the at least one miRNA indicates the subject is at risk of having osteosarcoma. In one embodiment, the miRNA is miR-1. In one embodiment, the miRNA is miR-10b. In one embodiment, the miRNA is miR-133a. In one embodiment, the at least one mi-RNA is any combination of miR-1, miR-10b, and miR-133a.

An assay specifically capable of detecting at least one microRNA (miRNA) selected from the group consisting of miR-1, miR-10b, and miR-133a can be, for example, RT-PCR. using appropriately selected oligonucleotide primers. Alternatively or in addition, the assay can be Northern blotting with an appropriately selected and labeled hybridization probe.

In one embodiment, the tissue is blood. In one embodiment, the tissue is serum. In one embodiment, the tissue is plasma.

In one embodiment, the method further includes the step of verifying the presence of osteosarcoma, using any suitable method, when the subject is determined to be at risk of having osteosarcoma. For example, verifying the presence of osteosarcoma can include performing a skeletal survey or specific bone imaging analysis using X-rays or other suitable bone imaging technique, magnetic resonance imaging (MRI), computed tomography (CT), biopsy, and any combination thereof.

In one embodiment, the method further includes the step of treating the subject for osteosarcoma.

An aspect of the invention is a method of monitoring osteosarcoma. The method includes the steps of (a) performing, on a tissue sample obtained from a subject having osteosarcoma or having been treated for osteosarcoma, an assay specifically capable of quantifying the level of expression of at least one microRNA (miRNA) selected from the group consisting of miR-1, miR-10b, and miR-133a; and (b) repeating step (a) on a later-obtained tissue sample from the subject, wherein a level of expression of the at least one miRNA in the later-obtained sample greater than the level of expression of the at least one miRNA in the earlier-obtained sample indicates the osteosarcoma is progressive, and a level of expression of the at least one miRNA in the later-obtained sample lesser than the level of expression of the at least one miRNA in the earlier-obtained sample indicates the osteosarcoma is regressive.

An assay specifically capable of quantifying the level of expression of at least one microRNA (miRNA) selected from the group consisting of miR-1, miR-10b, and miR-133a can be, for example, RT-PCR using appropriately selected oligonucleotide primers.

In one embodiment, the tissue is blood. In one embodiment, the tissue is serum. In one embodiment, the tissue is plasma.

In one embodiment, the method further includes the step of adjusting the dose of or changing anti-cancer therapy when the osteosarcoma is found to be progressive. For example, when the osteosarcoma is found to be progressive, the anti-cancer therapy can be supplemented with or changed to another suitable anti-cancer therapy.

In one embodiment, the method further includes the step of adjusting the dose of or changing anti-cancer therapy when the osteosarcoma is found to be regressive. For example, when the osteosarcoma is found to be regressive, the anti-cancer therapy can be reduced or even suspended, or the anti-cancer therapy can be changed to another suitable anti-cancer therapy.

The invention, now having been generally disclosed, is further illustrated by the following non-limiting examples.

EXAMPLES

General Methods

Osteosarcoma cell purification from fresh clinical samples. Fresh human osteosarcoma samples were obtained in accordance with the ethical standards of the institutional committee on human experimentation from two patients undergoing diagnostic incisional biopsy from primary sites of osteosarcoma before neoadjuvant chemotherapy at the National Cancer Center Hospital of Japan between October 2010 and June 2011. The diagnosis of osteosarcoma and histologic subtypes were determined by certified pathologists. Surgical specimens were obtained at the time of resection and received in the laboratory within 10 minutes, immediately mechanically disaggregated and digested with collagenase and (Nitta-gelatin) and washed in phosphate-buffered saline (PBS) twice. Single-cell suspensions were obtained by filtration through a 70 μm filter (BD Biosciences). Cells were cultured in Dulbecco's modified Eagle's medium (DMEM) (Invitrogen) containing 10% heat-inactivated fetal bovine serum (FBS) (Gibco BRL) and penicillin (100 U/mL) and streptomycin (100 μg/mL) under 5% $CO_2$ in a in a humidified incubator at 37° C.

Cells and cell culture. The human osteosarcoma. HuO9 cell line was previously established in the applicant's laboratory. The human osteosarcoma cell lines SaOS2, U2OS, MG63, HOS, MNNG/HOS, and 143B were purchased from the American Type Culture Collection (ATCC). The transformed embryonic kidney cell line 293 was also obtained from the ATCC. SaOS2 and HuO9 cells were cultured in RPMI 1640 medium (Gibco BRL). U2OS, MG63, HOS, MNNG/HOS, 143B, and 293 cells were cultured in DMEM (Invitrogen). All media were supplemented with 10% heat-inactivated FBS (Gihco BRL) and penicillin (100 U/mL)

and streptomycin (100 μg/mL). The cells were maintained under 5% $CO_2$ in a humidified incubator at 37° C.

Cell sorting and flow cytometry. Cell sorting by flow cytometry was performed on osteosarcoma cell lines and clinical samples using phycoerythrin (PE)-conjugated monoclonal mouse anti-human CD133/2 (293C3, Miltenyi Biotec) and allophycocyanin (APC)-conjugated monoclonal mouse anti-human CD44 (eBioscience). Isotype control mouse IgG1κ-PE (eBioscience) served as a control. Samples were analyzed and sorted on the JSAN cell sorter (Baybioscience) and the BD FACS AriaII (BD Biosciences). Viability was assessed using trypan blue exclusion. Results were analyzed with FlowJo software (Tree Star).

Cell proliferation and cytotoxity assay. Cell proliferation rates and cell viability as an indicator for the relative sensitivity of the cells to doxorubicin, cisplatin, and methotrexate were determined using TetraColor ONE Cell proliferation Assay System (Seikagaku) according to the manufacturer's instructions. Cells growing in the logarithmic phase were seeded in 96-well plates ($5×10^3$/well), allowed to attach overnight, and then were treated with varying doses of doxorubicin (Sigma), cisplatin (Alexis), and methotrexate (Sigma) for 72 h. Triplicate wells were used for each treatment group. Absorbance was measured at 450 nm with a reference wavelength at 650 nm on EnVision (Wallac). The relative number of viable cells was expressed as the percent of cell viability.

Sphere formation. Osteosarcoma cells were plated at 5,000-10,000 cells/well in 300 μL of serum-free DMEM/F12 medium (Invitrogen), supplemented with 20 ng/mL human recombinant epidermal growth factor (EGF) (Sigma-Aldrich), 10 ng/mL human recombinant basic fibroblast growth factor (bFGF) (Invitrogen), 4 μg/mL insulin (Sigma-Aldrich), B-27® (1:50; Invitrogen), 500 units/mL penicillin (Invitrogen), and 500 μg/mL streptomycin (Invitrogen). Cells were cultured in suspension in 24-well ultra-low attachment plates (Corning). Cells were replenished with 30 μL of supplemented medium every second day. Spheres were counted on day 5 in triplicate wells. Cell culture was carried out at 37° C. in a 5% $CO_2$ humidified incubator.

Invasion assay. Invasion assays were performed by using 24-well BD BioCoat Invasion Chambers with Matrigel (Becton-Dickinson). $1×10^5$ cells, suspended in 500 μL DMEM or RPMI 1640 medium without FBS, were added to the upper chamber, and DMEM or RPMI 1640 medium with 10% FBS was added to the lower chamber. After incubation for 24 h or 36 h, the cells on the upper surface of the filter were completely removed by wiping them with cotton swabs. The filters were fixed in methanol and stained with 1% toluidine blue in 1% sodium tetraborate (Sysmex). Filters were then mounted onto slides, and cells on lower surfaces were counted. Each assay was performed in triplicate.

miRNA profiling. miRNA expression profiling was performed using miRNA microarrays manufactured by Agilent Technologies (Santa Clara, Calif.), each containing 866 human miRNAs (Agilent Technologies [http://www.chem.agilent.com/scripts/PHome,asp]). Three independently extracted RNA samples of $CD133^{high}$ and $CD133^{low}$ cells just after isolation were used for array analyses in each cell line. Labeling and hybridization of total RNA samples were performed according to the manufacturer's protocol. Microarray results were extracted using Agilent Feature Extraction software (v10.7.3.1) and analyzed using GeneSpring GX 11.0.2 software (Agilent Technologies).

Clinical samples for survival correlation studies of CD133, miR-133a, and targets of miR-133a. Osteosarcoma tissue samples were obtained by diagnostic incisional biopsy from primary sites of osteosarcoma before neoadjuvant chemotherapy at the National Cancer Center Hospital of Japan between June 1997 and September 2010. Patients older than 40 y and having primary tumors located outside the extremities were excluded. Each fresh tumor sample was cut into two pieces, one of which was immediately cryopreserved in liquid nitrogen, and the other fixed with formalin. The diagnosis of osteosarcoma and histologic subtypes were determined by certified pathologists. Only osteosarcoma samples with the osteoblastic, chondroblastic, fibroblastic, and telangiectatic histologic subtypes were included. The response to chemotherapy was classified as good if the extent of tumor necrosis was 90% or greater. For the survival correlation studies of CD133 and the targets of miR-133a, available 35 cDNA samples from cDNA library were used, while RNA from available 48 formalin-fixed, paraffin-embedded (FFPE) samples were used for the correlation study of miR-133a. The clinical information of the patients is included in Tables 7 and 10 (below). All patients provided written informed consent authorizing the collection and use of their samples for research purposes. The study protocol for obtaining clinical information and collecting samples was approved by the Institutional Review Board of the National Cancer Center of Japan.

RNA isolation and quantitative real-time RT-PCR of mRNAs and miRNAs. Total RNA was purified from cells and tumor tissues with an RNeasy Mini Kit and RNase-Free DNase Set (QIAGEN). For quantitative polymerase chain reaction (qPCR) of mRNAs, cDNA was synthesized using High-Capacity cDNA Reverse Transcription Kit (Applied Biosystems). For each qPCR reaction, equal amounts of cDNA were mixed with Platinum SYBER Green qPCR SuperMix (Invitrogen) and specific primers (Table 1). Gene expression levels were normalized by beta actin (ACTB) or glyceraldehyde 3-phosphate dehydrogenase (GAPDH). For qPCR of miRNAs, miRNA was converted to cDNA using the TaqMan MicroRNA Reverse Transcription Kit (Applied Biosystems). RNU6B small nuclear RNA was amplified as an internal control. qPCR was performed using each miRNA-specific probe included with the TaqMan MicroRNA Assay on a Real-Time PCR System 7300 and SDS software (Applied Biosystems).

TABLE 1

Sequences of primers for real-time RT-PCR analysis.

| Gene | For/Rev | Sequence (5'-Sequence-3') | SEQ ID NO: |
|---|---|---|---|
| CD133 | For | GGACCCATTGGCATTCTC | 13 |
| | Rev | CAGGACACAGCATAGAATAATC | 14 |
| Oct3/4 | For | AGTGAGAGGCAACCTGGAGA | 15 |
| | Rev | ACACTCGGACCACATCCTTC | 16 |
| Nanog | For | CAGTCTGGACACTGGCTGAA | 17 |
| | Rev | CTCGCTGATTAGGCTCCAAC | 18 |
| Sox2 | For | TGGTACGGTAGGAGCTTTGC | 19 |
| | Rev | TTTTTCGTCGCTTGGAGACT | 20 |
| ABCB1 | For | CATGCTCCCAGGCTGTTTAT | 21 |
| | Rev | GTAACTTGGCAGTTTCAGTG | 22 |
| AGCG2 | For | TGCAACATGTACTGGCGAAGA | 23 |
| | Rev | TCTTCCACAAGCCCCAGG | 24 |

TABLE 1-continued

Sequences of primers for real-time RT-PCR analysis.

| Gene | For/Rev | Sequence (5'-Sequence-3') | SEQ ID NO: |
|---|---|---|---|
| ABCC2 | For | ACAGAGGCTGGTGGCAACC | 25 |
|  | Rev | ACCATTACCTTGTCACTGTCCATGA | 26 |
| ezrin | For | CGGGACAAGTACAAGGCACTGCGGCAGATCCGG | 27 |
|  | Rev | CCGGATCTGCCGCAGTGCCTTGTACTTCCG | 28 |
| β4-integrin | For | TGACGATCTGGACAACCTCAAGCA | 29 |
|  | Rev | ATCCAATGGTGTAGTCGCTGGTGA | 30 |
| MMP13 | For | GATACGTTCTTACAGAAGGC | 31 |
|  | Rev | ACCCATCTGGCAAAATAAAC | 32 |
| CXCR4 | For | GGAGGGGATCAGTATATACA | 33 |
|  | Rev | GAAGATGATGGAGTAGATGG | 34 |
| SGMS2 | For | CAATTCCTTGCTGCTTCTCC | 35 |
|  | Rev | GCCTTTGTTTTGCTCCTCAG | 36 |
| UBA2 | For | AAAAAGGGTGTGACCGAGTG | 37 |
|  | Rev | GCATCTTCTTCCCCAAACAA | 38 |
| SNX30 | For | CCTGAACGCCTACAAGAAGC | 39 |
|  | Rev | ATGGTTCCCAGTTTGAGTGC | 40 |
| DOLPP1 | For | GAGAGGAGTGAGGCAACAGG | 41 |
|  | Rev | ACCCCAGACACAGGTTTGAG | 42 |
| DUSP11 | For | GAGACGCGACTTTTCAGGAC | 43 |
|  | Rev | GATCCAAAGGGGAAAAGCAT | 44 |
| CUL4B | For | GTTCTGGCGAAAAATCCAAA | 45 |
|  | Rev | TCGAACAATTGCAGCATCA | 46 |
| ROD1 | For | CATTCCTGGGGCTAGTGGTA | 47 |
|  | Rev | CCATCTGAACCAAGGCATTT | 48 |
| ZNF701 | For | ATCCCGTGGAGTGAAGGTC | 49 |
|  | Rev | TCTCCAGCATCACGTCTCTG | 50 |
| MAST4 | For | AGCCCATTTTTCATTTGCAC | 51 |
|  | Rev | TCGTCTGGTGTTGGTTGGTA | 52 |
| ANXA2 | For | CCTGAGCGTCCAGAAATGG | 53 |
|  | Rev | GGACTGTTATTCGCAAGCTGGTT | 54 |
| ACTB | For | CATGAAGTGTGACGTGGACA | 55 |
|  | Rev | CACGGAGTACTTGCGCTCAG | 56 |
| GAPDH | For | GACTTCAACAGCGACACCC | 57 |
|  | Rev | GCCAAATTCGTTGTCATACCA | 58 |

TABLE 2

Sequences of miRNA products

| miRNA | Sense/Antisense | Sequence (5'-Sequence-3') | SEQ ID NO: |
|---|---|---|---|
| hsa-miR-1-2 | Sense | UGGAAUGUAAAGAAGUAUUGUAU | 1 |
|  | Antisense | UACAUACUUCUUAUGUACCC | 59 |
| hsa-miR-10b | Sense | UACCCUGUAGAACCGAAUUUGUG | 2 |
|  | Antisense | ACAGAUUCGAUUCUAGGGGAAU | 60 |
| hsa-miR-133a-1 | Sense | UUUGGUCCCCUUCAACCAGCUG | 3 |
|  | Antisense | AGCUGGUAAAAUGGAACCAAAU | 61 |

TABLE 3

Sequences of LNA products

| miRNA | Sequence (5'-Sequence-3') | SEQ ID NO: |
|---|---|---|
| hsa-miR-1-2 | ACATACTTCTTTACATTCCA | 10 |
| hsa-miR-10b | ACAAATTCGGTTCTACAGGGT | 11 |
| hsa-miR-133a-1 | CAGCTGGTTGAAGGGGACCAA | 12 |

TABLE 4

Sequences of siRNAs

| Gene | Sense/Antisense | Sequence (5'-Sequence-3') | SEQ ID NO: |
|---|---|---|---|
| SGMS2 | Sense | CCACUAGAGUGGUGGAAAAdTdT | 62 |
|  | Antisense | UUUUCCACCACUCUAGUGGdTdT | 63 |
| UBA2 | Sense | GGACUGGGCUGAAGUACAAdTdT | 64 |
|  | Antisense | UUGUACUUCAGCCCAGUCCdTdT | 65 |
| SNX30 | Sense | CCGAGAAGUUUGUGGUAAAdTdT | 66 |
|  | Antisense | UUUACCACAAACUUCUCGGdTdT | 67 |
| DOLPP | Sense | CUUCCUAAUCCGAGACACAdTdT | 68 |
|  | Antisense | UGUGUCUCGGAUUAGGAAGdTdT | 69 |
| DUSP11 | Sense | CCAGAGGAUUUGCCAGAAAdTdT | 70 |
|  | Antisense | UGUGUCUCGGAUUAGGAAGdTdT | 71 |
| CUL4B | Sense | GGUGAACACUUAACAGCAAdTdT | 72 |
|  | Antisense | UUGCUGUUAAGUGUUCACCdTdT | 73 |
| ROD1 | Sense | GGGAAUGACAGCAAGAAAUdTdT | 74 |
|  | Antisense | AUUUCUUGCUGUCAUUCCCdTdT | 75 |
| ZNF701 | Sense | CCAUAAUGAAGGAGGUCUUdTdT | 76 |
|  | Antisense | AAGACCUCCUUCAUUAUGGdTdT | 77 |
| ANXA2 | Sense | UGACCAAGAUGCUCGGGAUdTdT | 78 |
|  | Antisense | AUCCCGAGCAUCUUGGUCAdTdT | 79 |
| MAST4 | Sense | GGAGGUACCUUCUUCCAAAdTdT | 80 |
|  | Antisense | UAUCAAACUUCCUCUUCUGdTdT | 81 |

Transfection with synthetic miRNAs, LNAs, and siRNAs. Synthetic hsa-miRs (Pre-miR-hsa-miR-1, -10b, -133a, and negative control (NC; Applied Biosystems, Table 2) and locked nucleic acids (LNAs) (LNA-1, -10b, -133a, and negative control, Exiqon, Table 3) were transfected into each type of cells at 30 nM each (final concentration) using DharmaFECT 1(GE Healthcare). Synthetic siRNAs (Bonac corporation, Table 4) were transfected into each type of cells at 100 nM each (final concentration) using DharmaFECT 1 (GE Healthcare). After 24 hours of incubation, cells were treated with chemotherapeutic agents for cytotoxicity assay or reseeded into invasion chambers for invasion assay.

Establishment of miR-133a stably expressing cell line. miR-133a vectors were constructed by inserting cloning sequences including the full-length of the mature microRNA sequences into the pIRES-hyg vector (Clontech). The microRNA and control vectors were transfected into freshly isolated osteosarcoma CD133$^{low}$ HOS cells by calcium phosphate co-precipitation. The transfectants were split and grown in selective medium with 200 μg/mL of hygromycin. Hygromycin-resistant colonies were chosen and expanded in medium containing 200 μg/mL of hygromycin. The sequences of miR-133a constructs were confirmed by DNA sequencing (ABI 3130 sequencer, Applied Biosystems), and microRNA overexpression was confirmed by qRT-PCR. RNU6B served as the endogenous control.

Tumor transplantation experiments. Animal experiments were performed in compliance with the guidelines of the Institute for Laboratory Animal Research, National Cancer Center Research Institute. Athymic nude mice or NOD/SCID mice (CLEA Japan) were purchased at 4 weeks of age and given at least 1 week to adapt to their new environment prior to tumor transplantation. On day 0, mice were anesthetized with 3% isoflurane and the right leg disinfected with 70% ethanol. Cells were aspirated into a 1 mL tuberculin syringe fitted with a 27-G needle. The needle was inserted through the cortex of the anterior tuberosity of the tibia with a rotating movement to avoid cortical fracture. Once the bone was traversed, the needle was inserted further to fracture the posterior cortex of the tibia. A 100 μL volume of solution containing freshly isolated $CD133^{high}$ and $CD133^{low}$ HOS-Luc ($10^2$, $10^3$, $10^4$, $10^5$ cells per site) or 143B-Luc ($1.5 \times 10^6$) was injected while slowly moving back the needle.

Monitoring tumor growth, lung metastasis, and toxicity with/without LNA-anti-miR-133a. For the assessment of tumorigenicity between $CD133^{high}$ and $CD133^{low}$ HOS-Luc cells, NOD/SCID mice were injected with D-luciferin (150 mg/kg, Promega) by intraperitoneal injection. Ten minutes later, photons from firefly luciferase were counted using the IVIS imaging system (Xenogen Corp.) according to the manufacturer's instructions. Each experimental condition included 5 animals per group and monitoring once a week. For the evaluation of LNA-anti-miR-133a administration into spontaneous lung metastasis of osteosarcoma model mice, individual mice were injected with 10 mg/kg of LNA-anti-miR-133a or saline via the tail vain. LNA were injected on following days 4, 11, 18, 25, 32 postinoculation of 143B-Luc cells. Each experimental condition included 10 animals per group. The development of subsequent lung metastasis was monitored once a week in vivo by the bioluminescent imaging described above for 5 weeks. All data were analyzed using LivingImage software (version 2.50, Xenogen). On day 36, the primary tumor and lung in 5 mice of each group were resected at necropsy for their weight, bioluminescent, and histological analyses. The blood examination, weight of whole body as well as heart, liver, and skeletal muscle, and histopathological examination were performed for the assessment of toxicity. The remaining mice were observed for their survival period.

Comprehensive collection and identification of miR-133a target mRNAs. To collect comprehensive downstream targets of miR-133a, cDNA microarray profiling from two experimental approaches were performed. First, candidate genes were collected from cDNA microarray analysis performed from collected total RNA of SaOS2 $CD133^{low}$ cells transduced with miR-133a or negative control (NC). Second, cDNA microarray analysis was performed from collected total RNA from anti-Ago2 antibody immunoprecipitation (Ago2-IP) in $CD133^{low}$ cells transduced with miR-133a or NC. Downregulated genes in the former method with 1.5 fold decrease and upregulated genes in the latter method with 2.0 fold increase were defined as candidates by reference to in silico databases TargetScanHuman 6.0 (http://www.targetscan.org/).

Luciferase reporter assays. Each fragment of 3'UTR of SGMS2 (nt 1656-1879 (binding site) of NM_152621), UBA2 (nt 2527-2654 (binding site) of NM_005499), DUSP11 (nt 1180-1572 (binding site) of NM_003584), MAST4 (nt 8017-8096 (binding site) of NM_001164664), SNX30 (nt 6659-7611 (binding site) of NA_001012944) and CDS of ANXA2 (nt 244-743 (binding site) of NM_001002857) were amplified and cloned into the XhoI and NotI sites of firefly and renilla luciferase reporter genes of a psiCHECK-2 vector (Promega). All PCR products cloned into the plasmid were verified by DNA sequencing to ensure that they were free of mutations and in the correct cloning direction. Primer sequences are listed in Table 5. For the luciferase reporter assay, HOS cells were co-transfected with 100 ng of luciferase constructs and 100 nM synthetic miR-133a molecules or control (non-targeting siRNA oligonucleotide, Qiagen). Firefly and renilla luciferase activities were measured using the Dual-Luciferase Reporter Assay (Promega) 48 h after transfection. Results were expressed as relative renilla luciferase activity (renilla luciferase/firefly luciferase).

TABLE 5

Sequences of primers for luciferase reporter assays

| Gene | For/Rev | Sequence (5'-Sequence-3') | SEQ ID NO: |
|---|---|---|---|
| SGMS2-UTR | For | GCTCGAGTAAAGCAAAAC AAAGGCATCAGC | 82 |
|  | Rev | GCGGCCGCAAGGCTTGTC ACCAATGAATGA | 83 |
| SGMS2mu-UTR | For | AAATGTCAACCATTTTGT GTAAACGATTA | 84 |
|  | Rev | AAATGGTTGACATTTCTT CATTTACCAG | 85 |
| UBA2-UTR | For | GCTCGAGTAATACCGCCT GGTATGTCTGTG | 86 |
|  | Rev | GCGGCCGCAATGCAGATG CCATTTATTTGGT | 87 |
| UBA2mu-UTR | For | TTATGTCAACCATAAATG GCATCTGCATT | 88 |
|  | Rev | TTATGGTTGACATAAGTA TAGTCGTTAT | 89 |
| SNX30-1-UTR | For | GCTCGAGTAACCCTGTTG GACAGGATTGAT | 90 |
|  | Rev | GCGGCCGCAATTTTTAAA GAAAGCATCTTTTATGG | 91 |
| SNX30mu-1-UTR | For | TCTTATCAACCCACTTCA GTCAGAAATGT | 92 |
|  | Rev | AGTGGGTTGATAAGACTG CGAACAATCA | 93 |
| DUSP11-UTR | For | GCTCGAGTAAAAACCTGT CCTGGAATTCTACC | 94 |
|  | Rev | GCGGCCGCAAGATGGCCT TTGGGTCAATAA | 95 |
| DUSP11mu-UTR | For | CTGGATCAACGAGCTGGC CTGAAAATTAC | 96 |
|  | Rev | GCTCGTTGATCCAGGTAG AATTCCAGGA | 97 |
| MAST4-UTR | For | GCTCGAGTAACTCCCCCA GCTAGGAAACAG | 98 |
|  | Rev | GCGGCCGCAAAGAGATGG GGCGGTCAGT | 99 |
| MAST4mu-UTR | For | GACGTTCAACCGCCATCC CCAGCCCCAAA | 100 |
|  | Rev | TGGCGGTTGAACGTCTCT GCCCACGTTC | 101 |
| ANXA2-UTR | For | GCTCGAGTAAGCGGGATG CTTTGAACATT | 102 |
|  | Rev | GCGGCCGCAACTCCAGCG TCATAGAGATCC | 103 |

TABLE 5-continued

Sequences of primers for luciferase reporter assays

| Gene | For/Rev | Sequence (5'-Sequence-3') | SEQ ID NO: |
|---|---|---|---|
| ANXA2mu-UTR | For | ATCAATCAACCAGGTGTGGATGAGGTCAC | 104 |
|  | Rev | ACCTGGTTGATTGATGGCTGTTTCAATG | 105 |

Immunohistochemistry. For the staining of CD133 and targets of miR-133a, slides of osteosarcoma clinical samples and xenografted tumors were prepared. Endogenous peroxidase was inhibited with 1% $H_2O_2$ (30 min). Slides were heated for antigen retrieval in 10 mM sodium citrate (pH 6.0). Subsequently, the slides were incubated with monoclonal mouse anti-human CD133/2 (1:10 dilution, Miltenyi Biotec), monoclonal mouse anti-human SGMS2 (1:50 dilution, Abeam), or isotype-matched control antibodies overnight at 4° C. Immunodetection was performed using Imm-PRESS peroxidase polymer detection reagents (Vector Laboratories) and Metal Enhanced DAB Substrate Kit (Thermo Fisher Scientific) according to the manufacturer's instructions. Staining was revealed by counter-staining with hematoxylin.

Statistical analysis. All statistical analyses were performed using SPSS software (SPSS, Inc.; Chicago, Ill.), with the exception of the significance in bar graphs, in which case analyses were performed by applying the Student's 1-test. Differences in the CD133 expression among different clinicopathological data were analyzed by Chi-square ($\chi^2$) test. Cases with ΔCt lower than the mean value were classified as having high CD133 expression, while cases with ΔCt higher than the mean value were classified as having low CD133 expression. The Kaplan-Meier method and the log-rank test were used to compare the survival of patients with CD133$^{high}$ and CD133$^{low}$ primary tumors. Survival period was defined as the time from diagnosis until death whereas living patients were censored at the time of their last follow-up. For the calculation of differences in the expressions of miR-133a and its targets, the same procedure was applied. In all these analyses, a P value of 0.05 or less was considered to be a significant difference.

EXAMPLE 1

A Small Subset of Cells of Osteosarcoma Cell Line Expresses CD 133

Osteosarcoma cell lines SaOS2, HOS, U2OS, MNNG/HOS, MG63, 143B, and HuO9 were screened for markers of mesenchymal stem cells or neural stem cells that have been considered as the origin of sarcoma. Basu-Roy, U et al. (2011) Oncogene 31:2270-82; Kuhn, N Z et al, (2010) J. Cell. Physiol. 222:268-77, As a result, CD133, the structural homolog of prominin-1, was found in all cell lines at a small population ranging from 0.04% to 8.47%, whereas CD44 was found in a large population (FIG. 1). SaOS2, MNNG/HOS, and HOS were found to be particularly strong in their expression of CD133 (8.47, 8.13, and 7.69 percent, respectively).

Single-cell proliferation of freshly isolated cell population was observed using PKH dye, which is a fluorescent dye that binds to cell membranes and segregates in daughter cells after each cell division. Normally, PKH concentration decreases with each cell division, so that quiescent cells remain PKH$^{high}$ and dividing cells become progressively PKH$^{low}$. Moreover, normally PKH67 dye is distributed equally between daughter cells, whereas rapidly dividing cells, e.g., cancer cells, exhibit asymmetric division.

Figure 2:
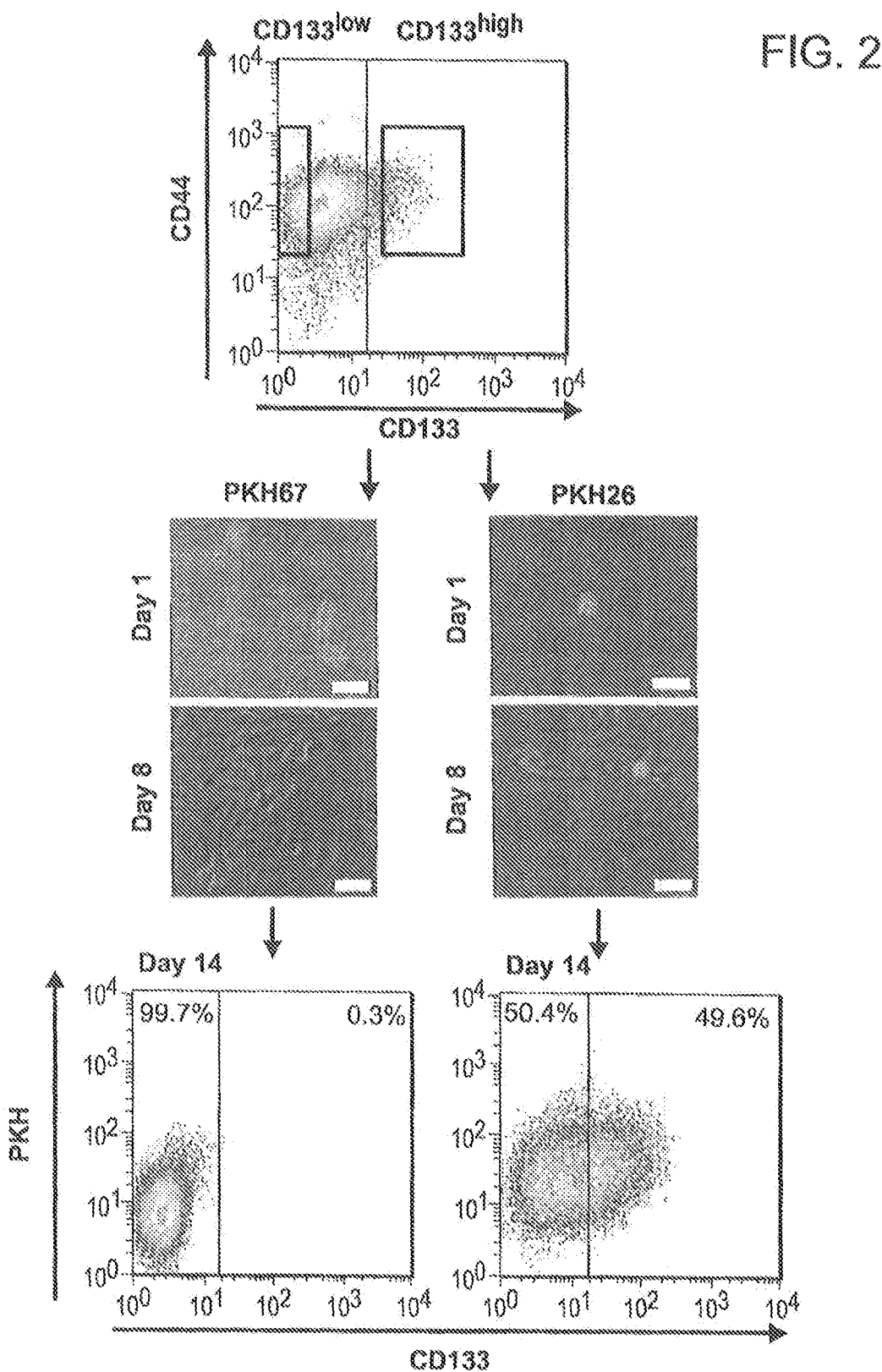
FIG. 2 is a collage comprising a FACS analysis depicting selection of $CD133^{high}$ and $CD133^{low}$ SaOS2 cells (top panel); four photomicrographs depicting asymmetric cell division in the $CD133^{high}$ population at day 1 and day 8 (middle panel); and two FACS analyses by PKH staining for each population at day 14 (bottom panel). Scale bars, 50 mm.

The CD133$^{high}$ cell population generated both CD133$^{high}$ and CD133$^{low}$ populations with different proliferative fates: one that is quiescent (PKH$^{high}$) and another that divides actively (PKH$^{low}$). A single PKH26$^{high}$ cell of CD133$^{high}$ fraction showed asymmetric division; a small number of PKH26$^{high}$ cells, presenting as dormant cells, were observed surrounded by PKH26$^{low}$ cells on day 8, which were identified as a fraction with both CD133$^{high}$ and CD133$^{low}$ cells on FACS analysis. On the other hand, a single PKH67$^{high}$ cell of CD133$^{low}$ SaOS2 fraction showed symmetric division; a colony with PKH67$^{low}$ cells was observed, which was identified as a CD133$^{low}$ fraction in FACS analysis two weeks after isolation (FIG. 2). No difference in cell division according to the expression of CD44 was observed.

Figure 3:
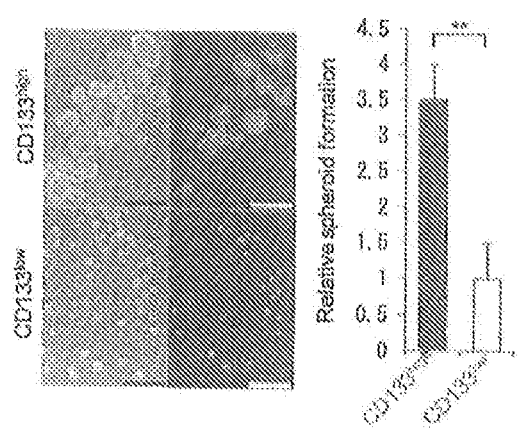
FIG. 3 is a group of four photomicrographs and a bar graph depicting sphere-formation assays in freshly isolated $CD133^{high}$ and $CD133^{low}$ HOS-GFP cells. Photos were taken on day 5 and the numbers of spheres in each well were counted (n=3 per group, **P<0.01). Scale bar, 200 μm.

Further examinations were performed to identify other phenotypes of CD133$^{high}$ and CD133$^{low}$ population. A total of $5 \times 10^3$ CD133$^{high}$ and CD133$^{low}$ cells were sorted and cultured immediately under conditions of serum-free, growth factor-supplemented anchorage-independent environment. Within two weeks of culture, more osteosarcoma spheres were observed from CD133$^{high}$ cells than CD133$^{low}$ cells (FIG. 3).

EXAMPLE 2

Figure 4:
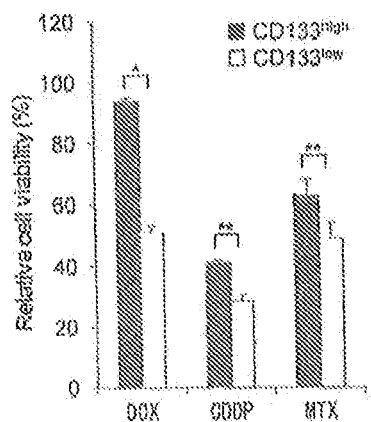
FIG. 4 is a bar graph depicting drug sensitivity of $CD133^{high}$ and $CD133^{low}$ SaOS2 cell populations. Relative viable cells to doxorubicin (DOX, 0.03 μM), cisplatin (CDDP, 2.5 μM), and methotrexate (MTX, 0.32 μM) were analyzed (n=3 per group, *P<0.05, **P<0.01).
Figure 6:
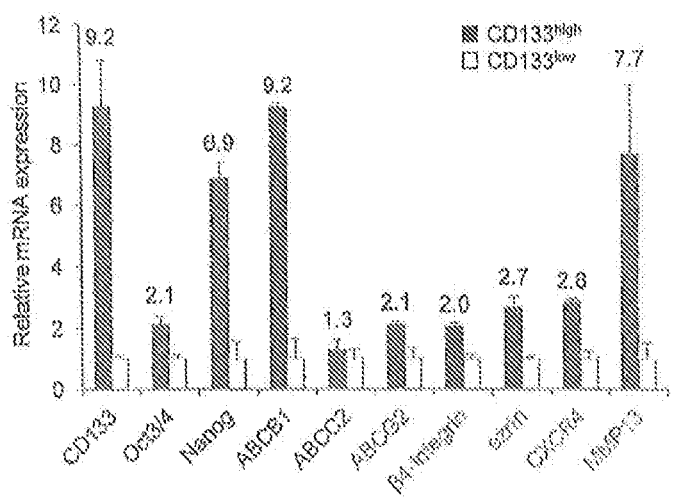
FIG. 6 is a graph depicting quantitative polymerase chain reaction (qPCR) analysis of stem cell-associated, multiple drug-resistant transporters and metastasis-associated genes of $CD133^{high}$ and $CD133^{low}$ SaOS2 cell populations. β-actin was used as an internal control.
Figure 7:
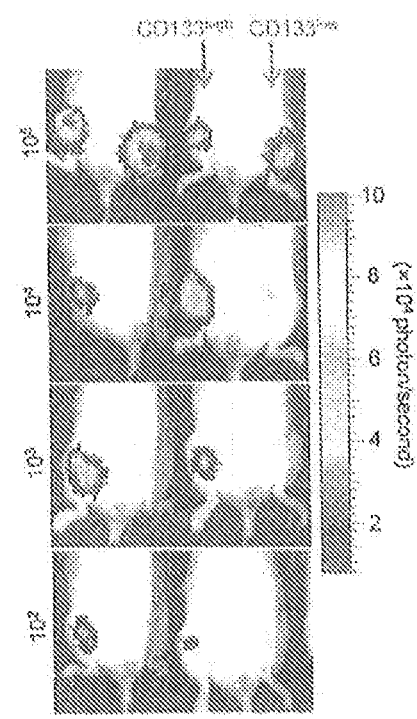
FIG. 7 is a group of eight photographic images depicting tumorigenicity of CD133$^{high}$ and CD133$^{low}$ HOS-luc cell populations in mice. Luminescence of the tumors xenografted with CD133$^{high}$ (animals' right thighs) and CD133$^{low}$ (animals' left thighs) HOS-luc cells are identified by in vivo imaging system (IVIS). CD133$^{high}$ population formed tumors with as few as 100 cells (n=5 per group).
Figure 8:
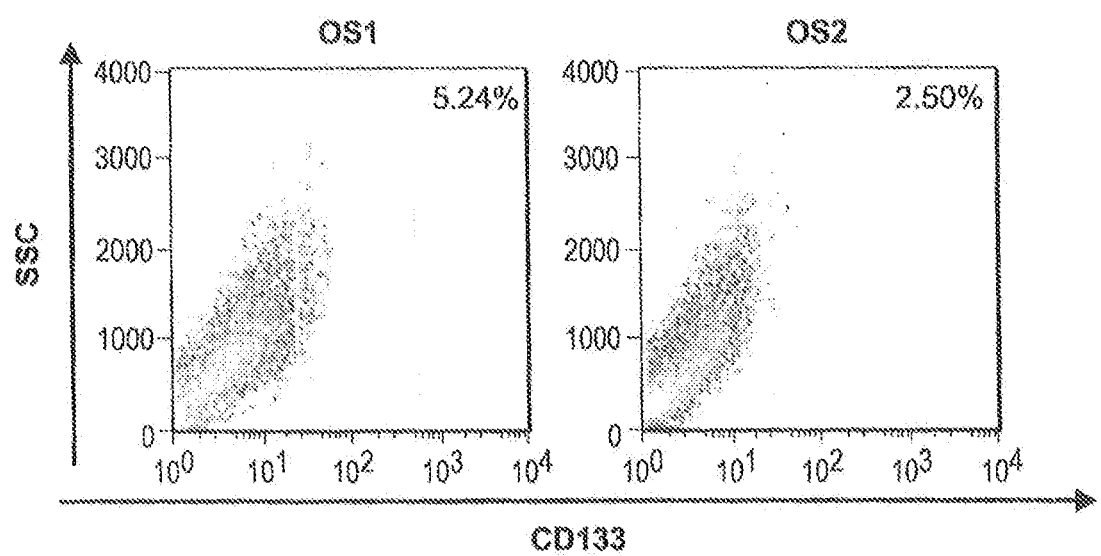

CD133$^{high}$ Cells Exhibit Increased Drug Resistance, Invasiveness, and Tumorigenesis Since drug resistance is one of the important properties of TICs, populations of CD133$^{high}$ and CD133$^{low}$ cells were observed in the treatment condition with doxorubicin (DOX), cisplatin (CDDP), and methotrexate (MTX), which are standard chemotherapeutics against osteosarcoma, CD133$^{high}$ cells were more resistant to these chemotherapeutics than CD133$^{low}$ cells (FIG. 4). Furthermore, CD133$^{high}$ cells exhibited higher capability of invasion than CD133$^{low}$ cells (FIG. 5). qRT-PCR of mRNA from freshly isolated CD133$^{high}$ and CD133$^{low}$ cells revealed that CD133$^{high}$ SaOS2 cells expressed enhanced levels of Oct3/4, Nanog, and Sox-2, which are transcription factors that play a critical role in maintenance of self-renewal and pluripotency of embryonic stem cells as well as CSCs or TICs (Livings, P P et al. (2009) Cancer Res. 69:5648-55; Basu-Roy U et al. (2011) Oncogene 31:2270-82); multidrug resistance transporter genes ABCB1, ABCC2, ABCG2; and metastasis-associated genes β4-integrin, ezrin, MMP-13 , and CXCR4 (Tang, N et al. (2008) Clin. Orthop. Relat. Res. 466:2114-30; Osaki, M et al. (2011) Mol. Ther. 19:1123-30) (FIG. 6). Most importantly, the CD133$^{high}$ HOS fraction showed stronger tumorigenicity in vivo than the CD133$^{low}$ HOS fraction; CD133$^{high}$ cells could form tumors from as few as 100 cells, whereas CD133$^{low}$ cells could not (FIG. 7). Results are also shown in Table 6.

TABLE 6

Tumor development in vivo using osteosarcoma CD133$^{high}$ and CD133$^{low}$ populations alone

| Cell Type | Tumor Incidence | Cell Number |
|---|---|---|
| CD133$^{high}$ | 5/5 | 100,000 |
|  | 5/5 | 10,000 |
|  | 5/5 | 1,000 |
|  | 4/5 | 100 |

TABLE 6-continued

Tumor development in vivo using osteosarcoma CD133$^{high}$ and CD133$^{low}$ populations alone

| Cell Type | Tumor Incidence | Cell Number |
|---|---|---|
| CD133$^{low}$ | 4/5 | 100,000 |
| | 1/5 | 10,000 |
| | 1/5 | 1,000 |
| | 1/5 | 100 |

EXAMPLE 3

Figure 8:
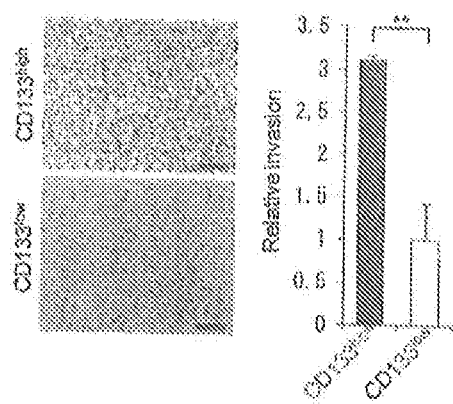
FIG. 8 is a pair of FACS analyses depicting CD133$^{high}$ cell populations in clinical osteosarcoma specimens.
Figure 9:
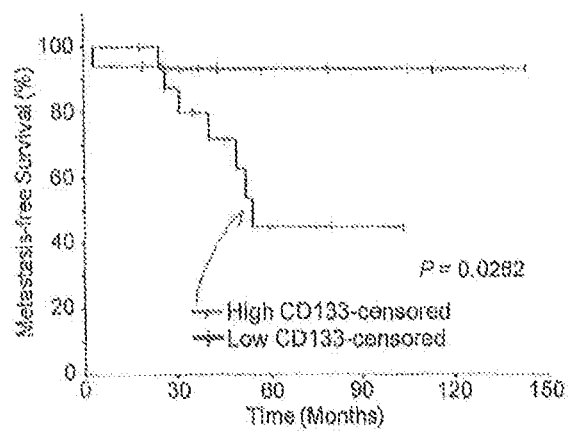
FIG. 9 is a graph depicting metastasis-free survival for osteosarcoma patients based on CD133 expression. Patients with high expression of CD133 had a median metastasis-free survival of less than 60 months (n=35, log-rank test, P=0.0262).

High-Level Expression of CD133 Messenger RNA is a Marker for Poor Survival Rates of Osteosarcoma Patients To evaluate the clinical importance of CD133, cell lines established from fresh human osteosarcoma biopsies were analyzed by flow cytometer and found to contain CD133$^{high}$ population at a rare frequency <10% (FIG. 8). Furthermore, a clinical study of 35 osteosarcoma patients revealed that high expression levels of CD133 messenger RNA (mRNA) correlated with significantly worse overall survival rates of osteosarcoma patients (log-rank lest, P=0.0262). Results are shown in FIG. 9 and Table 7.

TABLE 7

Uni- and multivariate analyses and the relationship between clinicopathologic variables and CD133 expression in 35 cases

| Variable | Number of cases | CD133 Low | CD133 High | Correlation (CD133) $\chi^2$ (P value) |
|---|---|---|---|---|
| Age (years) | | | | 0.120 |
| 0-10 | 7 | 6 | 1 | |
| 11-20 | 25 | 11 | 14 | |
| 21+ | 3 | 1 | 2 | |
| Gender | | | | 0.164 |
| Male | 23 | 14 | 9 | |
| Female | 12 | 4 | 8 | |
| Site | | | | 0.319 |
| Femur | 21 | 12 | 9 | |
| Tibia | 9 | 5 | 4 | |
| Humerus | 2 | 1 | 1 | |
| Other | 3 | 0 | 3 | |
| Histology | | | | 0.394 |
| Osteoblastic | 16 | 9 | 7 | |
| Chandroblastic | 6 | 4 | 2 | |
| Fibroblastic | 2 | 0 | 2 | |
| Other, NA* | 11 | 5 | 6 | |
| Metastasis at diagnosis | | | | 0.045 |
| Present | 4 | 0 | 4 | |
| Absent | 31 | 18 | 13 | |
| Neoadjuvant chemotherapy | | | | 0.425 |
| MTX + DOX/CDDP | 21 | 10 | 11 | |
| IFO + DOX/CDDP | 13 | 8 | 5 | |
| Other | 1 | 0 | 1 | |
| Response to neoadjuvant chemotherapy | | | | 0.088 |
| Good (necrosis > 90%) | 11 | 6 | 5 | |
| Poor (necrosis < 90%) | 20 | 12 | 8 | |
| NA* | 4 | 0 | 4 | |
| CD133 mRNA expression | | | | |
| High | 17 | 0 | 17 | |
| Low | 18 | 18 | 0 | |

Figure 10:
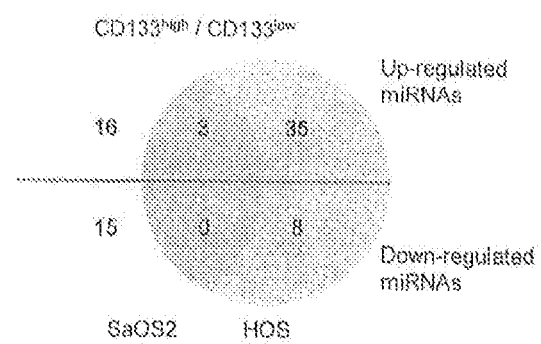
FIG. 10 is a Venn diagram depicting upregulated and downregulated miRNAs in CD133$^{high}$ and CD133$^{low}$ cells of SaOS2 and HOS.
Figure 11:
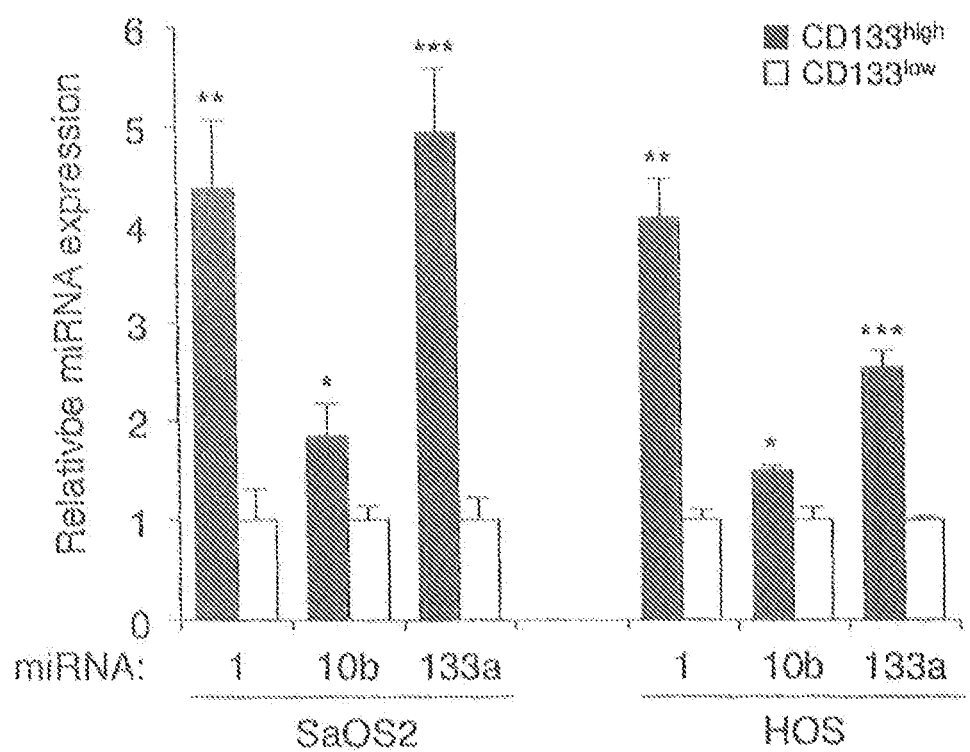
FIG. 11 is a bar graph depicting upregulated miR-1, miR-10b, and miR-133a in CD133$^{high}$ populations of SaO2 and HOS cells compared to CD133$^{low}$ population (*P<0.05, P<0.01, *P<0.001).

EXAMPLE 4 miR-1, miR-10b, and miR-133a are Upregulated in CD133$^{high}$ Cells Compared to CD133$^{low}$ Cells miRNA expression profiling has been reported to be a useful diagnostic and prognostic tool, and many studies have indicated that certain miRNAs act as either an oncogene or a tumor suppressor. Croce. C M (2009) *Nat. Rev. Genet*, 10:704-10. in order further to characterize the molecular mechanism underlying the CD133$^{high}$ and CD133$^{low}$ phenotypes, miRNA profiling of isolated CD133$^{high}$ and CD133$^{low}$ osteosarcoma SaOS2 and HOS cells was performed using microarray analysis containing 866 sequence-validated human miRNAs. Results, shown in FIG. 10 and Table 8, revealed that 3 miRNAs were upregulated at >2-fold changes in CD133$^{high}$ cells compared to CD133$^{low}$ cells. A second round of qPCR validation study revealed miR-1, miR-10b, and miR-133a were consistent with the microarray data (FIG. 11).

TABLE 8 microRNA expression profile of CD133$^{high}$ versus CD133$^{low}$ osteosarcoma cells

| miRNA | Fold change (SaOS2 CD133$^{high}$ vs CD133$^{low}$) | Regulation | Fold change (HOS CD133$^{high}$ vs CD133$^{low}$) | Regulation |
|---|---|---|---|---|
| Commonly upregulated miRNAs in SaOS2 and HOS with >2 fold change in CD133$^{high}$ cells compared to CD133$^{low}$ cells | | | | |
| hsa-miR-1 | 7.23 | up | 3.81 | up |
| hsa-miR-500* | 5.39 | up | 3.99 | up |
| hsa-miR-660 | 2.09 | up | 2.05 | up |
| Upregulated miRNAs in SaOS2 with >2 fold change in CD133$^{high}$ cells compared to CD133$^{low}$ cells | | | | |
| hsa-miR-551b | 9.49 | up | | |
| hsa-miR-30e | 9.19 | up | | |
| hsa-miR-148b | 8.26 | up | | |
| hsa-miR-193a-3p | 7.77 | up | | |
| hsa-miR-1 | 7.23 | up | | |
| hsa-miR-221* | 6.76 | up | | |
| hsa-miR-24-1* | 6.36 | up | | |
| hsa-miR-1825 | 5.78 | up | | |
| hsa-miR-500* | 5.39 | up | | |
| hsa-miR-92a-2* | 4.36 | up | | |
| hsa-miR-1202 | 3.39 | up | | |
| hsa-miR-424 | 3.23 | up | | |
| hsa-miR-19b-2* | 2.87 | up | | |
| hsa-miR-29c | 2.42 | up | | |
| hsa-miR-494 | 2.37 | up | | |
| hsa-miR-10b | 2.16 | up | | |
| hsa-miR-374a | 2.11 | up | | |
| hsa-miR-660 | 2.09 | up | | |
| hsa-miR-30e* | 2.03 | up | | |
| Downregulated miRNAs in SaOS2 with <2 fold change in CD133$^{high}$ cells compared to CD133$^{low}$ cells | | | | |
| hsa-miR-1281 | 9.45 | down | | |
| hsa-miR-195 | 6.56 | down | | |
| hsa-miR-129-5p | 5.74 | down | | |
| hsa-miR-129-3p | 4.98 | down | | |
| hsa-miR-183 | 4.89 | down | | |
| hsa-miR-1305 | 4.76 | down | | |
| hsa-miR-1275 | 4.65 | down | | |
| hsa-miR-484 | 4.55 | down | | |
| hsa-miR-1268 | 4.51 | down | | |
| hsa-miR-186 | 4.51 | down | | |
| hsa-miR-181a* | 4.46 | down | | |
| hsa-miR-744* | 2.72 | down | | |
| hsa-miR-96 | 2.65 | down | | |
| hsa-miR-142-3p | 2.35 | down | | |
| hcmv-miR-US25-2-5p | 2.31 | down | | |

TABLE 8-continued microRNA expression profile of CD133$^{high}$ versus CD133$^{low}$ osteosarcoma cells

| miRNA | Fold change (SaOS2 CD133$^{high}$ vs CD133$^{low}$) | Regulation | Fold change (HOS CD133$^{high}$ vs CD133$^{low}$) | Regulation |
|---|---|---|---|---|
| Upregulated miRNAs in HOS with >2 fold change in CD133$^{high}$ cells compared to CD133$^{low}$ cells | | | | |
| hsa-miR-1181 | | | 12.78 | up |
| hsa-miR-133b | | | 7.22 | up |
| hsa-miR-532-5p | | | 7.10 | up |
| hsa-miR-338-3p | | | 6.30 | up |
| hsa-miR-9 | | | 5.95 | up |
| hsa-miR-34c-5p | | | 5.37 | up |
| hsa-miR-378* | | | 5.26 | up |
| hsa-miR-181a* | | | 5.04 | up |
| hsa-miR-145* | | | 4.97 | up |
| hsa-miR-1271 | | | 4.97 | up |
| hsa-miR-362-3p | | | 4.67 | up |
| hsa-miR-152 | | | 4.63 | up |
| hsa-miR-663 | | | 4.46 | up |
| hsa-miR-9* | | | 4.15 | up |
| hsa-miR-340 | | | 4.10 | up |
| hsa-miR-744 | | | 4.07 | up |
| hsa-miR-500* | | | 3.99 | up |
| hsa-miR-1 | | | 3.81 | up |
| hsa-miR-1305 | | | 3.33 | up |
| hsa-miR-744* | | | 3.11 | up |
| hsa-miR-629 | | | 2.88 | up |
| hsa-miR-629* | | | 2.71 | up |
| hsa-miR-145 | | | 2.55 | up |
| hsa-miR-1246 | | | 2.47 | up |
| hsa-miR-21* | | | 2.39 | up |
| hsa-miR-450a | | | 2.35 | up |
| hsa-miR-425* | | | 2.31 | up |
| hsa-miR-148a | | | 2.30 | up |
| hsa-let-7f-1* | | | 2.26 | up |
| hsa-miR-301b | | | 2.21 | up |
| hsa-miR-1826 | | | 2.15 | up |
| hsa-miR-128 | | | 2.15 | up |
| hsa-miR-378 | | | 2.14 | up |
| hsa-miR-126 | | | 2.13 | up |
| hsa-miR-598 | | | 2.06 | up |
| hsa-miR-1915 | | | 7.05 | up |
| hsa-miR-660 | | | 2.05 | up |
| hsa-miR-933 | | | 2.02 | up |
| Downregulated miRNAs in HOS with <2 fold change in CD133$^{high}$ cells compared to CD133$^{low}$ cells | | | | |
| hsv1-miR-H6 | | | 4.60 | down |
| hsa-miR-1539 | | | 4.02 | down |
| hsa-miR-483-3p | | | 3.76 | down |
| hsa-miR-328 | | | 3.72 | down |
| hsa-miR-132* | | | 3.67 | down |
| hsa-miR-129* | | | 3.66 | down |
| hsa-miR-548c-5p | | | 3.13 | down |
| hsa-miR-1825 | | | 2.05 | down | hsa, Homo sapiens.

miRNA and miRNA* are the two strands of the double-stranded RNA product of dicer processing of the stem loop precursor miRNA. miRNA is the "guide" strand that eventually enters RISC, and miRNA* is the other "passenger" strand. The level of miRNA* present in the cell is low (≤15% relative to the corresponding miRNA). In cases where there is a higher proportion of passenger strand present in the cell, the nomenclature miRNA-3p/miRNA-5p is used instead of miRNA/miRNA*. miRNA-3p is the miRNA derived from the 3' arm of the precursor miRNA, and miRNA-5p is the miRNA derived from the 5' arm of the precursor miRNA.

EXAMPLE 5

Figure 12:
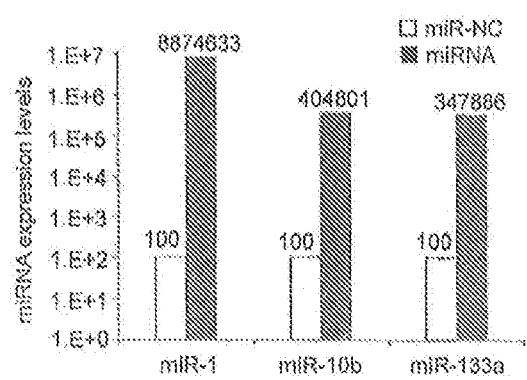
FIG. 12 is a graph depicting the expression of miR-1, miR-10b, and miR-133a in CD133$^{low}$ SaOS2 cells transfected with miRNA oligonucleotides compared to CD133$^{low}$ SaOS2 cells transfected with miR-NC (negative control) oligonucleotides (log scale, n=3 per group, *P<0,05, P<0.01, *P<0.001)
Figure 13:
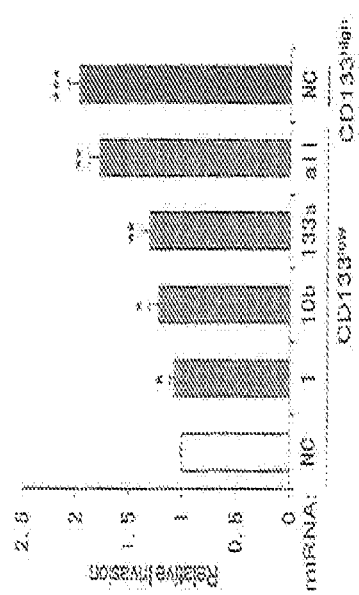
FIG. 13 is a graph depicting invasion assays in purified CD133$^{low}$ cells transfected with miR-1, miR-10b, and miR-133a or NC oligonucleotides (*P<0.05, P<0.01, *P<0.001).
Figure 14:
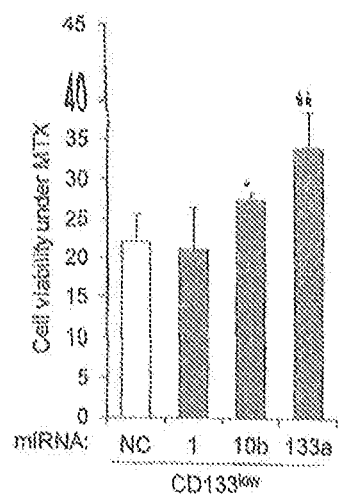
FIG. 14 is a graph depicting drug resistance in CD133$^{low}$ cells transfected with miR-1, miR-10b, miR-133a, or miR-NC oligonucleotides (MTX, methotrexate at (1.22 mM; *P<0.05, **P<0.01).
Figure 15:
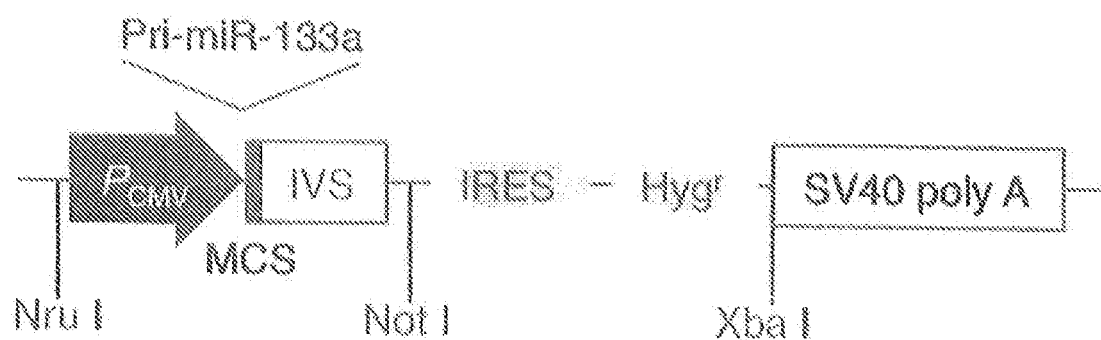
FIG. 15 is a schematic representation of plasmid vectors utilized for stable overexpression of miR-133a in CD133$^{low}$ cells. NruI, NotI, XbaI: restriction endonuclease sites; P$_{CMV}$, cytomegalovirus promoter; MCS, multiple cloning site; IVS, intervening sequence; IRES, internal ribosome entry site; Hyg$^r$, hygromycin resistance gene; SV40 poly A, SV40 polyA tail.
Figure 16:
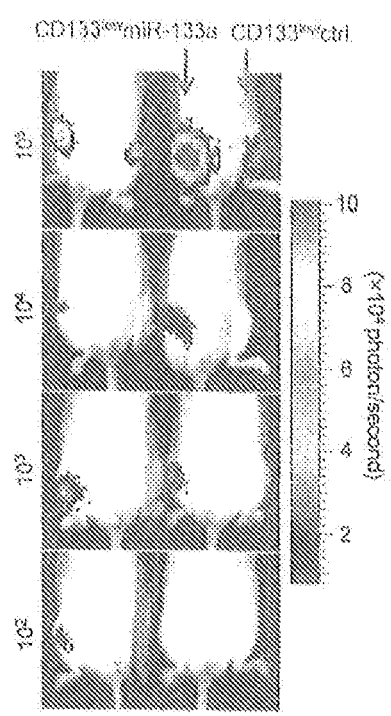
FIG. 16 comprises four pairs of photographic images depicting tumorigenicity of CD133$^{low}$ HOS-luc cells stably expressing miR-133a (right legs) compared to control CD133$^{low}$ HOS-luc cells (left legs). Each site was injected with the indicated number of cells ($10^2$-$10^5$); luminescent evaluation was performed 90 days post injection.

Transfection of CD133$^{low}$ Cells with miR-133 Confers Properties Associated with CD133$^{high}$ Cells, and High Expression of miR-133a is Correlated with Poor Clinical Prognosis To determine whether these miRNAs can inhibit these phenotypes of osteosarcoma tumor-initiating cells, expression levels of miR-1, miR-10b, and miR-133a were manipulated in CD133$^{low}$ cells (FIG. 12). These miRNAs, especially miR-133a, enhanced the invasiveness of CD133$^{low}$ cells compared to miR-NC (negative control) oligonucleotides (FIG. 13). Interestingly, transfection of all these miRNAs dramatically enhanced the invasion of CD133$^{low}$ cells (FIG. 13). Cell proliferation and drug resistance were slightly enhanced in CD133$^{low}$ cells by miR-133 transfection (FIG. 14). Stable overexpressing miR-133a HOS CD133$^{low}$ cells (FIG. 15) showed stronger (>2-fold) ability to form spheres than control CD133$^{low}$ cells under anchorage serum-free environment and could develop tumors with as few as 100 cells in vivo whereas control CD133$^{low}$ cells could not (FIG. 16 and Table 9).

TABLE 9

Tumor development in vivo using osteosarcoma CD133$^{low}$ populations stably overexpressing miR-133a

| Cell Type | Tumor Incidence | Cell Number |
|---|---|---|
| CD133$^{low}$ miR-133a | 5/5 | 100,000 |
|  | 4/4 | 10,000 |
|  | 5/5 | 1,000 |
|  | 2/5 | 100 |
| CD133$^{low}$ EV[1] | 5/5 | 100,000 |
|  | 1/4 | 10,000 |
|  | 0/5 | 1,000 |
|  | 0/5 | 100 |
| CD133$^{low}$ CDDP[2] | 5/5 | 100 |
| CD133$^{low}$ Saline[3] | 0/5 | 100 |

[1]EV, empty vector.
[2]CDDP, cells treated with CDDP.
[3]Saline, cells treated with saline.

Figure 17:
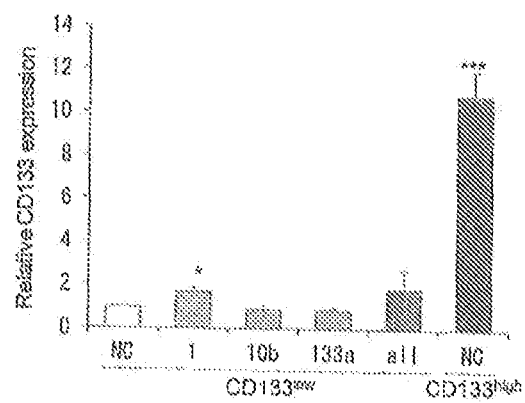
FIG. 17 is a graph depicting expression of CD133 messenger RNA (mRNA) in CD133$^{low}$ SaOS2 cells transfected with miR-1, miR-10b, and miR-133a oligonucleotides. Alteration of these miRNAs did not alter CD133 expression levels. Comparison is also made to CD133$^{high}$ cells transfected with miR-NC (negative control) oligonucleotide (n=3 per group).
Figure 18:
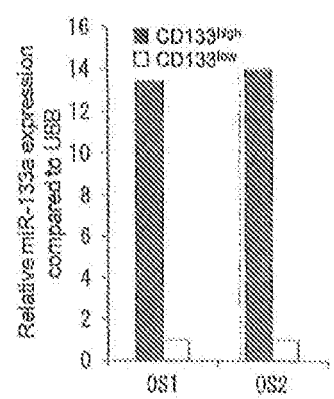
FIG. 18 is a graph depicting expression of miR-133a in CD133$^{high}$ populations of freshly resected patient biopsies.

Transfection of miR-133a also increased messenger RNA (mRNA) levels of the molecules that were upregulated in CD133$^{high}$ cells (see FIG. 6) but not CD133 mRNA, suggesting that miR-133a does not affect the expression of the molecules on the upstream pathway of CD133 (FIG. 17). These results revealed that miR-133a is a candidate miRNA that can regulate the phenotypes of osteosarcoma TICs. Indeed, the expression of miR-133a was also high in the CD133$^{high}$ fraction of osteosarcoma biopsies (FIG. 18), and high expression of miR-133a was significantly correlated with poor prognosis of patients (Table 10).

TABLE 10

Uni- and multivariate analyses and the relationship between clinicopathologic variables and miR-133a expression in 48 cases

| Variable | Number of cases | miR-133a Low | miR-133a High | Correlation (CD133)$\chi^2$ (P value) |
|---|---|---|---|---|
| Age (years) |  |  |  | 0.228 |
| 0-10 | 9 | 9 | 0 |  |
| 11-20 | 30 | 23 | 7 |  |
| 21+ | 9 | 8 | 1 |  |

TABLE 10-continued

Uni- and multivariate analyses and the relationship between clinicopathologic variables and miR-133a expression in 48 cases

| Variable | Number of cases | miR-133a Low | miR-133a High | Correlation (CD133)$\chi^2$ (P value) |
|---|---|---|---|---|
| Gender | | | | 1.000 |
| Male | 31 | 26 | 5 | |
| Female | 17 | 14 | 3 | |
| Site | | | | 0.566 |
| Femur | 26 | 22 | 4 | |
| Tibia | 16 | 14 | 2 | |
| Humerus | 2 | 1 | 1 | |
| Other | 4 | 3 | 1 | |
| Histology | | | | 0.142 |
| Osteoblastic | 25 | 23 | 2 | |
| Chondroblastic | 7 | 6 | 1 | |
| Fibroblastic | 2 | 2 | 0 | |
| Other, NA* | 14 | 9 | 5 | |
| Metastasis at diagnosis | | | | 0.330 |
| Present | 7 | 5 | 2 | |
| Absent | 41 | 35 | 6 | |
| Neoadjuvant chemotherapy | | | | 0.902 |
| MTX + DOX/CDDP | 29 | 24 | 5 | |
| IFO + DOX/CDDP | 18 | 15 | 3 | |
| Other | 1 | 1 | 0 | |
| Response to neoadjuvant chemotherapy | | | | 0.173 |
| Good (necrosis > 90%) | 17 | 16 | 1 | |
| Poor (necrosis < 90%) | 26 | 21 | 5 | |
| NA* | 5 | 3 | 2 | |
| miR-133a expression | | | | |
| High | 8 | 0 | 8 | |
| Low | 40 | 40 | 0 | |

EXAMPLE 6

Figure 19:
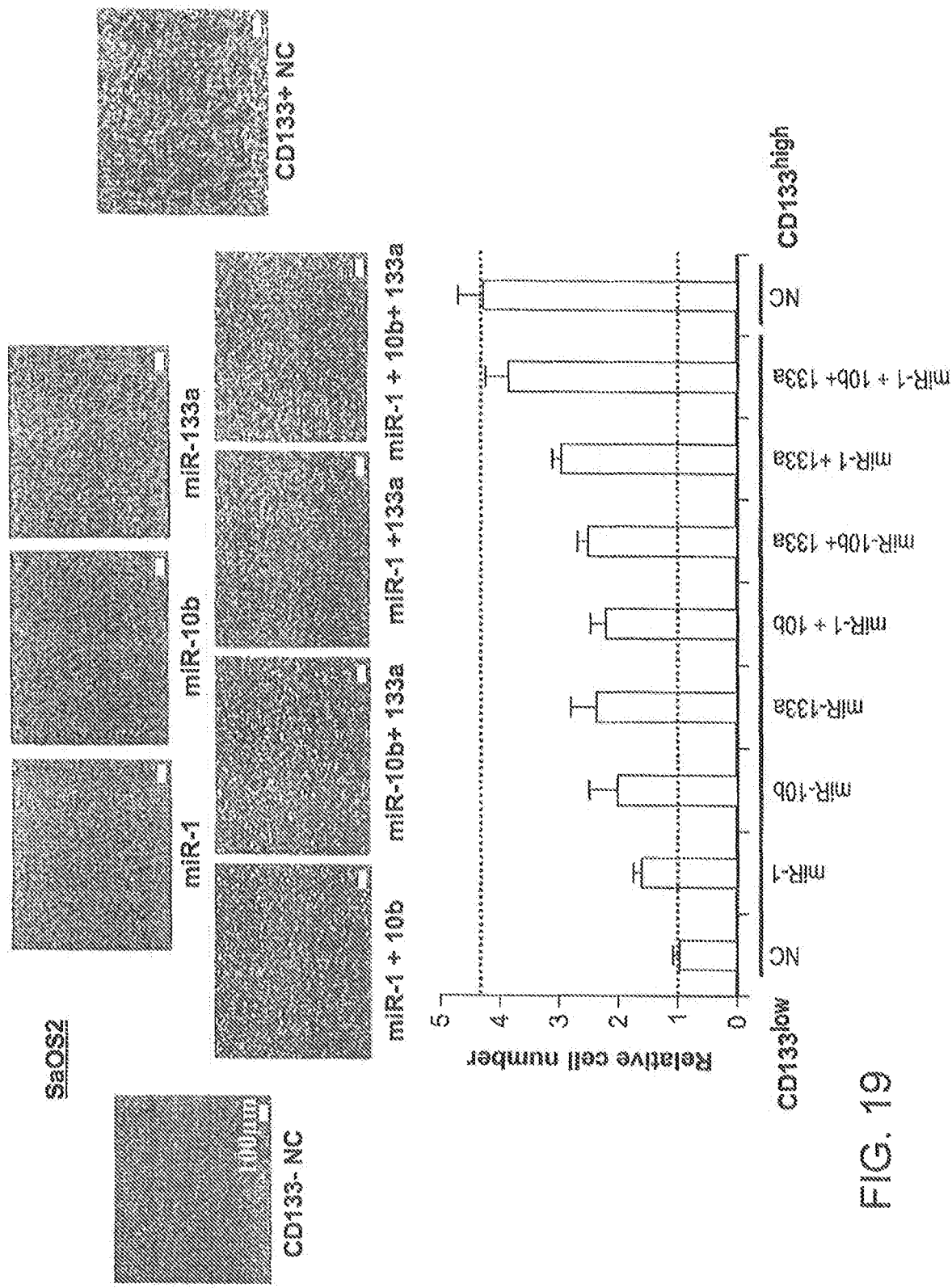
FIG. 19 is a series of photomicrographs and a related bar graph depicting the effects of individual miRNAs, and various combinations of the miRNAs, on invasiveness of CD133$^{low}$ SaOS2 cells transfected with the indicated miRNAs. For the purposes of comparison data is also presented for CD133$^{high}$ SaOS2 cells. NC, negative control.

Transfection of CD133$^{low}$ SaOS2 Cells with miRNAs Results in Increased Proliferation CD133$^{low}$ SaOS2 cells were isolated by cell sorting and then transfected with negative control (NC) RNA, miR-1 alone, miR-10b alone, miR-133a alone, miR-1 plus mirR-10b, mirR-10b plus miR-133a, miR-1 plus miR-133a, or miR-1 plus miR-10b plus miR-133a. CD133$^{high}$ cells also were isolated by cell sorting and then transfected with negative control (NC) RNA. Each population of cells was separately maintained in tissue culture for 3-7 days and then studied with a light microscope to assess cell proliferation. Results are shown in FIG. 19. As is evident from FIG. 19, CD133$^{low}$ SaOS2 cells transfected with miR-1 alone, miR-10b alone, miR-133a alone, miR-1 plus mirR-10b, mirR-10b plus miR-133a, miR-1 plus miR-133a, or miR-1 plus miR-10b plus miR-133a proliferated to a greater extent than did CD133$^{low}$ SaOS2 cells transfected with negative control RNA. CD133$^{low}$ SaOS2 cells transfected with miR-1 plus miR-10b plus miR-133a proliferated to nearly the same extent as CD133$^{high}$ cells transfected with negative control RNA. The effects of the combinations were at least additive.

Figure 20:
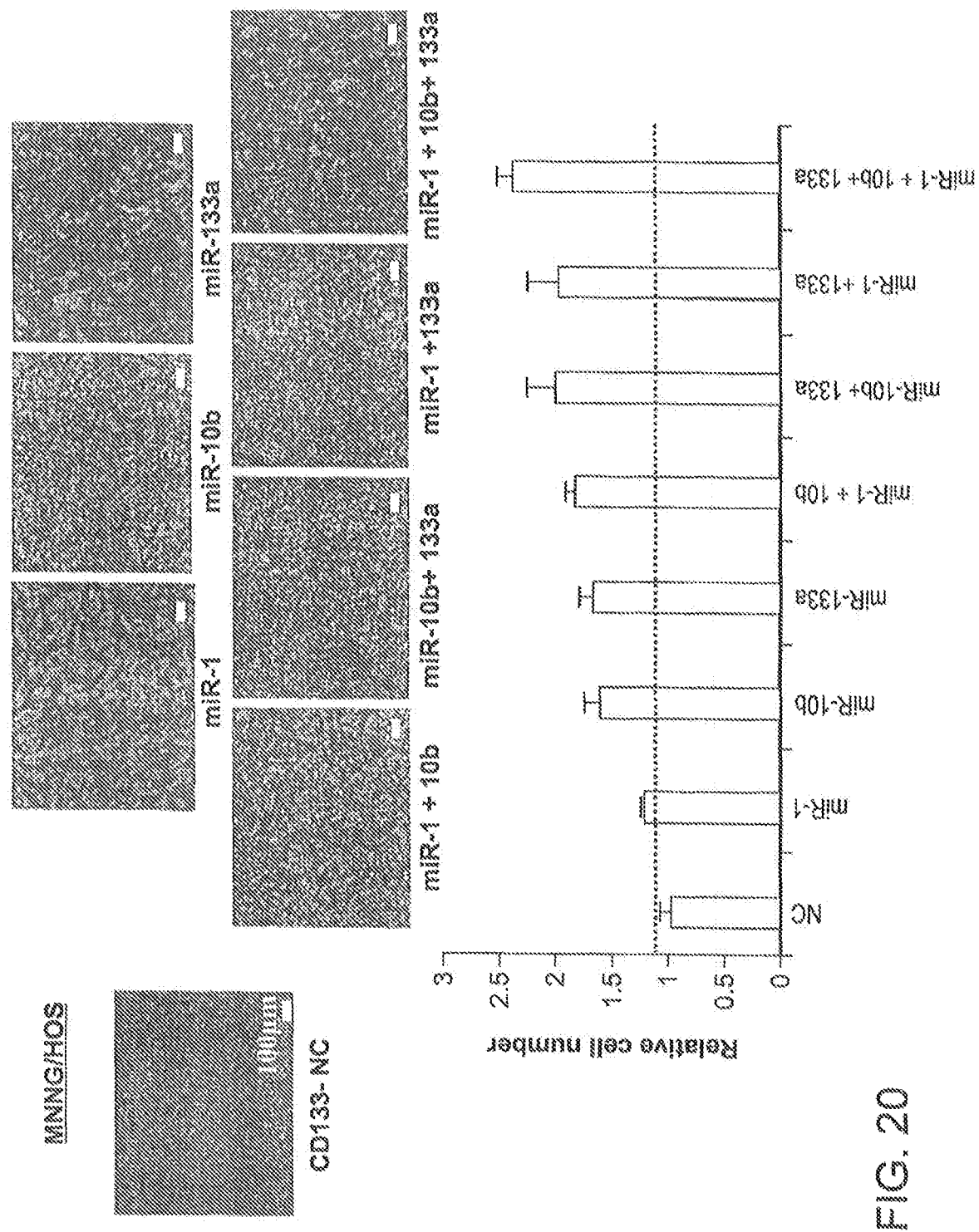
FIG. 20 is a series of photomicrographs and related bar graph depicting the effects of individual miRNAs, and various combinations of the miRNAs, on invasiveness of CD133$^{low}$ MNNG/HOS cells transfected with the indicated miRNAs. NC, negative control.

Similar results were obtained in an experiment with MNNG/HOS cells in place of SaOS2 cells (FIG. 20).

EXAMPLE 7

Figure 21:
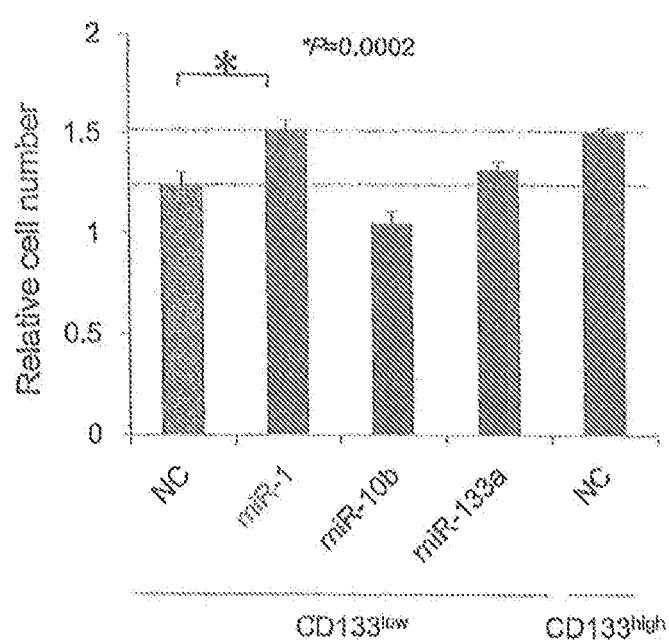
FIG. 21 is a bar graph depicting proliferation of non-transfected CD133$^{high}$ SaOS2 cells and CD133$^{low}$ SaOS2 cells transfected with the indicated miRNAs. NC, negative control. Cells were maintained in culture for 4 d prior to counting.

Transfection of CD133$^{low}$ SaOS2 Cells with miRNAs Results in Drug Resistance CD133$^{low}$ SaOS2 cells were isolated by cell sorting and then transfected with negative control (NC) RNA, miR-1 alone, miR-10b alone, miR-133a alone, or miR-1 plus miR-10b plus miR-133a, similar to Example 1. Each population of transfected cells was then separately maintained in tissue culture for four days in the presence of 30 nM doxorubicin, 2.5 µM cisplatin, or 320 nM methotrexate, and then cells were counted. Results are shown in FIG. 21. As is evident from FIG. 21, CD133$^{low}$ SaOS2 cells transfected with miR-133a alone or with miR-1 plus miR-10b plus miR-133a proliferated to a greater extent than negative control in the presence of cisplatin and in the presence of methotrexate. The addition of miR-133a thus was associated with increased resistance to cisplatin and methotrexate.

EXAMPLE 8 miR-1, miR-10b, and miR-133a are Induced by Cisplatin Treatment

Figure 22:
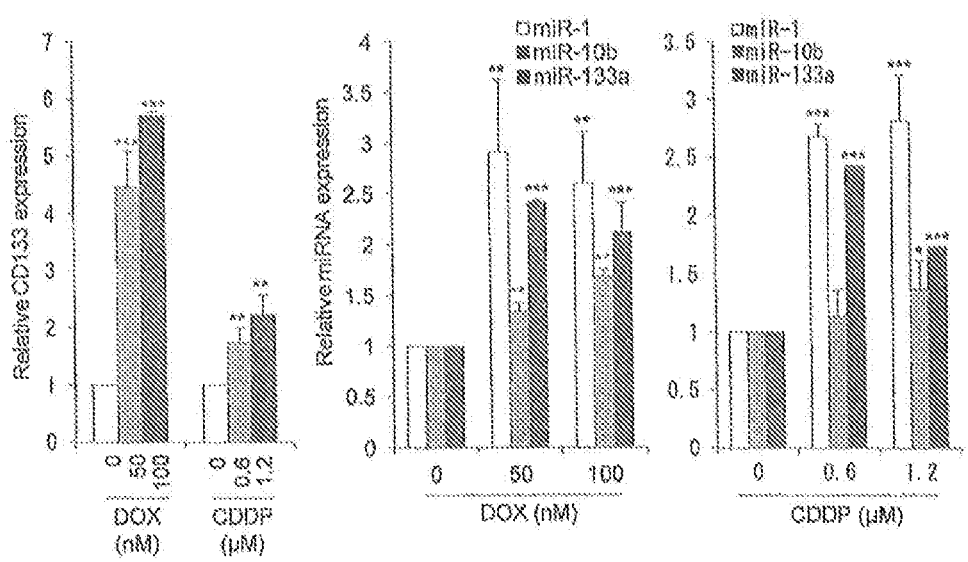
FIG. 22 comprises three graphs depicting (left) induction of mRNA for CD133 by doxorubicin (DOX) and cisplatin (CDDP) in 143B cells; (middle) induction of miR-1, miR-10b, and miR-133a by DOX in 143B cells; and (right) induction of miR-1, miR-10b, and miR-133a by CDDP in 143B cells (*P<0.05, P<0.01, *P<0.001).
Figure 23:
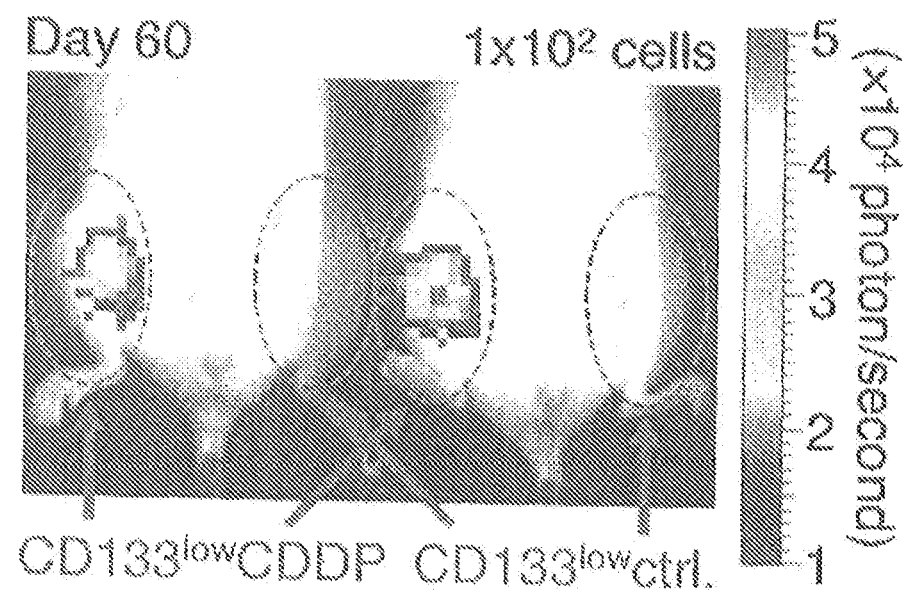
FIG. 23 is a pair of juxtaposed photographic images depicting tumorigenicity of cisplatin (CDDP)-treated CD133$^{low}$ HOS-luc cells in mice. Luminescence of the tumors xenografted with CDDP-treated cells (animals' right tibias) and saline-treated control cells (animals' left tibias) are identified by in vivo imaging system (IVIS). CDDP-treated CD133$^{low}$ cells formed tumors with as few as 100 cells (n=5 per group).

The expressions of miR-1, miR-10b, and miR-133a, as well as CD133, were induced by cisplatin treatment. qRT-PCR analysis showed that DOX-treated or CDDP-treated (3 days) 143B cells expressed an increased level of miR-1, miR-10b, and miR-133a relative to untreated 143B cells (FIG. 22). In addition, the expression of miR-133a was enhanced by cisplatin in CD133$^{low}$ HOS cells. Furthermore, exposure to CDDP increased in vivo tumorigenicity of CD133$^{low}$ HOS population. CDDP-treated CD133$^{low}$ HOS cells could form tumors with as few as 100 cells per injection, whereas the untreated CD133$^{low}$ HOS cells could not (FIG. 23 and Table 9). These data indicate that the TIC phenotypes, as well as the expression of CD133 mRNA and miR-133a, might be enhanced by chemotherapeutics. Therefore, we reasoned that silencing of miR-133a before or during chemotherapy would prevent the increase of the expression of miR-133a, which enhanced TIC phenotypes and was induced by chemotherapeutics.

EXAMPLE 9

Antisense to miR-133a Reduces Proliferation of CD133$^{high}$ Cells

Figure 24:
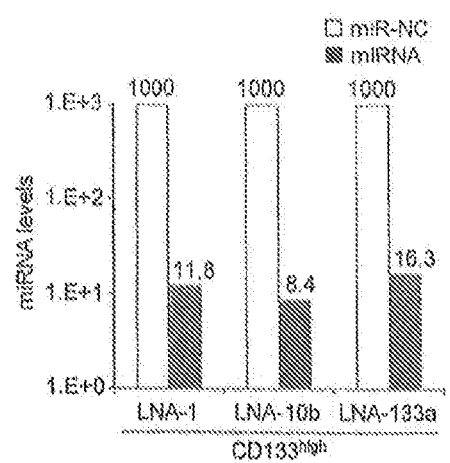
FIG. 24 is a graph depicting knock-down of miR-1, miR-10b, and miR-133 expression in CD133$^{high}$ SaOS2 cells transfected with locked nucleic acid (LNA)-1 LNA-10b, LNA-133a, and LNA-NC oligonucleotides.
Figure 25:
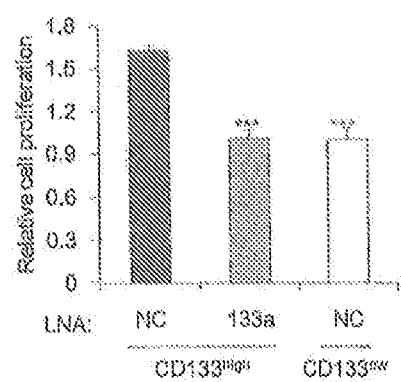
FIG. 25 is a graph depicting cell proliferation on day 4 after transfection of LNA-133a and LNA-NC (negative control) oligonucleotides in CD133$^{high}$ and CD133$^{low}$ cells (n=3 per group; ***P<0.001).

To evaluate whether silencing of miR-133a can suppress malignant phenotypes of osteosarcoma, experiments opposite those of Example 8 were performed by introducing locked nucleic acid (LNA) anti-miR-133a. LNA is a class of nucleic acid analogs possessing very high affinity and excellent specificity toward complementary DNA and RNA, and LNA oligonucleotides have been applied as antisense molecules both in vitro and in vivo. Elmèn, J et al. (2008) Nature 452:896-9; Obad, S et al. (2011) Nat. Genet. 43:371-8. CD133$^{high}$ population of SaOS2 and HOS cells was isolated by cell sorting and transfected with LNA-anti-miR-133a (LNA-133a) and LNA-negative control (LNA-NC). As a control, the isolated CD133$^{low}$ SaOS2 and HOS cells were also transfected with LNA-NC. The efficacy of LNA-133a for the silencing of miR-133a was confirmed by real-time RT-PCR analysis (FIG. 24). CD133$^{high}$ SaOS2 and HOS cells transfected with LNA-133a were suppressed in proliferation rate to the same level of CD133$^{low}$ cells transfected with LNA-NC (FIG. 25).

EXAMPLE 10

Figure 26:
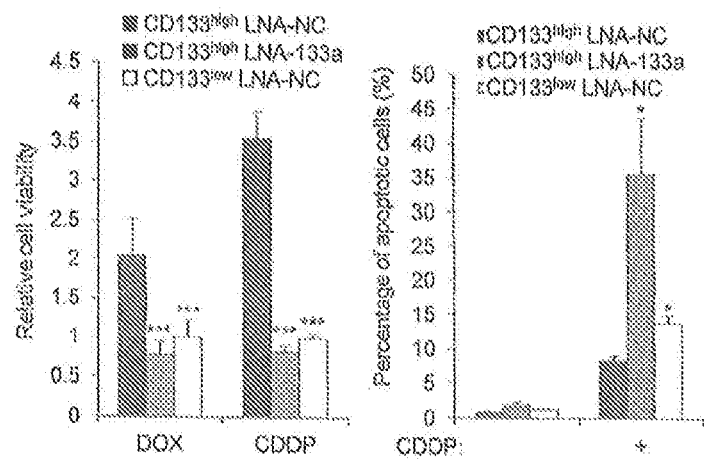
FIG. 26 is pair of graphs depicting (left) cell viability of indicated cell types grown in the presence of doxorubicin (DOX, 0.4 μM, 48 h) or cisplatin (CDDP, 5 μM, 48 h) measured 24 h after transfection with LNA-133a or LNA-NC; and (right) percentage of apoptotic cells in indicated cell types grown in the presence (+) or absence (−) of cisplatin (CDDP, 5 μM, 48 h) measured 24 h after transfection with LNA-133a or LNA-NC.
Figure 27:
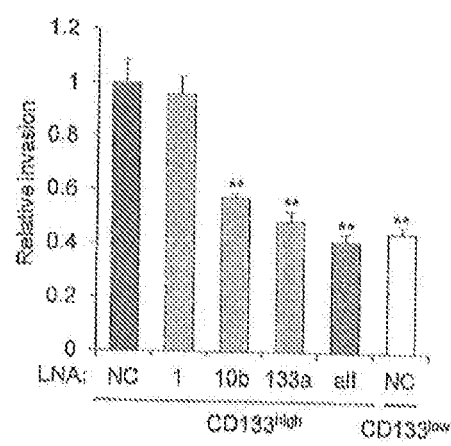
FIG. 27 is a graph depicting invasion assays in indicated LNA-treated SaOS2 CD133$^{high}$ and CD133$^{low}$ populations (n=3 per group; **P<0.01).
Figure 28:
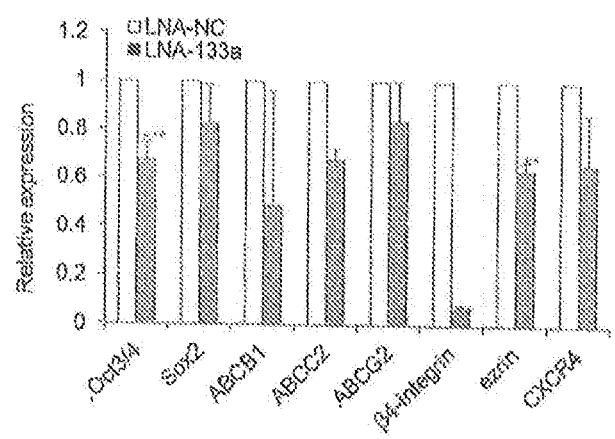
FIG. 28 is a graph depicting quantitative polymerase chain reaction (qPCR) analysis of genes associated with stemness, drug resistance, and metastasis of osteosarcoma in CD133$^{high}$ cells transfected with LNA-133a and LNA-NC oligonucleotides. β-actin was used as an internal control.

LNA-133a-Transduced CD133$^{high}$ Cells Exhibit Enhanced Drug Sensitivity and Decreased Invasiveness LNA-133a-transduced CD133$^{high}$ cells exhibited enhanced sensitivity to DOX and CDDP at the level of LNA-NC-transduced CD133$^{low}$ cells. These results were validated by counting Hoechst-stained cells showing apoptotic nuclear condensation and fragmentation in CD133$^{high}$ cells. There was a significantly higher apoptotic cell death rate in LNA-133a-transduced CD133$^{high}$ cells compared to control CD133$^{high}$ cells (FIG. 26). Furthermore, LNA-133a decreased the invasiveness of CD133$^{high}$ SaOS2 and HOS populations (FIG. 27) and the expression of the molecules associated with CD133$^{high}$ phenotypes (FIG. 28). Collectively, these observations suggest that silencing of miR-133a in CD133$^{high}$ cells can reduce the malignant phenotype of osteosarcoma TICs, including drug resistance and invasion.

EXAMPLE 11

Figure 29:
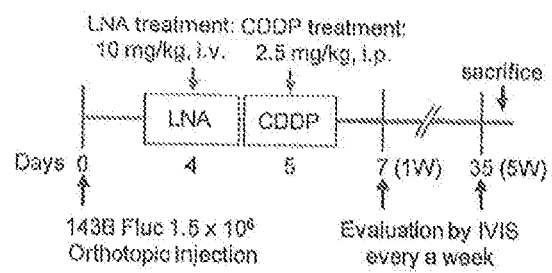
FIG. 29 is a schematic depicting LNA-133a (LNA) and cisplatin (CDDP) administration schedule for 143B-luc-bearing mice. IVIS, in vivo imaging system.
Figure 30:
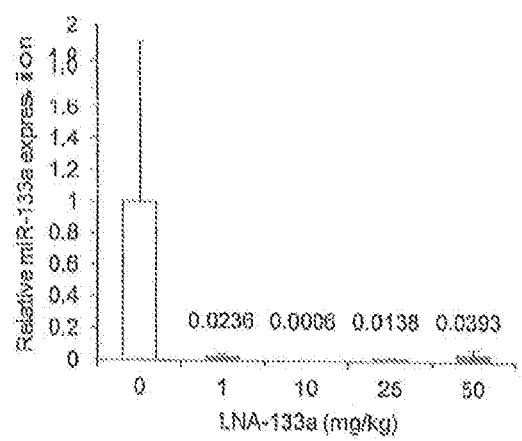
FIG. 30 is a graph depicting expression of miR-133a in 143B-luc tumors according to the dose of LNA-133a (n=3 per group).

Silencing miR-133a In Vivo is Effective for the Treatment of Osteosarcoma and Exhibits Synergistic Efficacy in Combination with CDDP To extend the in vitro findings and to determine whether silencing of miR-133a could be an effective therapeutic option for osteosarcoma treatment, the effect of LNA-133a on a spontaneous lung metastasis model of osteosarcoma was examined. Experimentally, 1.5×10$^6$ cells of 143B transfected with firefly luciferase gene (143B-luc) were implanted orthotopically into the right proximal tibia of athymic nude mice. The implanted tumor growth and the presence of distant metastases were analyzed weekly for luciferase bioluminescence using an in vivo imaging system (IVIS). A new treatment protocol was made of LNA-133a intravenous (i.v.) administration (10 mg kg$^{-1}$) 24 h before intraperitoneal (i.p.) injection of CDDP (2.5 mg kg$^{-1}$) (FIG. 29) in order to decrease drug resistance and to prevent the induction of TIC phenotypes by chemotherapy, which were observed in in vitro experiments. Before the animal study of this protocol, we confirmed reduced miR-133a levels in osteosarcoma tissues from LNA-133a-treated mice compared with those from saline-treated mice (FIG. 30). To assess the efficacy of the new treatment protocol, results were compared with three control groups (n=10 each): a saline control group, an LNA group, and a CDDP group. At 5 weeks, half the mice in each group were euthanized for further analysis; the remaining mice were monitored for survival.

Figure 31:
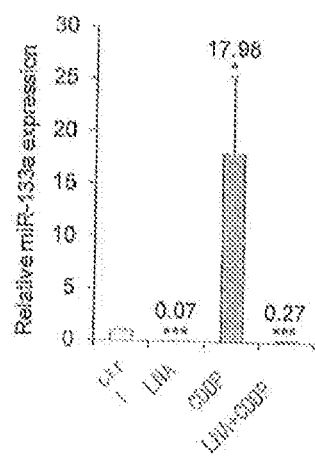
FIG. 31 is a graph depicting relative expression of miR-133a in mice bearing 143B-luc tumors and treated with saline alone, LNA-133a alone, cisplatin (CDDP) alone, or LNA-133 plus CDDP (*P<0.05, ***P<0.001).
Figure 32:
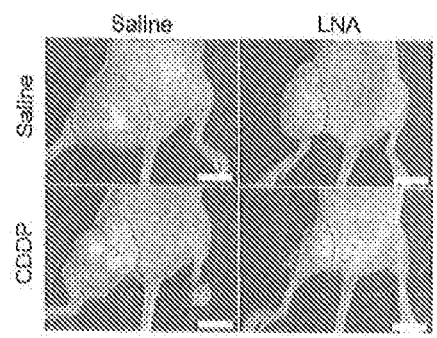
FIG. 32 is a group of four photographic images depicting macroscopic appearance, on day 36, of mice bearing 143B-luc tumors and treated with saline alone, LNA-133a alone, cisplatin (CDDP) alone, or LNA-133 plus CDDP. Scale bar, 10 mm.
Figure 33:
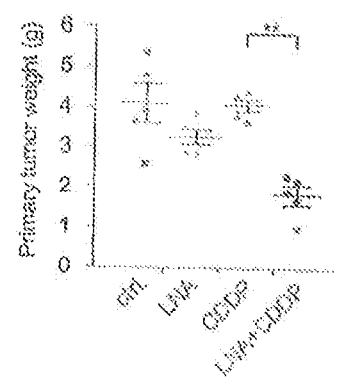
FIG. 33 is a graph depicting weight of 143B-luc tumors, on day 36, from each indicated treatment group (**P<0.01).

Results. The expression of miR-133a of tumors was decreased in the presence of LNA-133a (FIG. 31). Mice that had been administered LNA-133a (10 mg kg$^{-1}$ i.v.) and CDDP (2 mg kg$^{-1}$ i.p.) showed a significantly smaller tumor growth compared to the other groups (FIGS. 32 and 33). No significant differences in tumor growth were observed in the presence or in the absence of CDDP alone (FIGS. 32 and 33). Furthermore, lung metastasis was observed in 10/10 (100%) of the saline group, 7/10 (70%) of the LNA group, 8/10 (80%) of CDDP group, and only 3/10 (30%) of combination group (LNA-133a+CDDP) on day 35 (Table 11).

TABLE 11

Outcome of LNA treatment in osteosarcoma-bearing mice

| Group | Tumor weight (mean) (g) | Lung metastasis | Luminescence of lung (mean) |
|---|---|---|---|
| ctrl. | 3.928 | 10/10 | 5047 |
| LNA | 3.143 | 7/10 | 1744 |
| CDDP | 3.957 | 8/10 | 2855 |
| LNA + CDDP | 1.901 | 3/10 | 582 |

The average luminescence at chest region was significantly decreased in mice treated with the combination of LNA-133a and CDDP. Both the number and size of lung metastasis at every lobe were validated in the luciferase assay and histopathological examination.

Notably, the effect of the combination therapy (LNA-133a+CDDP) was found to exhibit synergistic inhibition of lung metastasis.

Figure 34:
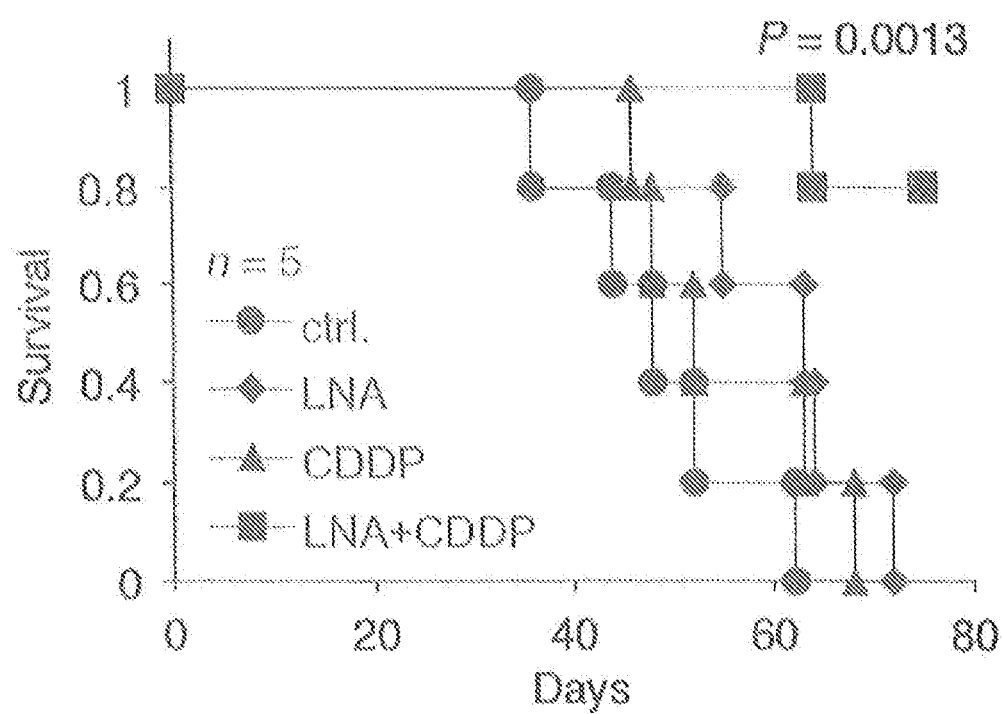
FIG. 34 is a graph depicting survival of mice bearing 143B-luc tumors and treated with saline alone, LNA-133a alone, cisplatin (CDDP) alone, or LNA-133 plus CDDP. Kaplan-Meier analysis and log-rank test (n=5 per group, P=0.0013).

Furthermore, the combination therapy (LNA-133a+CDDP) significantly extended the survival period of tumor-bearing mice (log-rank test, P=0.0084, FIG. 34). Despite the highly conserved sequence of mature human miR-133a and murine miR-133a (e.g., GenBank Accession No. NR_029676; 5'-UUUGGUCCCCUUCAACCAGCUG-3'; SEQ ID NO:3), all mice showed minimal toxic effects on various tissue including heart, liver, and skeletal muscle during the observation period. Thus, systemic administration of LNA-133a is effective for suppression of tumor growth and lung metastasis in the xenograft model for highly metastatic osteosarcoma in the presence of cisplatin.

EXAMPLE 12

Identification of Gene Targets for miR-133a

Figure 35:
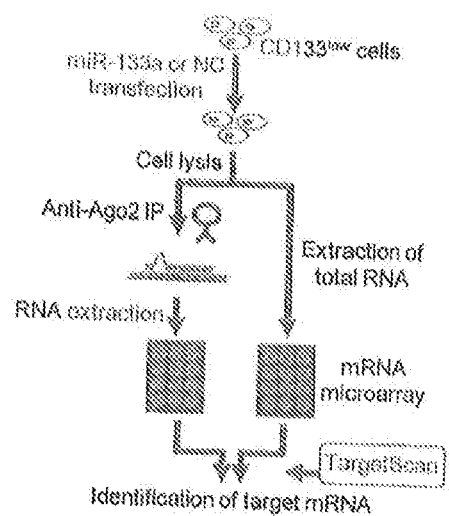
FIG. 35 is a schematic depicting a strategy used to identify target genes of miR-133a. Anti-Ago2 IP, anti-Ago2 antibody immunoprecipitation.
Figure 36:
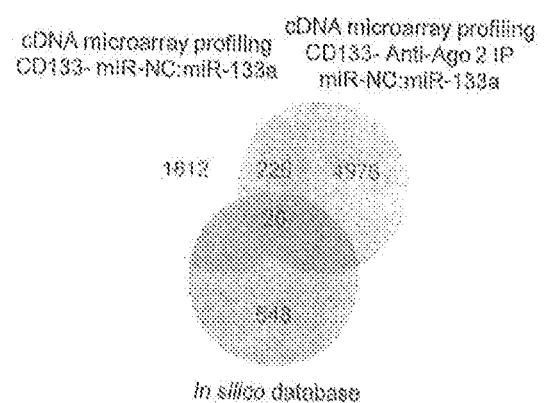
FIG. 36 is a Venn diagram depicting candidate target messenger RNAs (mRNAs) of miR-133a according to complementary DNA (cDNA) microarray and in silico database analysis.

The examples above establish that miR-133a regulates the malignancy of CD133$^{high}$ osteosarcoma TICs, and inhibition of miR-133a expression in osteosarcoma cells inhibits the tumor development. In order to understand the mechanisms regulated by miR-133a in CD133$^{high}$ osteosarcoma TICs, candidate mRNA expression profiling was performed by two different microarray analyses together with in silico predictions (FIG. 35). We detected 1812 downregulated genes with at least a 1.2-fold decrease in the first microarray analysis of total RNA collected from SaOS2 CD133$^{low}$ cells transduced miR-133a or NC, whereas 4976 upregulated genes were detected with at least a 2.0-fold increase in the second microarray analysis of mRNA expression in RNA collected from anti-Ago2 antibody immunoprecipitation in CD133$^{low}$ cells transduced with miR-133a or NC (FIG. 36). Subsequently, 226 genes were collected by both methods (Table 12), and 20 genes were identified in TargetScanHuman 6.0, one of the publicly available in silky databases (FIG. 36).

TABLE 12

Predicted gene targets for miR-133a by two analyses of cDNA microarray and in silico prediction

| Gene Symbol | GenBank Accession | Gene Name | Fold increase, miR-133a-Ago2 complex | Fold decrease, miR-133a transfection |
|---|---|---|---|---|
| PGAP1 | NM_024989 | post-GPI attachment to proteins 1 | 7.60 | −0.42 |
| C1orf118 | XR_041258 | chromosome 1 open reading frame 118 | 7.19 | −0.28 |

TABLE 12-continued

Predicted gene targets for miR-133a by two analyses of cDNA microarray and in silico prediction

| Gene Symbol | GenBank Accession | Gene Name | Fold increase, miR-133a-Ago2 complex | Fold decrease, miR-133a transfection |
|---|---|---|---|---|
| DYNLT3 | NM_006520 | dynein, light chain, Tetex-type 3 | 7.17 | −0.42 |
| AGFG1 | NM_001135187 | ArfGAP with FG repeats 1 | 6.69 | −0.28 |
| WDR44 | NM_019045 | WD repeat domain 44 | 6.36 | −0.43 |
| FLYWCH1 | NM_020912 | FLYWCH-type zinc finger 1 | 5.62 | −0.32 |
| CARKD | NM_018210 | carbohydrate kinase domain containing | 5.50 | −0.66 |
| CUL4B | NM_003588 | cullin 4B | 5.30 | −0.40 |
| ETS1 | NM_005238 | v-ets erythroblastosis virus E26 oncogene homolog 1 (avian) | 5.29 | −0.74 |
| HDAC6 | NM_006044 | histone deacetylase 6 | 5.20 | −0.36 |
| C19orf10 | NM_019107 | chromosome 19 open reading frame 10 | 5.17 | −0.36 |
| RASA2 | NM_006506 | RAS p21 protein activator 2 | 5.15 | −0.44 |
| KIAA1958 | NM_133465 | KIAA1958 | 5.14 | −0.28 |
| LOC645851 | NR_024395 | hypothetical LOC645851 | 5.09 | −0.37 |
| TBPL1 | NM_004865 | TBP-like 1 | 4.86 | −0.33 |
| SNX26 | NM_052948 | sorting nexin 26 | 4.73 | −0.27 |
| SCRN1 | NM_001145513 | secernin 1 | 4.72 | −0.55 |
| LOC100132672 | XR_038504 | similar to glycosyltransferase 8 domain containing 3 | 4.61 | −0.36 |
| AP4S1 | NM_001128126 | adaptor-related protein complex 4, sigma 1 subunit | 4.39 | −0.59 |
| SF3B3 | NM_012426 | splicing factor 3b, subunit 3, 130 kDa | 4.34 | −0.27 |
| LMBR1 | NM_022458 | limb region 1 homolog (mouse) | 4.31 | −0.40 |
| HERC4 | NM_022079 | hect domain and RLD 4 | 4.26 | −0.69 |
| ADAMTS1 | NM_006988 | ADAM metallopeptidase with thrombospondin type 1 motif, 1 | 4.17 | −0.47 |
| CYB5R4 | NM_016230 | cytochrome b5 reductase 4 | 4.14 | −0.29 |
| LHFPL2 | NM_005779 | lipoma HMGIC fusion partner-like 2 | 4.11 | −0.30 |
| FAM13AOS | NR_002806 | FAM13A opposite strand (non-protein coding) | 4.04 | −0.28 |
| RALGAPA1 | NM_194301 | Ral GTPase activating protein, alpha subunit 1 (catalytic) | 4.00 | −0.53 |
| TNFRSF13C | NM_052945 | tumor necrosis factor receptor superfamily, member 13C | 3.99 | −0.44 |
| LOC100131829 | AK124002 | hypothetical protein LOC100131829 | 3.95 | −0.43 |
| C1orf58 | NM_144695 | chromosome 1 open reading frame 58 | 3.92 | −0.54 |
| TNFRSF10D | NM_003840 | tumor necrosis factor receptor superfamily, member 10d, decoy with truncated death domain | 3.75 | −0.45 |
| ZDHHC17 | NM_015336 | zinc finger, DHHC-type containing 17 | 1.68 | −0.36 |
| LOC729603 | NR_003288 | calcium binding protein P22 pseudogene | 3.62 | −0.34 |
| SNX30 | NM_001012994 | sorting nexin family member 30 | 3.55 | −0.41 |
| TSTD2 | NM_139246 | thiosulfate sulfurtransferase (rhodanese)-like domain containing 2 | 3.52 | −0.38 |
| SPRYD4 | NM_207344 | SPRY domain containing 4 | 3.51 | −0.35 |
| PTPMT1 | NM_175732 | protein tyrosine phosphatase, mitochondrial 1 | 3.50 | −0.38 |
| KLHDC4 | NM_017566 | kelch domain containing 4 | 343 | −0.43 |
| SLC30A7 | NM_133496 | solute carrier family 30 (zinc transporter), member 7 | 3.38 | −0.48 |
| TCEA3 | NM_003196 | transcription elongation factor A (SII), 3 | 3.32 | −0.39 |
| GORASP1 | NM_031899 | golgi reassembly stacking protein 1, 65 kDa | 3.17 | −0.51 |
| RBM15B | NM_013286 | RNA binding motif protein 15B | 3.13 | −0.80 |
| PDGFRB | NM_002609 | platelet-derived growth factor receptor, beta polypeptide | 3.13 | −0.37 |
| ITPRIPL2 | NM_001034841 | inositol 1,4,5-triphosphate receptor interacting protein-like 2 | 3.09 | −0.34 |
| FBXO3 | NM_033406 | F-box protein 3 | 3.01 | −0.35 |
| FAM122B | NM_001166600 | family with sequence similarity 122B | 3.00 | −0.30 |
| MINPP1 | NM_004897 | multiple inositol polyphosphate histidine phosphatase, 1 | 2.98 | −0.28 |
| SPOPL | NM_001001664 | speckle-type POZ protein-like | 2.94 | −0.47 |
| FAM86B1 | NM_001083537 | family with sequence similarity 86, member B1 | 2.85 | −0.44 |
| LOC100128071 | XM_001724939 | similar to hCG41624 | 2.83 | −0.31 |
| CCNT1 | NM_001240 | cyclin T1 | 2.82 | −0.53 |
| AP2M1 | NM_004068 | adaptor-related protein complex 2, mu 1 subunit | 2.80 | −0.44 |
| AKIRIN1 | NM_024595 | akirin 1 | 2.73 | −0.27 |
| CHMP5 | NM_016410 | chromatin modifying protein 5 | 2.69 | −0.61 |
| PPM1K | NM_152542 | protein phosphatase 1K (PP2C domain containing) | 2.67 | −0.53 |

TABLE 12-continued

Predicted gene targets for miR-133a by two analyses of cDNA microarray and in silico prediction

| Gene Symbol | GenBank Accession | Gene Name | Fold increase, miR-133a-Ago2 complex | Fold decrease, miR-133a transfection |
|---|---|---|---|---|
| MICALL2 | NM_182924 | MICAL-like 2 | 2.66 | −0.29 |
| DGKZ | AK123378 | diacylglycerol kinase, zeta 104 kDa | 2.65 | −0.39 |
| SCARNA16 | NR_003013 | small Cajal body-specific RNA 16 | 2.65 | −0.50 |
| SERPINE1 | NM_000602 | serpin peptidase inhibitor, clade E (nexin, plasminogen activator inhibitor type 1), member 1 | 2.65 | −0.61 |
| STARD13 | NM_178006 | StAR-related lipid transfer (START) domain containing 13 | 2.58 | −0.28 |
| ROD1 | NM_005156 | ROD1 regulator of differentiation 1 (S. pombe) | 2.55 | −0.36 |
| VEGFC | NM_005429 | vascular endothelial growth factor C | 2.45 | −0.35 |
| MYH9 | NM_002473 | myosin, heavy chain 9, non-muscle | 2.43 | −0.39 |
| CCNJ | NM_019084 | cyclin J | 2.41 | −0.26 |
| WDR66 | NM_144668 | WD repeat domain 66 | 238 | −0.32 |
| CSRNP1 | NM_033027 | cysteine-serine-rich nuclear protein 1 | 2.34 | −0.28 |
| MYBL1 | NM_001144755 | v-myb myeloblastosis viral oncogene homolog (avian)-like 1 | 2.32 | −0.29 |
| EME2 | BC041011 | essential meiotic endonuclease 1 homolog 2 (S. pombe) | 2.31 | −0.44 |
| MGC27382 | AK091757 | hypothetical MGC27382 | 2.27 | −0.33 |
| MMP14 | NM_004995 | matrix metallopeptidase 14 (membrane-inserted) | 2.27 | −0.42 |
| WASH1 | NM_182905 | WAS protein family homolog 1 | 2.26 | −0.32 |
| RIMS2 | NM_014677 | regulating synaptic membrane exocytosis 2 | 2.25 | −0.45 |
| HSPG2 | NM_005529 | heparan sulfate proteoglycan 2 | 2.25 | −0.45 |
| HDAC8 | NM_018486 | historic deacetylase 8 | 2.21 | −0.34 |
| AK2 | NM_013411 | adenylate kinase 2 | 2.20 | −0.30 |
| SRRM2 | NM_016333 | serine/arginine repetitive matrix 2 | 2.19 | −0.28 |
| LOC731419 | XM_001132610 | hypothetical protein LOC731419 | 2.19 | −0.32 |
| SYNGR3 | NM_004209 | synaptogyrin 3 | 2.11 | −0.33 |
| PRUNE2 | NM_015225 | prune homolog 2 (Drosophila) | 2.11 | −0.38 |
| MLKL | NM_152649 | mixed lineage kinase domain-like | 2.10 | −0.30 |
| DST | NM_001723 | dystonin | 2.10 | −0.44 |
| PBXIP1 | NM_020524 | pre-B-cell leukemia homeobox interacting protein 1 | 2.03 | −0.78 |
| ANTXR2 | NM_058172 | anthrax toxin receptor 2 | 1.98 | −0.61 |
| NSF | NM_006178 | N-ethylmaleimide-sensitive factor | 1.98 | −0.32 |
| APH1A | NM_001077628 | anterior pharynx defective 1 homolog A (C. elegans) | 1.98 | −0.34 |
| RASA1 | NM_002890 | RAS p21 protein activator (GTPase activating protein) 1 | 1.95 | −0.46 |
| BAIAP2 | NM_017451 | BAH-associated protein 2 | 1.91 | −0.29 |
| GARNL3 | NM_032293 | GTPase activating Rap/RanGAP domain-Like 3 | 1.90 | −0.49 |
| CKLF | NM_016951 | chemokine-like factor | 1.89 | −0.38 |
| SNORD17 | NR_003045 | small nucleolar RNA, C/D box 17 | 1.88 | −0.27 |
| TRIT1 | NM_017646 | tRNA isopentenyltransferase 1 | 1.88 | −0.43 |
| FILIP1L | NM_182909 | filamin A interacting protein 1-like | 1.88 | −0.36 |
| VAMP2 | NM_014232 | vesicle-associated membrane protein 2 (synaptobrevin 2) | 1.87 | −0.31 |
| TBL1X | NM_005647 | transducin (beta)-like 1X-linked | 1.87 | −0.30 |
| LOC729314 | XR_037423 | similar to POM121-like protein 1 | 1.85 | −0.63 |
| RHD | NM_016124 | Rh blood group, D antigen | 1.84 | −0.28 |
| HERC2 | NM_004667 | hect domain and RLD 2 | 1.81 | −0.36 |
| KIAA1967 | NM_021174 | KIAA1967 | 1.78 | −0.32 |
| YIPF2 | NM_024029 | Yip1 domain family, member 2 | 1.71 | −0.48 |
| MLL5 | NM_182931 | myeloid/lymphoid or mixed-lineage leukemia 5 (trithorax homolog, Drosophila) | 1.71 | −0.41 |
| DUSP11 | NM_003584 | dual specificity phosphatase 11 (RNA/RNP complex 1-interacting) | 1.70 | −0.28 |
| ABL2 | NM_001100108 | v-abl Abelson murine leukemia viral oncogene homolog 2 (arg, Abelson-related gene) | 1.68 | −0.30 |
| RBMX2 | NM_016024 | RNA binding motif protein, X-linked 2 | 1.65 | −0.37 |
| ALS2CR8 | NM_024744 | amyotrophic lateral sclerosis 2 (juvenile) chromosome region, candidate 8 | 1.65 | −0.30 |
| IDH1 | NM_005896 | isocitrate dehydrogenase 1 (NADP+), soluble | 1.65 | −0.31 |

TABLE 12-continued

Predicted gene targets for miR-133a by two analyses of cDNA microarray and in silico prediction

| Gene Symbol | GenBank Accession | Gene Name | Fold increase, miR-133a-Ago2 complex | Fold decrease, miR-133a transfection |
|---|---|---|---|---|
| NT5C3L | NM_052935 | 5+40–nucleotidase, cytosolic III-like | 1.63 | −0.40 |
| ERMP1 | NM_024896 | endoplasmic reticulum metallopeptidase 1 | 1.59 | −0.86 |
| GPSM1 | NM_015597 | G-protein signaling modulator 1 (AGS3-like, C. elegans) | 1.53 | −0.47 |
| ARHGEF10L | NM_018125 | Rho guanine nucleotide exchange factor (GEF) 10-like | 1.52 | −0.32 |
| MFN2 | NM_014874 | mitofusin 2 | 1.52 | −0.32 |
| CG030 | NR_026928 | hypothetical CG030 | 1.49 | −0.30 |
| UBXN7 | NM_015562 | UBX domain protein 7 | 1.49 | −0.35 |
| CCDC45 | NM_138363 | coiled-coil domain containing 45 | 1.47 | −0.39 |
| ZNF701 | NM_018260 | zinc finger protein 701 | 1.46 | −0.68 |
| LOC642406 | AK024257 | similar to contactin associated protein-like 3B | 1.46 | −1.34 |
| PHF8 | NM_015107 | PHD finger protein 8 | 1.44 | −0.28 |
| MED23 | NM_015979 | mediator complex subunit 23 | 1.42 | −0.29 |
| ARHGAP11B | NM_001039841 | Rho GTPase activating protein 11B | 1.42 | −0.29 |
| MYST4 | NM_012330 | MYST histone acetyltransferase (monocytic leukemia) 4 | 1.41 | −0.31 |
| SYT17 | NM_016524 | synaptotagmin XVII | 1.40 | −0.39 |
| DPM2 | NM_003863 | dolichyl-phosphate mannosyltransferase polypeptide 2, regulatory subunit | 1.30 | −0.35 |
| TUB | NM_003320 | tubby homolog (mouse) | 1.30 | −0.7.7 |
| TBPL1 | NM_004865 | TBP-like 1 | 1.30 | −0.28 |
| FAM40B | NM_020704 | family with sequence similarity 40, member B | 1.30 | −0.62 |
| DOLPP1 | NM_020438 | dolichyl pyrophosphate phosphatase 1 | 1.29 | −0.34 |
| HIST1H2BM | NM_003521 | histone cluster 1, H2bm | 1.29 | −0.35 |
| ZBTB7A | NM_015898 | zinc linger and BTB domain containing 7A | 1.28 | −0.28 |
| SLC30A7 | NM_133496 | solute carrier family 30 (zinc transporter), member 7 | 1.25 | −0.36 |
| HCRTR1 | NM_001525 | hypocretin (orexin) receptor 1 | 1.22 | −0.27 |
| DNAJB6 | NM_005494 | DnaJ (Hsp40) homolog, subfamily B, member 6 | 1.22 | −0.56 |
| QPRT | NM_014298 | quinolinate phosphoribosyltransferase | 1.20 | −0.32 |
| CCDC75 | NM_174931 | coiled-coil domain containing 75 | 1.20 | −0.29 |
| NPTXR | NM_014293 | neuronal pentraxin receptor | 1.19 | −0.63 |
| RHOB | NM_004040 | ras homolog gene family, member B | 1.19 | −0.48 |
| CDH7 | NM_004361 | cadherin 7, type 2 | 1.17 | −0.34 |
| COL5A1 | AK057231 | collagen, type V, alpha 1 | 1.17 | −0.50 |
| SGMS2 | NM_152621 | sphingomyelin synthase 2 | 1.16 | −0.32 |
| LOC643802 | XM_001716860 | similar to M-phase phosphoprotein 10 (U3 small nucleolar ribonucleoprotein) | 1.15 | −0.53 |
| BCL11A | NM_018014 | B-cell CLL/lymphoma 11 A (zinc finger protein) | 1.14 | −0.28 |
| GEN1 | NM_182625 | Gen homolog 1, endonuclease (Drosophila) | 1.14 | −0.28 |
| ZP1 | NM_207341 | zona pellucida glycoprotein 1 (sperm receptor) | 1.12 | −0.30 |
| EFTUD1 | NM_024580 | elongation factor Tu GTP binding domain containing 1 | 1.12 | −0.47 |
| REEP6 | NM_138393 | receptor accessory protein 6 | 1.10 | −0.58 |
| UBA2 | NM_005499 | ubiquitin-like modifier activating enzyme 2 | 1.08 | −0.38 |
| BRIP1 | NM_032043 | BRCA1 interacting protein C-terminal helicase 1 | 1.06 | −0.27 |
| KPTN | NM_007059 | kaptin (actin binding protein) | 1.06 | −0.57 |
| DZIP1 | NM_014934 | DAZ interacting protein 1 | 1.04 | −0.35 |
| MGC16275 | NR_026914 | hypothetical protein MGC16275 | 1.04 | −0.29 |
| APTX | NM_017692 | aprataxin | 1.03 | −0.29 |
| P2RX4 | NM_002560 | purinergic receptor P2X, ligand-gated ion channel, 4 | 1.02 | −0.79 |
| PCDH24 | NM_017675 | protocadherin 24 | 1.00 | −0.37 |

Figure 37:
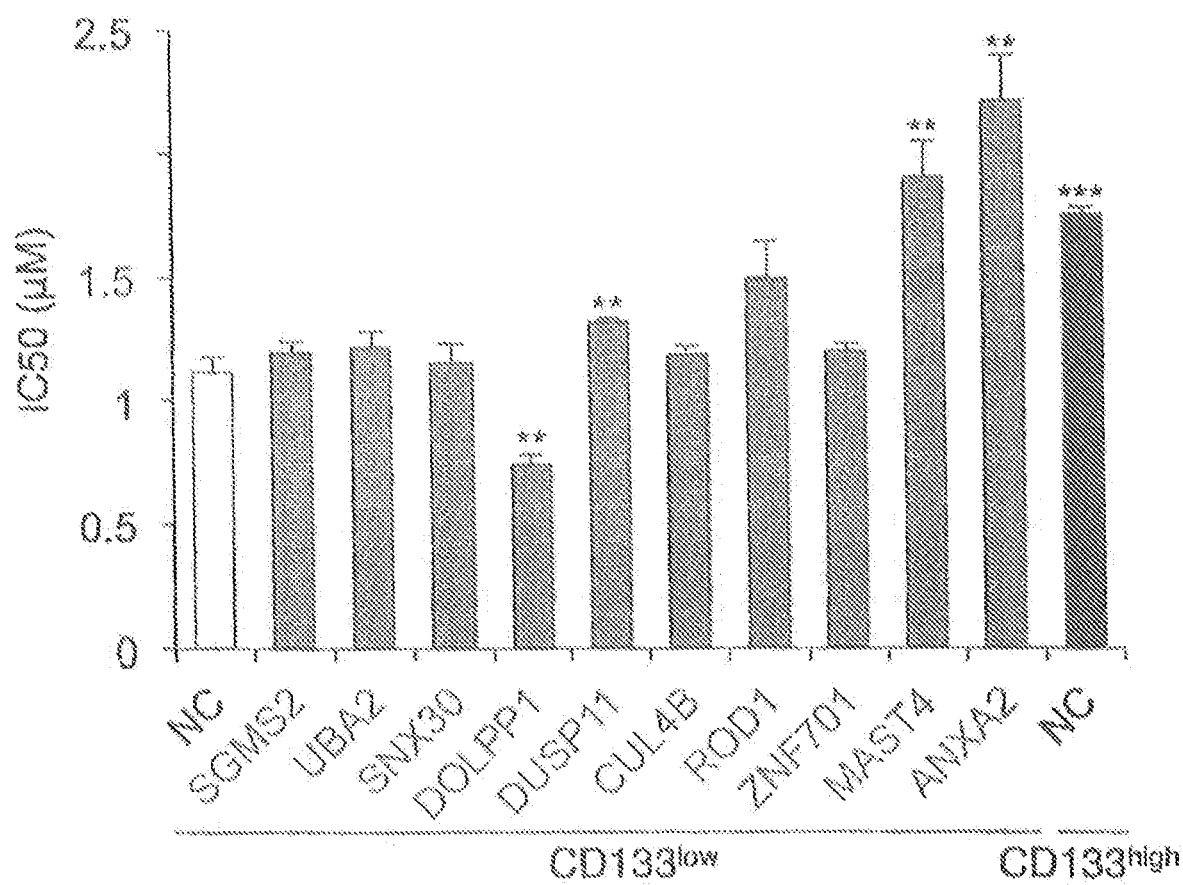
FIG. 37 is a graph depicting inhibition of cell growth by 10 siRNAs on cell transfection arrays in the presence of cisplatin 72 h after transfection (n=3 per group; NC, negative control; P<0.01, *P<0.001).
Figure 38:
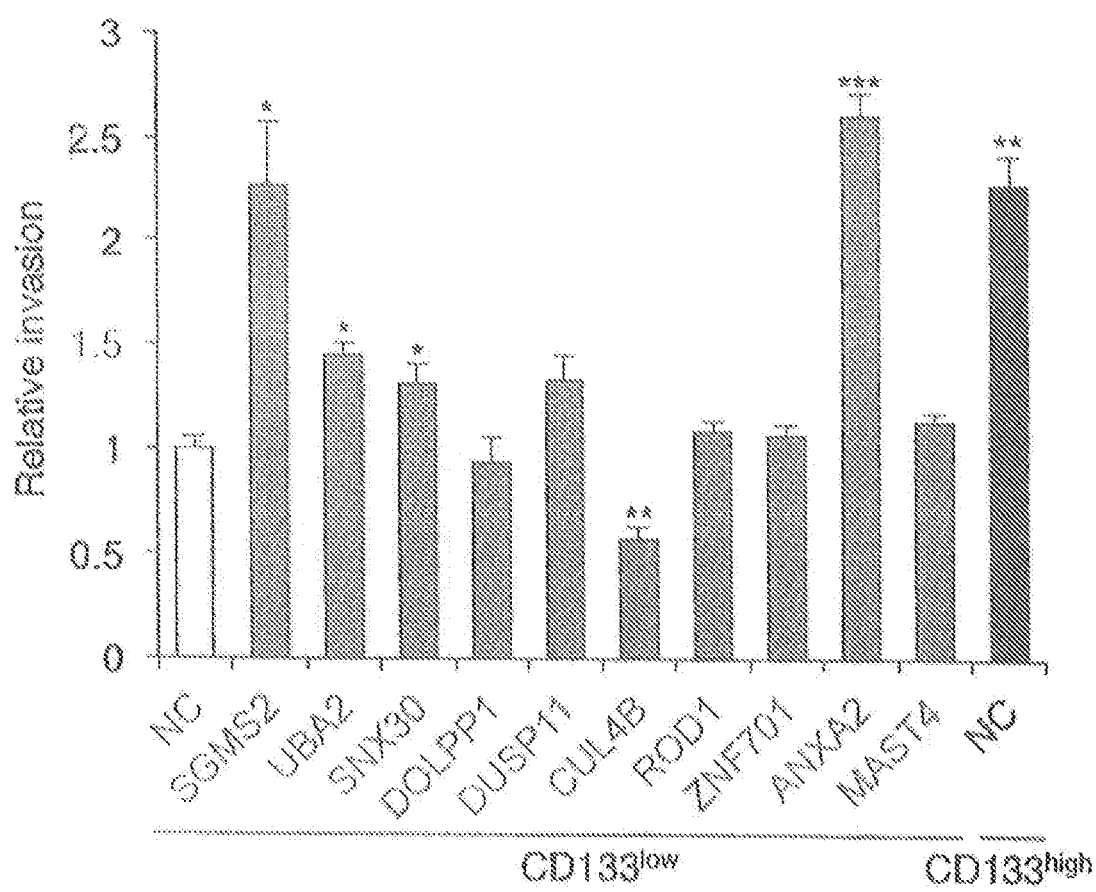
FIG. 38 is a graph depicting invasion assay by 10 siRNAs on cell transfection arrays 72 h after transfection (n=3 per group; NC, negative control; *P<0.05, P<0.01, *P<0.001).

Overall, ten putative candidates for miR-133a target genes were selected with these data combined. Next, the expression of these molecules was reduced using siRNA-induced gene knockdown system to investigate whether these candidates are functionally important targets of miR-133a in osteosarcoma cells. As a result, knockdown of four candidates (ANXA2, DUSP11, MAST4, and ROD1) in CD133$^{low}$ SaOS2 cells enhanced drug resistance (FIG. 37), and knockdown of five candidates (ANXA2, DUSP 11, SGMS2, SNX30, and UBA2) enhanced invasiveness of CD133$^{low}$ SaOS2 cells (FIG. 38).

Of course, the effect of knockdown of these putative target genes would be similar to the effect exerted by miR-133a on these same genes, resulting in enhanced drug resistance and enhanced invasiveness of CD133$^{low}$ SaOS2 cells. Conversely, silencing of miR-133a in CD133$^{low}$ SaOS2 cells would be expected to be permissive for expression of the putative target genes, thereby reducing drug resistance and reducing invasiveness of CD133$^{low}$ SaOS2 cells.

Figure 39:
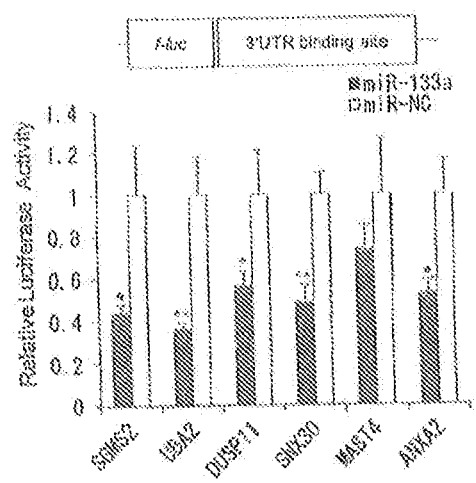
FIG. 39 is a graph depicting luciferase activity in SaOS2 cells co-transfected with miR-133a oligonucleotides and luciferase reporters for the indicated putative miR-133a target genes.

To validate whether these molecules are regulated by miR-133a, the 3'UTR (untranslated region) fragment containing putative miR-133a binding sites was cloned downstream of a luciferase coding sequence, and the luciferase reporter and miR-133a oligonucleotides were co-transfected into SaOS2 cells. As a control, the luciferase reporter and NC oligonucleotides were co-transfected into SaOS2 cells. Luciferase activities were reduced by approximately 39-73% in the cells co-transfected with miR-133a compared with the cells co-transfected with the NC oligonucleotides (FIG. 39). From results of this assay, ANXA2, DUSP 11, MAST4, SGMS2, SNX30, and UBA2 were found to function as direct targets of miR-133a.

Indeed, these target genes or their family genes were previously suggested to function as tumor suppressors in certain other cancers. Gostissa, M et al. (1999) *EMBO J.* 18:6462-71; Caprara, G et al. (2009) *J. Cell. Mol. Med.* 13:2158-70; Nguyen, L N et al. (2006) *Clin. Cancer Res.* 12:6952-9. ANXA2 has been reported to be associated with tumor-suppressive function in osteosarcoma (Gillette, J M (2004) *J. Cell Biochem.* 92:820-32), whereas MAST4 has been unknown in tumor biology (Garland, P (2008) *Brain Res.* 21:12-19).

Figure 40:
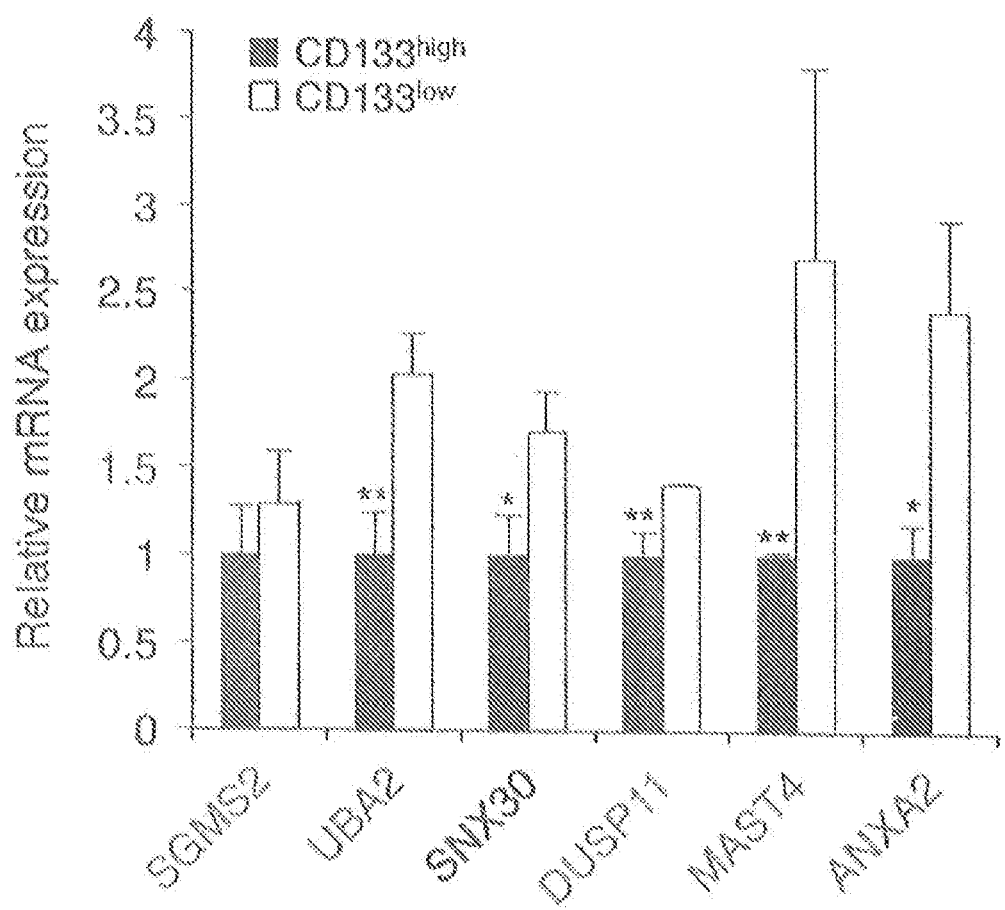
FIG. 40 is a graph depicting inverse correlation between expression of CD133 ($CD133^{high}$ versus $CD133^{low}$) and messenger RNA (snRNA) for indicated targets of miR-133a, as measured by quantitative reverse transcriptase-polymerase chain reaction (qRT-PCR).
Figure 41:
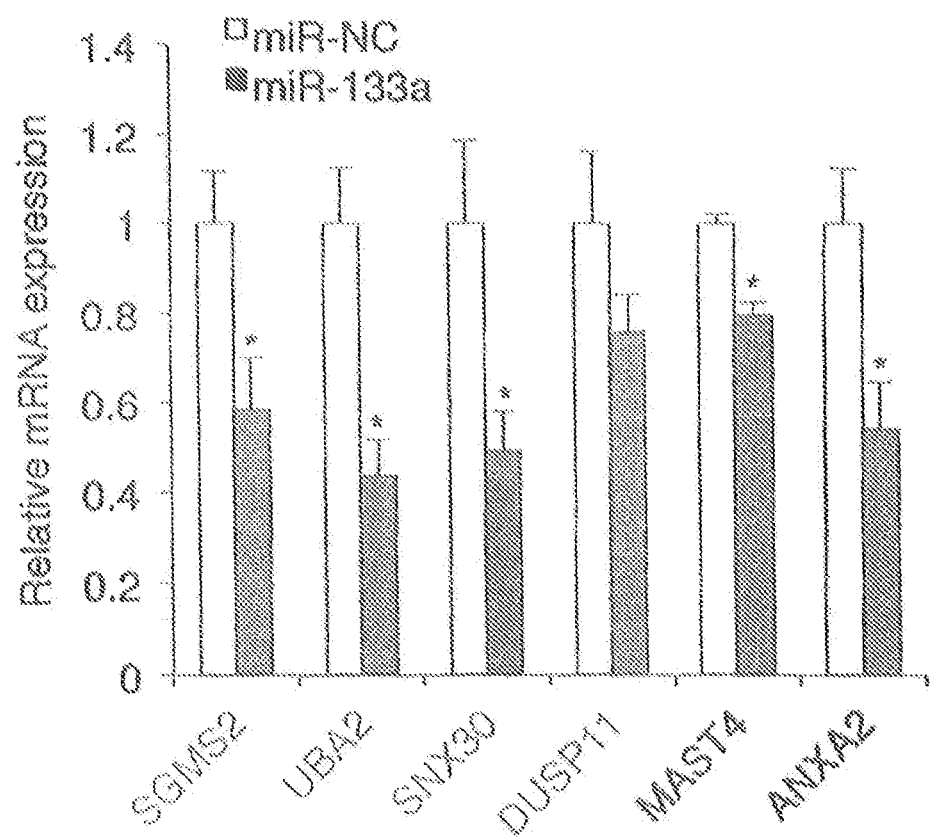
FIG. 41 is a graph depicting decreased expression of messenger RNA (mRNA) for the indicated miR-133a target genes in $CS133^{low}$ SaOS2 cells 48 h after transfection of miR-133a oligonucleotides compared to miR-NC (negative control) oligonucleotides, as measured by quantitative reverse transcriptase-polymerase chain reaction (qRT-PCR).
Figure 42:
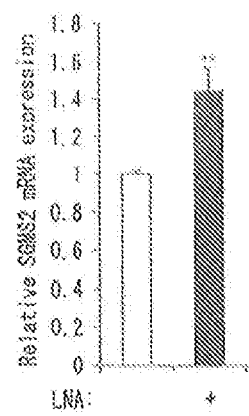
FIG. 42 is a graph depicting increased expression of messenger RNA (mRNA) for SGMS2. in 143B-luc tumors from mice treated with LNA-133a (**P<0.01).
Figure 43:
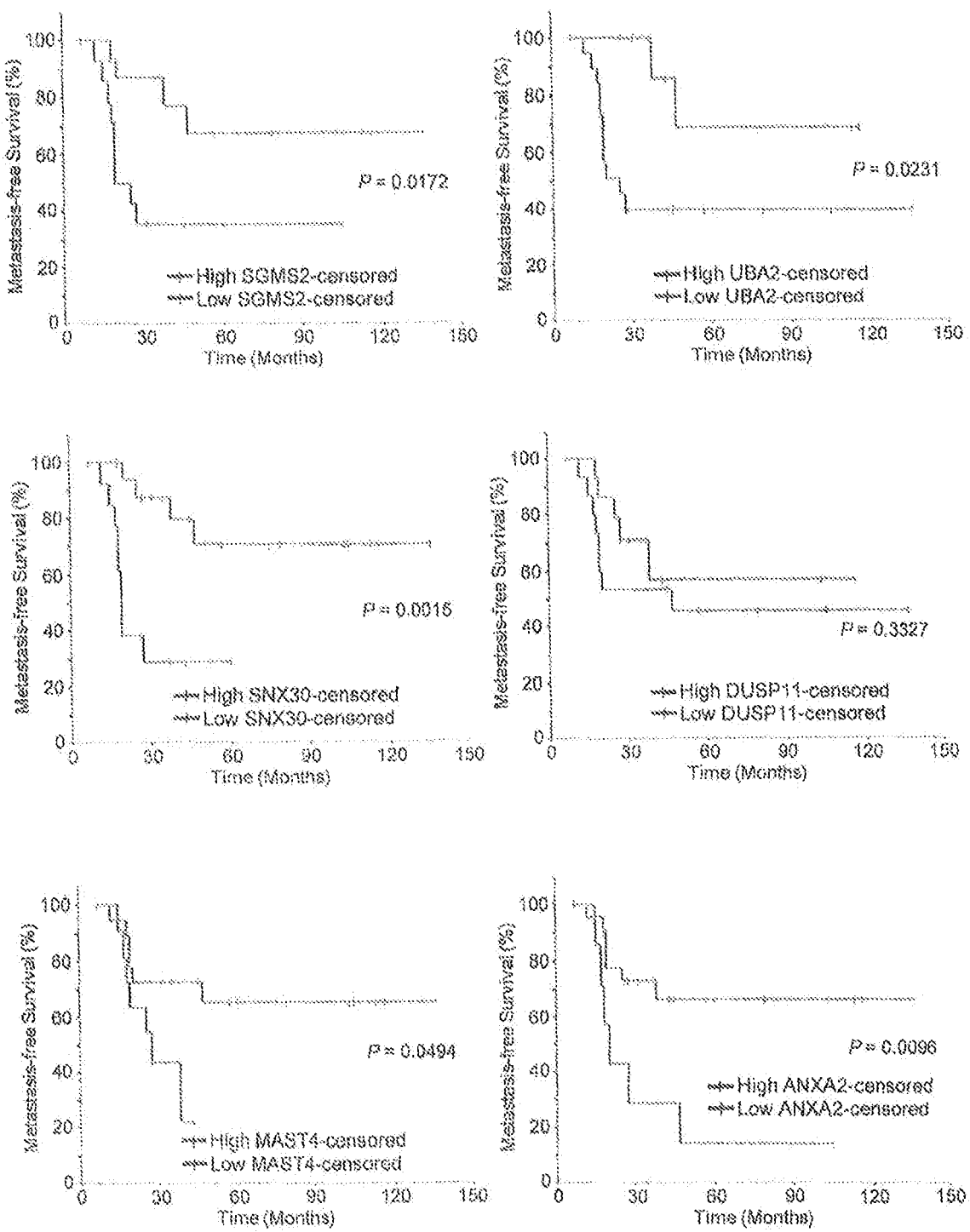
FIG. 43 is a series of six graphs depicting metastasis-free survival of osteosarcoma patients sensored for miR-133a target genes SGMS2, UBA2, SNX30, DUSP11, MAST4, and ANXA2, respectively. The low expression of the direct targets of miR-133a (except for DUSP11) were significantly correlated with a poor prognosis (Kaplan-Meier analysis and log-rank test; P values as shown).

Indeed, as disclosed by the present invention, the expression of all these targets was increased by silencing of miR-133a in CD133$^{high}$ cells (FIG. 40) and decreased by miR-133a upregulation in CD133$^{low}$ cells (FIG. 41), consistent with observed inverse correlations with the expression of CD133 and miR-133a in both xenografted tumors (FIG. 42) and clinical samples (results not shown). The increased expression of the targets by silencing of miR-133a was confirmed by qRT-PCR (results not shown) and immunohistochemistry of LNA-treated tumors (results not shown). Finally, in investigating the relationships between the expression of these targets and osteosarcoma patient prognosis, a strikingly close correlation was found between the mRNA expression of the miR-133a targets and patient prognosis (FIG. 43). Patients with higher expression levels of these targets survived much longer than patients with lower expression, indicating that these targets could function as novel tumor-suppressors in osteosarcoma.

We claim:

1. A method of treating osteosarcoma, comprising administering to a subject in need thereof an effective amount of an antisense molecule specific for microRNA (miRNA) miR-1, thereby treating the osteosarcoma.

2. The method of claim 1, wherein the antisense molecule is stabilized RNA.

3. The method of claim 2, wherein the stabilized RNA is a locked nucleic acid (LNA). oligonucleotide.

4. The method of claim 2, wherein the antisense molecule is DNA.

5. The method of claim 1, wherein the antisense molecule is 20-30 nucleotides long and comprises a nucleotide sequence at least 90 percent identical SEQ ID NO:4.

6. The method of claim 1, wherein the antisense molecule is 20-30 nucleotides long and comprises a nucleotide sequence at least 90 percent identical SEQ ID NO:7.

7. The method of claim 1, wherein the antisense molecule is 20-30 nucleotides long and comprises a nucleotide sequence at least 90 percent identical SEQ ID NO: 10.

8. The method of claim 1, wherein the antisense molecule is associated with a nucleic acid delivery vehicle.

9. The method of claim 1, wherein the antisense molecule is 20-30 nucleotides long and comprises a nucleotide sequence identical to SEQ ID NO:4.

10. The method of claim 1, wherein the antisense molecule is 20-30 nucleotides long and comprises a nucleotide sequence identical to SEQ ID NO:7.

11. The method of claim 1, wherein the antisense molecule is 20-30 nucleotides long and comprises a nucleotide sequence identical to SEQ ID NO:10.

12. The method of claim 9, wherein the antisense molecule is associated with a nucleic acid delivery vehicle.

13. The method of claim 10, wherein the antisense molecule is associated with a nucleic acid delivery vehicle.

14. The method of claim 11, wherein the antisense molecule is associated with a nucleic acid delivery vehicle.

* * * * *

SEQUENCE LISTING

```
<160> NUMBER OF SEQ ID NOS: 105

<210> SEQ ID NO 1
<211> LENGTH: 22
<212> TYPE: RNA
<213> ORGANISM: Artificial sequence
<220> FEATURE:
<223> OTHER INFORMATION: Synthetic oligonucleotide

<400> SEQUENCE: 1
uggaauguaa agaaguaugu au                                              22

<210> SEQ ID NO 2
<211> LENGTH: 23
<212> TYPE: RNA
<213> ORGANISM: Artificial sequence
<220> FEATURE:
<223> OTHER INFORMATION: Synthetic oligonucleotide

<400> SEQUENCE: 2
uacccuguag aaccgaauuu gug                                             23

<210> SEQ ID NO 3
<211> LENGTH: 22
<212> TYPE: RNA
<213> ORGANISM: Artificial sequence
<220> FEATURE:
<223> OTHER INFORMATION: Synthetic oligonucleotide

<400> SEQUENCE: 3
uuuggucccc uucaaccagc ug                                              22

<210> SEQ ID NO 4
<211> LENGTH: 20
<212> TYPE: DNA
<213> ORGANISM: Artificial sequence
<220> FEATURE:
<223> OTHER INFORMATION: Synthetic oligonucleotide
```

```
<400> SEQUENCE: 4
acatacttct ttacattcca                                              20

<210> SEQ ID NO 5
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 5
acaaattcgg ttctacaggg t                                            21

<210> SEQ ID NO 6
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 6
cagctggttg aaggggacca a                                            21

<210> SEQ ID NO 7
<211> LENGTH: 22
<212> TYPE: RNA
<213> ORGANISM: Artificial sequence
<220> FEATURE:
<223> OTHER INFORMATION: Synthetic oligonucleotide

<400> SEQUENCE: 7
auacauacuu cuuuacauuc ca                                           22

<210> SEQ ID NO 8
<211> LENGTH: 23
<212> TYPE: RNA
<213> ORGANISM: Artificial sequence
<220> FEATURE:
<223> OTHER INFORMATION: Synthetic oligonucleotide

<400> SEQUENCE: 8
cacaaauucg guucuacagg gua                                          23

<210> SEQ ID NO 9
<211> LENGTH: 22
<212> TYPE: RNA
<213> ORGANISM: Artificial sequence
<220> FEATURE:
<223> OTHER INFORMATION: Synthetic oligonucleotide

<400> SEQUENCE: 9
cagcugguug aaggggacca aa                                           22

<210> SEQ ID NO 10
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 10
atacatactt ctttacattc ca                                           22
```

```
<210> SEQ ID NO 11
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 11
cacaaattcg gttctacagg gta                                              23

<210> SEQ ID NO 12
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 12
cagctggttg aaggggacca aa                                               22

<210> SEQ ID NO 13
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 13
ggacccattg gcattctc                                                    18

<210> SEQ ID NO 14
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 14
caggacacag catagaataa tc                                               22

<210> SEQ ID NO 15
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 15
agtgagaggc aacctggaga                                                  20

<210> SEQ ID NO 16
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 16
acactcggac cacatccttc                                                  20

<210> SEQ ID NO 17
<211> LENGTH: 20
<212> TYPE: DNA
<213> ORGANISM: Artificial sequence
<220> FEATURE:
<223> OTHER INFORMATION: Synthetic oligonucleotide
```

```
<400> SEQUENCE: 17
cagtctggac actggctgaa                                              20

<210> SEQ ID NO 18
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 18
ctcgctgatt aggctccaac                                              20

<210> SEQ ID NO 19
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 19
tggtacggta ggagctttgc                                              20

<210> SEQ ID NO 20
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 20
tttttcgtcg cttggagact                                              20

<210> SEQ ID NO 21
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 21
catgctccca ggctgtttat                                              20

<210> SEQ ID NO 22
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 22
gtaacttggc agtttcagtg                                              20

<210> SEQ ID NO 23
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 23
tgcaacatgt actggcgaag a                                            21
```

<210> SEQ ID NO 24
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 24
tcttccacaa gccccagg                                                 18

<210> SEQ ID NO 25
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 25
acagaggctg gtggcaacc                                                19

<210> SEQ ID NO 26
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 26
accattacct tgtcactgtc catga                                          25

<210> SEQ ID NO 27
<211> LENGTH: 33
<212> TYPE: DNA
<213> ORGANISM: Artificial sequence
<220> FEATURE:
<223> OTHER INFORMATION: Synthetic oligonucleotide

<400> SEQUENCE: 27
cgggacaagt acaaggcact gcggcagatc cgg                                 33

<210> SEQ ID NO 28
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 28
ccggatctgc cgcagtgcct tgtacttccg                                     30

<210> SEQ ID NO 29
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 29
tgacgatctg gacaacctca agca                                           24

<210> SEQ ID NO 30
<211> LENGTH: 24
<212> TYPE: DNA
<213> ORGANISM: Artificial sequence
<220> FEATURE:
<223> OTHER INFORMATION: Synthetic oligonucleotide

```
<400> SEQUENCE: 30
atccaatggt gtagtcgctg gtga                                      24

<210> SEQ ID NO 31
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 31
gatacgttct tacagaaggc                                           20

<210> SEQ ID NO 32
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 32
acccatctgg caaaataaac                                           20

<210> SEQ ID NO 33
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 33 ggagggatc agtatataca                                            20

<210> SEQ ID NO 34
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 34
gaagatgatg gagtagatgg                                           20

<210> SEQ ID NO 35
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 35
caattccttg ctgcttctcc                                           20

<210> SEQ ID NO 36
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 36
gcctttgttt tgctcctcag                                           20
```

```
<210> SEQ ID NO 37
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 37
aaaaagggtg tgaccgagtg                                                    20

<210> SEQ ID NO 38
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 38
gcatcttctt ccccaaacaa                                                    20

<210> SEQ ID NO 39
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 39
cctgaacgcc tacaagaagc                                                    20

<210> SEQ ID NO 40
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 40
atggttccca gtttgagtgc                                                    20

<210> SEQ ID NO 41
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 41
gagaggagtg aggcaacagg                                                    20

<210> SEQ ID NO 42
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 42
accccagaca caggtttgag                                                    20

<210> SEQ ID NO 43
<211> LENGTH: 20
<212> TYPE: DNA
<213> ORGANISM: Artificial sequence
<220> FEATURE:
<223> OTHER INFORMATION: Synthetic oligonucleotide
```

```
<400> SEQUENCE: 43
gagacgcgac ttttcaggac                                              20

<210> SEQ ID NO 44
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 44
gatccaaagg ggaaaagcat                                              20

<210> SEQ ID NO 45
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 45
gttctggcga aaaatccaaa                                              20

<210> SEQ ID NO 46
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 46
tcgaacaatt gcagcatca                                               19

<210> SEQ ID NO 47
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 47
cattcctggg gctagtggta                                              20

<210> SEQ ID NO 48
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 48
ccatctgaac caaggcattt                                              20

<210> SEQ ID NO 49
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 49
atcccgtgga gtgaaggtc                                               19
```

```
<210> SEQ ID NO 50
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 50
tctccagcat cacgtctctg                                                 20

<210> SEQ ID NO 51
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 51
agcccatttt tcatttgcac                                                 20

<210> SEQ ID NO 52
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 52
tcgtctggtg ttggttggta                                                 20

<210> SEQ ID NO 53
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 53
cctgagcgtc cagaaatgg                                                  19

<210> SEQ ID NO 54
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 54
ggactgttat tcgcaagctg gtt                                             23

<210> SEQ ID NO 55
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 55
catgaagtgt gacgtggaca                                                 20

<210> SEQ ID NO 56
<211> LENGTH: 20
<212> TYPE: DNA
<213> ORGANISM: Artificial sequence
<220> FEATURE:
<223> OTHER INFORMATION: Synthetic oligonucleotide
```

```
<400> SEQUENCE: 56
cacggagtac ttgcgctcag                                              20

<210> SEQ ID NO 57
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 57
gacttcaaca gcgacaccc                                               19

<210> SEQ ID NO 58
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 58
gccaaattcg ttgtcatacc a                                            21

<210> SEQ ID NO 59
<211> LENGTH: 20
<212> TYPE: RNA
<213> ORGANISM: Artificial sequence
<220> FEATURE:
<223> OTHER INFORMATION: Synthetic oligonucleotide

<400> SEQUENCE: 59
uacauacuuc uuauguaccc                                              20

<210> SEQ ID NO 60
<211> LENGTH: 22
<212> TYPE: RNA
<213> ORGANISM: Artificial sequence
<220> FEATURE:
<223> OTHER INFORMATION: Synthetic oligonucleotide

<400> SEQUENCE: 60
acagauucga uucuagggga au                                           22

<210> SEQ ID NO 61
<211> LENGTH: 22
<212> TYPE: RNA
<213> ORGANISM: Artificial sequence
<220> FEATURE:
<223> OTHER INFORMATION: Synthetic oligonucleotide

<400> SEQUENCE: 61
agcugguaaa auggaaccaa au                                           22

<210> SEQ ID NO 62
<211> LENGTH: 21
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(19)
<223> OTHER INFORMATION: RNA

<400> SEQUENCE: 62
ccacuagagu gguggaaaat t                                            21
```

```
<210> SEQ ID NO 63
<211> LENGTH: 21
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(19)
<223> OTHER INFORMATION: RNA

<400> SEQUENCE: 63
uuuuccacca cucuaguggt t                                              21

<210> SEQ ID NO 64
<211> LENGTH: 21
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(19)
<223> OTHER INFORMATION: RNA

<400> SEQUENCE: 64
ggacugggcu gaaguacaat t                                              21

<210> SEQ ID NO 65
<211> LENGTH: 21
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(19)
<223> OTHER INFORMATION: RNA

<400> SEQUENCE: 65
uuguacuuca gcccagucct t                                              21

<210> SEQ ID NO 66
<211> LENGTH: 21
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(19)
<223> OTHER INFORMATION: RNA

<400> SEQUENCE: 66
ccgagaaguu ugugguaaat t                                              21

<210> SEQ ID NO 67
<211> LENGTH: 21
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(19)
<223> OTHER INFORMATION: RNA

<400> SEQUENCE: 67
uuuaccacaa acuucucggt t                                              21
```

<210> SEQ ID NO 68
<211> LENGTH: 21
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(19)
<223> OTHER INFORMATION: RNA

<400> SEQUENCE: 68
cuuccuaauc cgagacacat t                                              21

<210> SEQ ID NO 69
<211> LENGTH: 21
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(19)
<223> OTHER INFORMATION: RNA

<400> SEQUENCE: 69
ugugucucgg auuaggaagt t                                              21

<210> SEQ ID NO 70
<211> LENGTH: 21
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(19)
<223> OTHER INFORMATION: RNA

<400> SEQUENCE: 70
ccagaggauu ugccagaaat t                                              21

<210> SEQ ID NO 71
<211> LENGTH: 21
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(19)
<223> OTHER INFORMATION: RNA

<400> SEQUENCE: 71
ugugucucgg auuaggaagt t                                              21

<210> SEQ ID NO 72
<211> LENGTH: 21
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(19)
<223> OTHER INFORMATION: RNA

<400> SEQUENCE: 72
ggugaacacu uaacagcaat t                                              21

```
<210> SEQ ID NO 73
<211> LENGTH: 21
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(19)
<223> OTHER INFORMATION: RNA

<400> SEQUENCE: 73
uugcuguuaa guguucacct t                                              21

<210> SEQ ID NO 74
<211> LENGTH: 21
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(19)
<223> OTHER INFORMATION: RNA

<400> SEQUENCE: 74
gggaaugaca gcaagaaaut t                                              21

<210> SEQ ID NO 75
<211> LENGTH: 21
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(19)
<223> OTHER INFORMATION: RNA

<400> SEQUENCE: 75
auuucuugcu gucauuccct t                                              21

<210> SEQ ID NO 76
<211> LENGTH: 21
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(19)
<223> OTHER INFORMATION: RNA

<400> SEQUENCE: 76
ccauaaugaa ggaggucuut t                                              21

<210> SEQ ID NO 77
<211> LENGTH: 21
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(19)
<223> OTHER INFORMATION: RNA

<400> SEQUENCE: 77
aagaccuccu ucauuauggt t                                              21
```

```
<210> SEQ ID NO 78
<211> LENGTH: 21
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(19)
<223> OTHER INFORMATION: RNA

<400> SEQUENCE: 78
ugaccaagau gcucgggaut t                                              21

<210> SEQ ID NO 79
<211> LENGTH: 21
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(19)
<223> OTHER INFORMATION: RNA

<400> SEQUENCE: 79
aucccgagca ucuuggucat t                                              21

<210> SEQ ID NO 80
<211> LENGTH: 21
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(19)
<223> OTHER INFORMATION: RNA

<400> SEQUENCE: 80
ggagguaccu ucuuccaaat t                                              21

<210> SEQ ID NO 81
<211> LENGTH: 21
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(19)
<223> OTHER INFORMATION: RNA

<400> SEQUENCE: 81
uaucaaacuu ccucuucugt t                                              21

<210> SEQ ID NO 82
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 82
gctcgagtaa agcaaaacaa aggcatcagc                                     30
```

```
<210> SEQ ID NO 83
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 83
gcggccgcaa ggcttgtcac caatgaatga                              30

<210> SEQ ID NO 84
<211> LENGTH: 29
<212> TYPE: DNA
<213> ORGANISM: Artificial sequence
<220> FEATURE:
<223> OTHER INFORMATION: Synthetic oligonucleotide

<400> SEQUENCE: 84
aaatgtcaac cattttgtgt aaacgatta                               29

<210> SEQ ID NO 85
<211> LENGTH: 28
<212> TYPE: DNA
<213> ORGANISM: Artificial sequence
<220> FEATURE:
<223> OTHER INFORMATION: Synthetic oligonucleotide

<400> SEQUENCE: 85
aaatggttga catttcttca tttaccag                                28

<210> SEQ ID NO 86
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 86
gctcgagtaa taccgcctgg tatgtctgtg                              30

<210> SEQ ID NO 87
<211> LENGTH: 31
<212> TYPE: DNA
<213> ORGANISM: Artificial sequence
<220> FEATURE:
<223> OTHER INFORMATION: Synthetic oligonucleotide

<400> SEQUENCE: 87
gcggccgcaa tgcagatgcc atttatttgg t                            31

<210> SEQ ID NO 88
<211> LENGTH: 29
<212> TYPE: DNA
<213> ORGANISM: Artificial sequence
<220> FEATURE:
<223> OTHER INFORMATION: Synthetic oligonucleotide

<400> SEQUENCE: 88
ttatgtcaac cataaatggc atctgcatt                               29

<210> SEQ ID NO 89
<211> LENGTH: 28
<212> TYPE: DNA
<213> ORGANISM: Artificial sequence
<220> FEATURE:
<223> OTHER INFORMATION: Synthetic oligonucleotide
```

<400> SEQUENCE: 89
ttatggttga cataagtata gtcgttat                                       28

<210> SEQ ID NO 90
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 90
gctcgagtaa ccctgttgga caggattgat                                     30

<210> SEQ ID NO 91
<211> LENGTH: 35
<212> TYPE: DNA
<213> ORGANISM: Artificial sequence
<220> FEATURE:
<223> OTHER INFORMATION: Synthetic oligonucleotide

<400> SEQUENCE: 91
gcggccgcaa tttttaaaga aagcatcttt tatgg                               35

<210> SEQ ID NO 92
<211> LENGTH: 29
<212> TYPE: DNA
<213> ORGANISM: Artificial sequence
<220> FEATURE:
<223> OTHER INFORMATION: Synthetic oligonucleotide

<400> SEQUENCE: 92
tcttatcaac ccacttcagt cagaaatgt                                      29

<210> SEQ ID NO 93
<211> LENGTH: 28
<212> TYPE: DNA
<213> ORGANISM: Artificial sequence
<220> FEATURE:
<223> OTHER INFORMATION: Synthetic oligonucleotide

<400> SEQUENCE: 93
agtgggttga taagactgcg aacaatca                                       28

<210> SEQ ID NO 94
<211> LENGTH: 32
<212> TYPE: DNA
<213> ORGANISM: Artificial sequence
<220> FEATURE:
<223> OTHER INFORMATION: Synthetic oligonucleotide

<400> SEQUENCE: 94
gctcgagtaa aaacctgtcc tggaattcta cc                                  32

<210> SEQ ID NO 95
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 95
gcggccgcaa gatggccttt gggtcaataa                                     30

<210> SEQ ID NO 96
<211> LENGTH: 29
<212> TYPE: DNA
<213> ORGANISM: Artificial sequence
<220> FEATURE:
<223> OTHER INFORMATION: Synthetic oligonucleotide

<400> SEQUENCE: 96
ctggatcaac gagctggcct gaaaattac                                29

<210> SEQ ID NO 97
<211> LENGTH: 28
<212> TYPE: DNA
<213> ORGANISM: Artificial sequence
<220> FEATURE:
<223> OTHER INFORMATION: Synthetic oligonucleotide

<400> SEQUENCE: 97
gctcgttgat ccaggtagaa ttccagga                                 28

<210> SEQ ID NO 98
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 98
gctcgagtaa ctcccccagc taggaaacag                               30

<210> SEQ ID NO 99
<211> LENGTH: 28
<212> TYPE: DNA
<213> ORGANISM: Artificial sequence
<220> FEATURE:
<223> OTHER INFORMATION: Synthetic oligonucleotide

<400> SEQUENCE: 99
gcggccgcaa agagatgggg cggtcagt                                 28

<210> SEQ ID NO 100
<211> LENGTH: 29
<212> TYPE: DNA
<213> ORGANISM: Artificial sequence
<220> FEATURE:
<223> OTHER INFORMATION: Synthetic oligonucleotide

<400> SEQUENCE: 100
gacgttcaac cgccatcccc agccccaaa                                29

<210> SEQ ID NO 101
<211> LENGTH: 28
<212> TYPE: DNA
<213> ORGANISM: Artificial sequence
<220> FEATURE:
<223> OTHER INFORMATION: Synthetic oligonucleotide

<400> SEQUENCE: 101
tggcggttga acgtctctgc ccacgttc                                 28

<210> SEQ ID NO 102
<211> LENGTH: 29
<212> TYPE: DNA
<213> ORGANISM: Artificial sequence
<220> FEATURE:
<223> OTHER INFORMATION: Synthetic oligonucleotide

```
<400> SEQUENCE: 102
gctcgagtaa gcgggatgct ttgaacatt                                   29

<210> SEQ ID NO 103
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 103
gcggccgcaa ctccagcgtc atagagatcc                                  30

<210> SEQ ID NO 104
<211> LENGTH: 29
<212> TYPE: DNA
<213> ORGANISM: Artificial sequence
<220> FEATURE:
<223> OTHER INFORMATION: Synthetic oligonucleotide

<400> SEQUENCE: 104
atcaatcaac caggtgtgga tgaggtcac                                   29

<210> SEQ ID NO 105
<211> LENGTH: 28
<212> TYPE: DNA
<213> ORGANISM: Artificial sequence
<220> FEATURE:
<223> OTHER INFORMATION: Synthetic oligonucleotide

<400> SEQUENCE: 105
acctggttga ttgatggctg tttcaatg                                    28
```